US012616473B2

(12) United States Patent (10) Patent No.: US 12,616,473 B2
Holdmeyer et al. (45) Date of Patent: May 5, 2026

(54) STAPLE CARTRIDGE RETENTION FEATURES FOR SURGICAL STAPLER

(71) Applicant: Cilag GmbH International, Zug (CH)

(72) Inventors: Seth D. Holdmeyer, Sharonville, OH (US); Kenneth C. Boshell, Jr., Cincinnati, OH (US); Jonathan Z. Von Stein, Cincinnati, OH (US); Heather E. Dickson, Cincinnati, OH (US); Christopher A. Denzinger, Cincinnati, OH (US); Mark D. Overmyer, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/758,377

(22) Filed: Jun. 28, 2024

(65) Prior Publication Data

US 2026/0000399 A1     Jan. 1, 2026

(51) Int. Cl.
    *A61B 17/072* (2006.01)
(52) U.S. Cl.
    CPC ................... *A61B 17/07207* (2013.01); *A61B 2017/07264* (2013.01); *A61B 2017/07271* (2013.01); *A61B 2017/07285* (2013.01)
(58) Field of Classification Search
    CPC ...... A61B 17/068–0686; A61B 17/072; A61B 17/07207; A61B 2017/07264; A61B 2017/07271; A61B 2017/07285; A61B 2017/07257
    See application file for complete search history.

(56) References Cited

U.S. PATENT DOCUMENTS 3,604,561 A * 9/1971 Mallina ............... A61B 17/0686
                                                    227/19
4,241,861 A * 12/1980 Fleischer ............. A61B 17/072
                                                    227/135

(Continued)

FOREIGN PATENT DOCUMENTS

CN         202982103 U      6/2013
WO      WO-03094747 A1 * 11/2003 ........... A61B 17/072
WO   WO-2020244463 A1 * 12/2020 ........... A61B 17/072

OTHER PUBLICATIONS

U.S. Appl. No. 18/588,684, entitled "Methods of Surgical Stapling," filed Feb. 27, 2024.

(Continued)

*Primary Examiner* — Linda J. Hodge
(74) *Attorney, Agent, or Firm* — FBT Gibbons LLP

(57) ABSTRACT

An apparatus includes an end effector, a staple cartridge retainer, and a staple cartridge datum locator. The end effector includes a first jaw, a second jaw, a knife sled, and a replaceable staple cartridge. The first jaw can selectively couple with the replaceable staple cartridge and the knife sled can actuate along a firing stroke to cut and staple tissue called by the first and second jaws. The staple cartridge retainer is located along a distal portion of the end effector and includes a resilient retention body that can inhibit the replaceable staple cartridge from disassociating with the first jaw. The staple cartridge datum location is located along a proximal portion of the end effector and can position the replaceable staple cartridge at its predetermined datum location when the first and second jaw are in a closed position.

11 Claims, 40 Drawing Sheets

(56) References Cited

U.S. PATENT DOCUMENTS

| | | | | |
|---|---|---|---|---|
| 4,442,964 | A * | 4/1984 | Becht | A61B 17/072 |
| | | | | 227/19 |
| 6,988,649 | B2 | 1/2006 | Shelton, IV et al. | |
| 8,012,170 | B2 | 9/2011 | Whitman et al. | |
| 8,989,903 | B2 | 3/2015 | Weir et al. | |
| 9,226,750 | B2 | 1/2016 | Weir et al. | |
| 9,526,499 | B2 | 12/2016 | Kostrzewski et al. | |
| 9,700,320 | B2 | 7/2017 | DiNardo et al. | |
| 9,706,993 | B2 * | 7/2017 | Hessler | A61B 17/0682 |
| 9,814,530 | B2 | 11/2017 | Weir et al. | |
| 10,206,748 | B2 | 2/2019 | Burbank | |
| 10,245,030 | B2 | 4/2019 | Hunter et al. | |
| 10,303,641 | B2 | 5/2019 | Collins et al. | |
| 10,335,147 | B2 | 7/2019 | Rector et al. | |
| 10,492,785 | B2 | 12/2019 | Overmyer et al. | |
| 10,617,412 | B2 | 4/2020 | Shelton, IV et al. | |
| 10,863,988 | B2 | 12/2020 | Patel et al. | |
| 10,881,403 | B2 | 1/2021 | Shelton, IV et al. | |
| 10,959,726 | B2 | 3/2021 | Williams et al. | |
| 11,147,552 | B2 | 10/2021 | Burbank et al. | |
| 11,234,698 | B2 | 2/2022 | Shelton, IV et al. | |
| 11,311,293 | B2 | 4/2022 | Roberts et al. | |
| 11,439,390 | B2 | 9/2022 | Patel et al. | |
| 11,452,524 | B2 | 9/2022 | Chavan et al. | |
| 11,504,124 | B2 | 11/2022 | Patel et al. | |
| 11,529,140 | B2 | 12/2022 | Shelton, IV et al. | |
| 11,589,865 | B2 | 2/2023 | Shelton, IV et al. | |
| 11,717,287 | B2 | 8/2023 | Williams et al. | |
| 11,844,520 | B2 | 12/2023 | Shelton, IV et al. | |
| 11,903,582 | B2 | 2/2024 | Baxter, III et al. | |
| 2009/0048589 | A1 * | 2/2009 | Takashino | A61B 17/115 |
| | | | | 606/28 |
| 2010/0213241 | A1 * | 8/2010 | Bedi | A61B 17/07207 |
| | | | | 227/180.1 |
| 2013/0197516 | A1 * | 8/2013 | Kappel | A61B 17/29 |
| | | | | 606/46 |
| 2016/0058440 | A1 * | 3/2016 | Dinardo | A61B 17/07207 |
| | | | | 227/176.1 |
| 2019/0038291 | A1 * | 2/2019 | Guerrera | A61B 17/07207 |
| 2019/0059888 | A1 | 2/2019 | Shelton, IV et al. | |
| 2019/0290308 | A1 * | 9/2019 | Worthington | H01R 13/2407 |
| 2022/0071726 | A1 | 3/2022 | Rockrohr et al. | |

OTHER PUBLICATIONS

International Search Report and Written Opinion dated Sep. 1, 2025, for International Application No. PCT/IB2025/056621, 12 pages.

* cited by examiner

STAPLE CARTRIDGE RETENTION FEATURES FOR SURGICAL STAPLER

BACKGROUND

In some settings, endoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion that is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

The surgical stapling features of the present disclosure seek to retain a staple cartridge within the end effector when the end effector is in an open position, and further align the staple cartridge with staple forming pockets of an anvil when the end effector reaches a closed position. Specifically, such features of the present disclosure place the staple cartridge at a predetermined datum relative to the end effector. While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate examples of the invention, and, together with the general description of the invention given above, and the detailed description of the examples given below, serve to explain the principles of the present invention.

DETAILED DESCRIPTION

Figure 1:
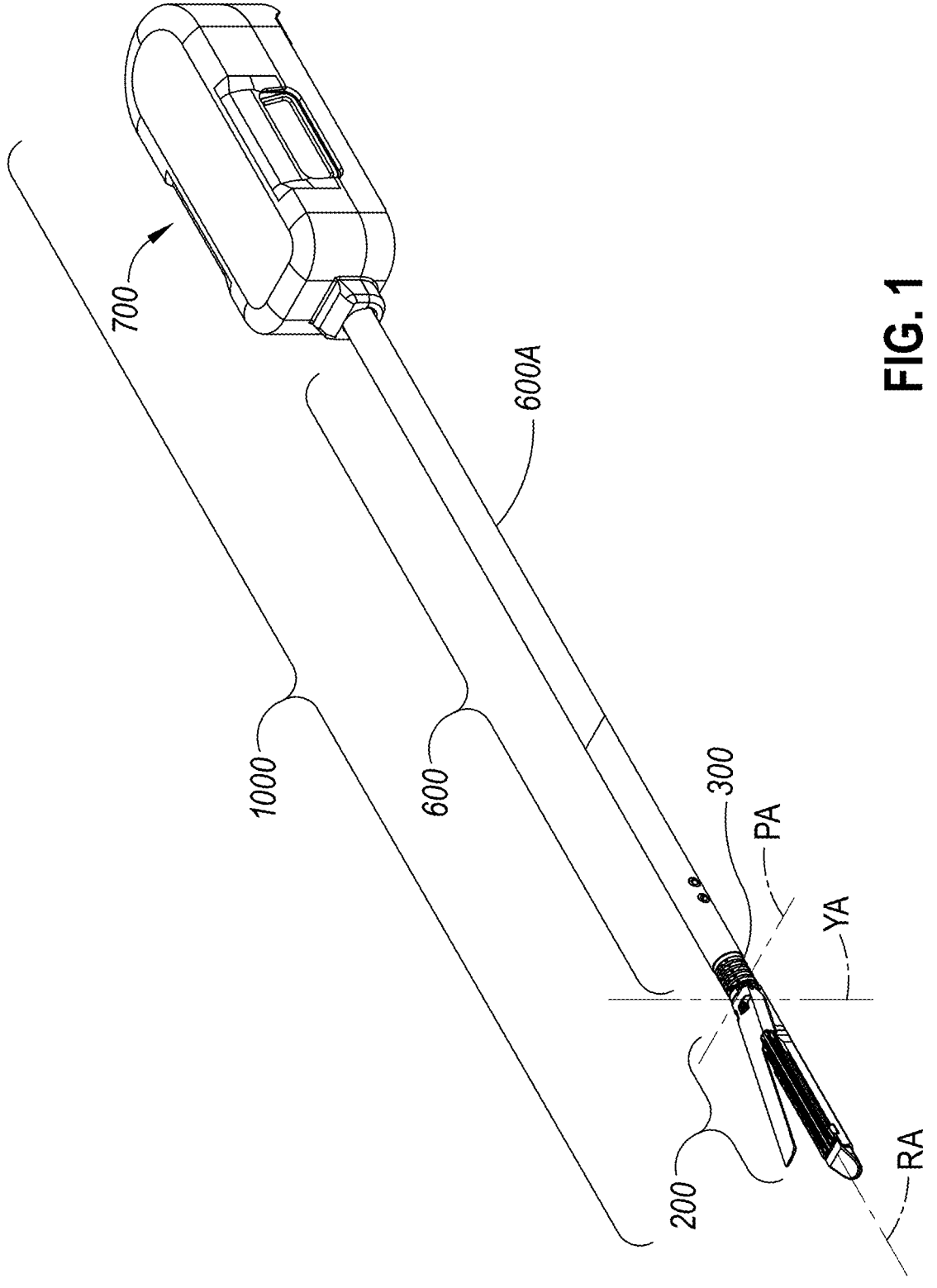
FIG. 1 is a perspective view of an illustrative surgical instrument having a housing, a shaft assembly, an articulation joint, and an end effector.

The following detailed description should be read with reference to the drawings, in which like elements in different drawings are identically numbered. The drawings, which are not necessarily to scale, depict selected versions and are not intended to limit the scope of the invention. The detailed description illustrates by way of example, not by way of limitation, the principles of the invention. This description will clearly enable one skilled in the art to make and use the invention, and describes several versions, adaptations, variations, alternatives and uses of the invention, including what is presently believed to be the best mode of carrying out the invention.

Numerous specific details are set forth to provide a thorough understanding of the overall structure, function, manufacture, and use of the versions as described in the specification and illustrated in the accompanying drawings. Well-known operations, components, and elements have not been described in detail so as not to obscure the versions described in the specification. The reader will understand that the versions described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a robotic platform manipulating the housing portion of the surgical instrument. The term "proximal" refers to the portion closest to the robotic platform and the term "distal" refers to the portion located away from the robotic platform. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures, and "substantially equal" values encompass nominally equal values.

Furthermore, the use of "couple", "coupled", or similar phrases should not be construed as being limited to a certain number of components or a particular order of components unless the context clearly dictates otherwise.

I. Overview of Illustrative Surgical Instrument

Figure 2:
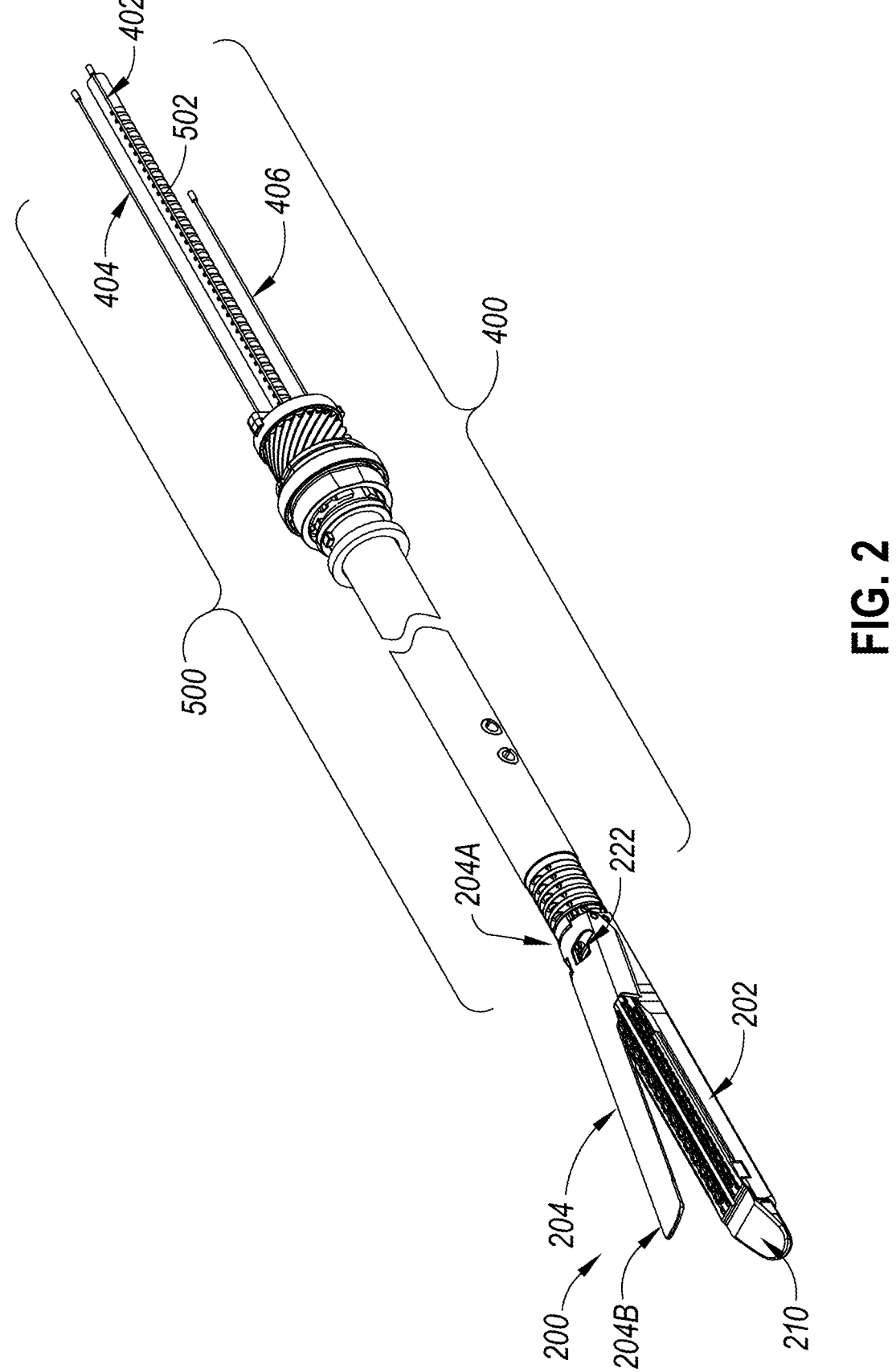
FIG. 2 is a partial perspective view of the surgical instrument of FIG. 1, with select components omitted from view to reveal portions of a cable articulation subsystem, a knife firing subsystem, and a roll subsystem of the surgical instrument.

FIGS. 1-2 show an illustrative surgical instrument 1000 that is configured to grasp, clamp, incise, and seal patient tissue with staples. The surgical instrument 1000 comprises an end effector 200, an articulation joint 300 (also referred to as a "continuum joint"), an articulation drive subsystem 400 configured to articulate the end effector 200 via the articulation joint 300, a knife firing subsystem 500 configured to actuate the end effector 200 between various positions (e.g., an open position, a grasping position, and a clamping position) and to incise and staple patient tissue, a roll subsystem 600 configured to rotate the end effector 200 about a roll axis RA, and a housing 700.

Figure 3:
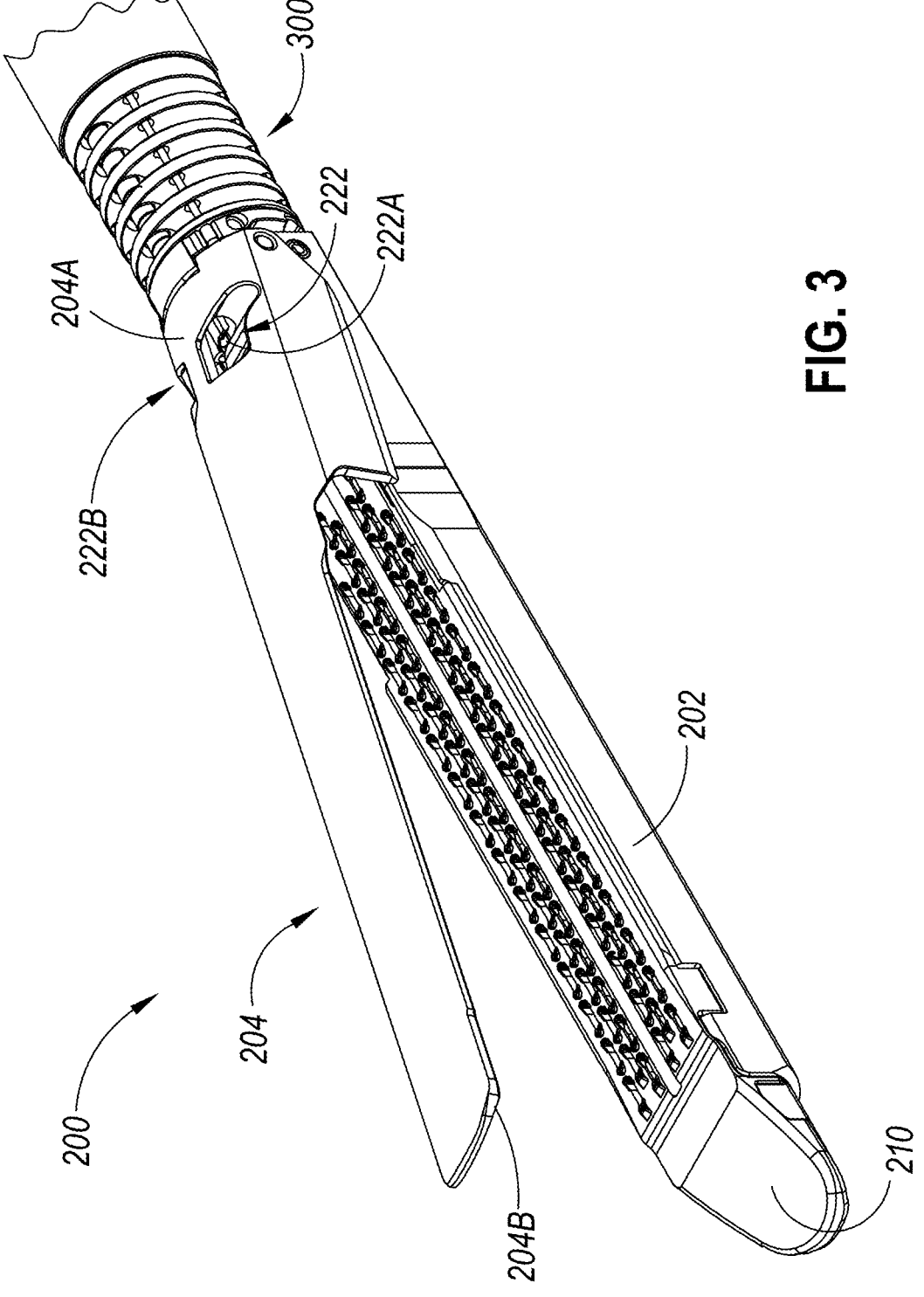
FIG. 3 is an enlarged perspective view of the end effector and the articulation joint of the surgical instrument of FIG. 1.
Figures 4, 5:
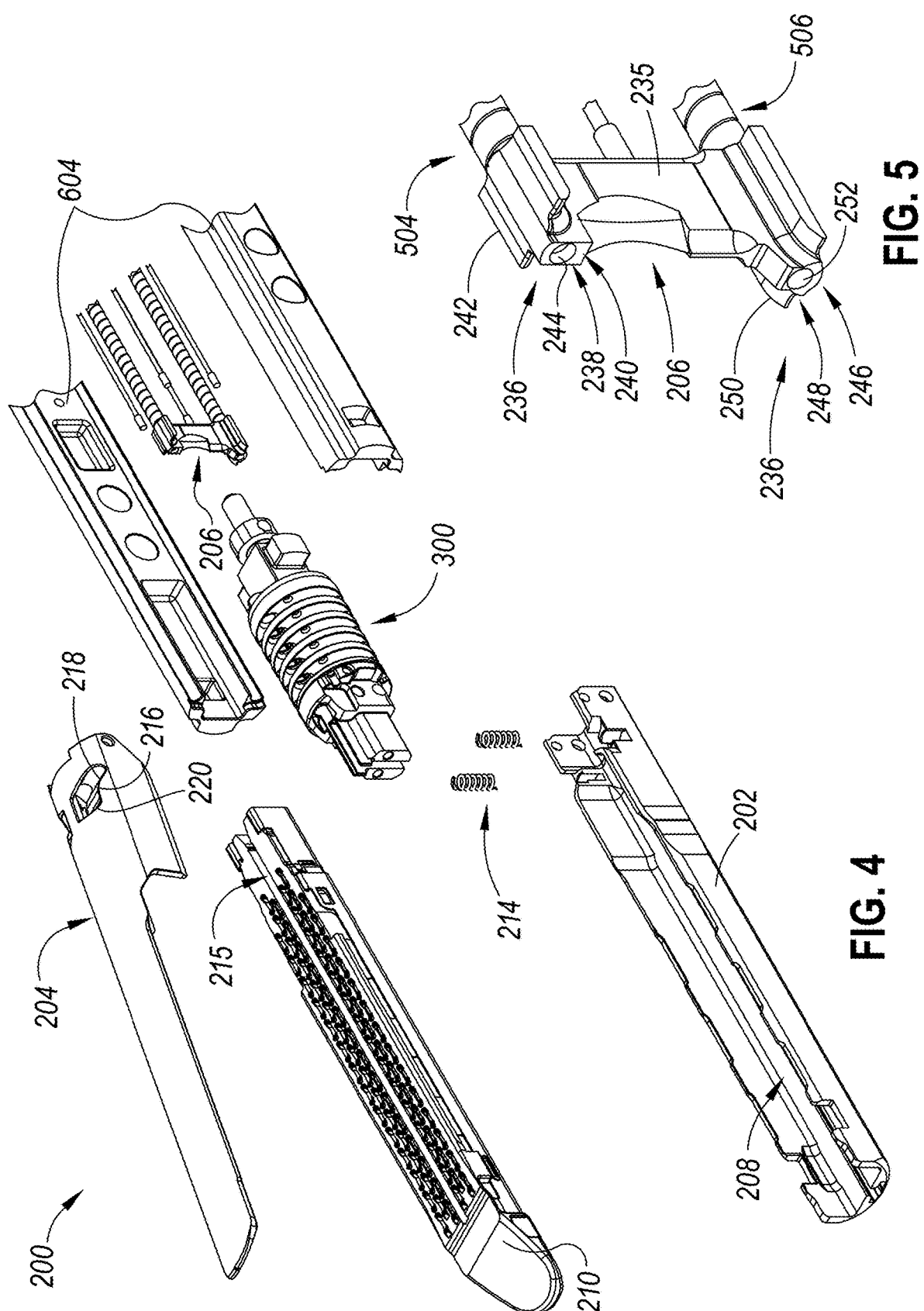
FIG. 4 is an exploded view of a distal end portion of the surgical instrument of FIG. 1.
FIG. 5 is an enlarged perspective view of a knife of the end effector of the surgical instrument of FIG. 1.
Figure 7:
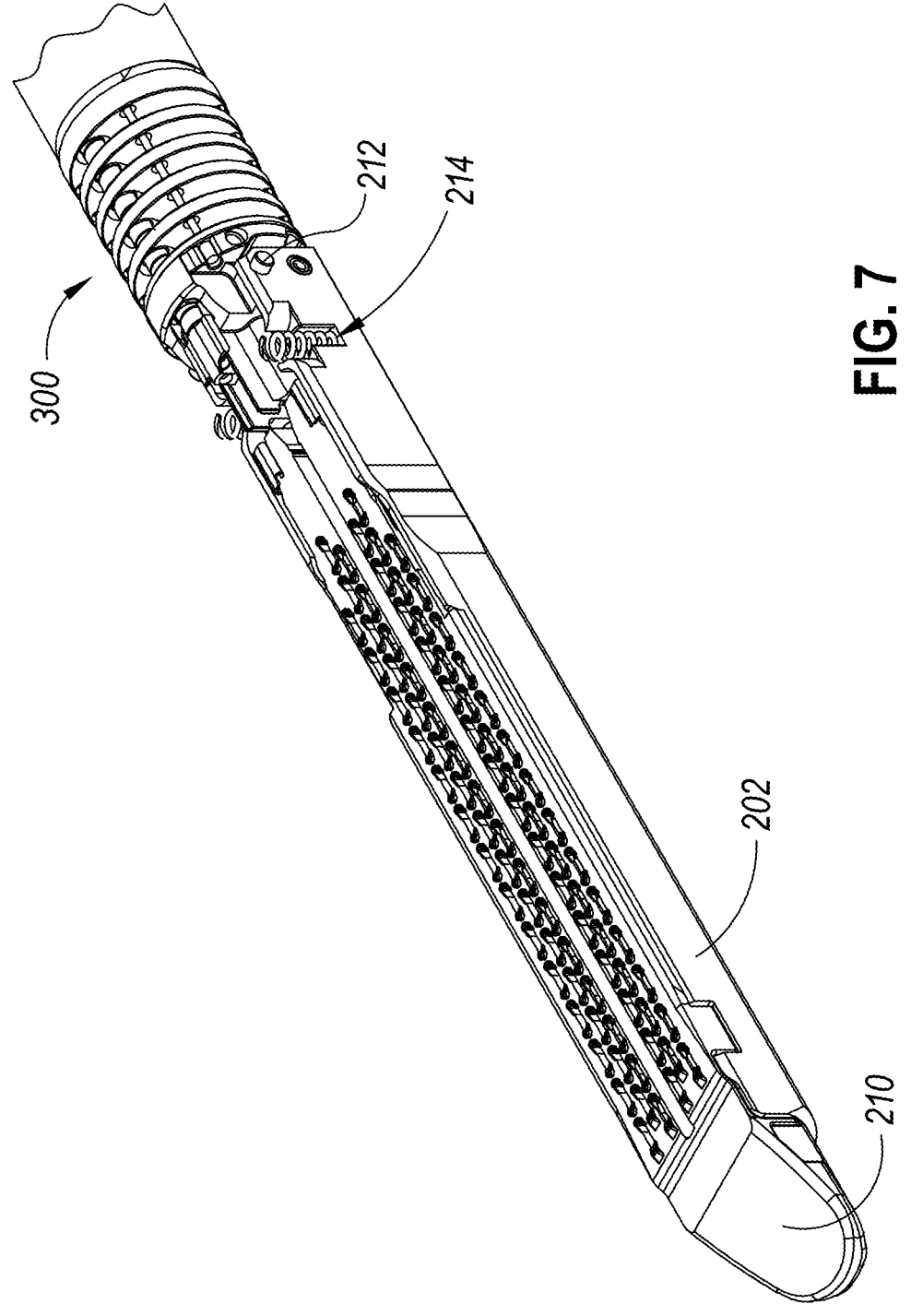
FIG. 7 is an enlarged perspective view of the end effector and the articulation joint of FIG. 3, with an anvil of the end effector omitted.

As shown best in FIGS. 3-4, the end effector 200 comprises a first jaw 202 (also known as a "cartridge jaw" or a "channel") and a second jaw 204 (also known as an "anvil jaw" or just "anvil") movable relative to the cartridge jaw 202 between an open position and a closed position. The cartridge jaw 202 and anvil jaw 204 may be elongated in form. The cartridge jaw 202 defines an elongated channel 208 for receiving a staple cartridge 210 (also known as a "reload"). The anvil jaw 204 has a proximal end 204A, a distal end 204B, and a ramp surface 216 defined at the proximal end 204A, which is described in greater detail below with respect to FIGS. 4 and 9A-9D. The cartridge jaw 202 and anvil jaw 204 are pivotally coupled via a pivot pin 212 that extends through the cartridge jaw 202 and the anvil jaw 204. As seen in FIG. 7, one or more biasing springs 214 extend between the cartridge jaw 202 and anvil jaw 204 to bias the anvil jaw 204 to the open position.

The ramp surface 216 may be visible via a kidney bean-shaped opening 222 (which may be formed as part of the manufacturing process to make the ramp surface 216) that has a first lateral end 222A and a second lateral end 222B. In other words, the kidney bean-shaped opening may be open at its lateral ends 222A, 222B (FIG. 3). As seen in FIG. 4, the ramp surface 216 forms a lower surface of the kidney bean-shaped opening 222. The ramp surface 216 can be arcuately shaped. For example, as shown particularly in FIGS. 4 and 9A-9D, it may be upwardly sloped at a first angle 218 and arcuately taper, in a distal direction, to a substantially horizontal second angle 220.

Figures 8A, 8B:
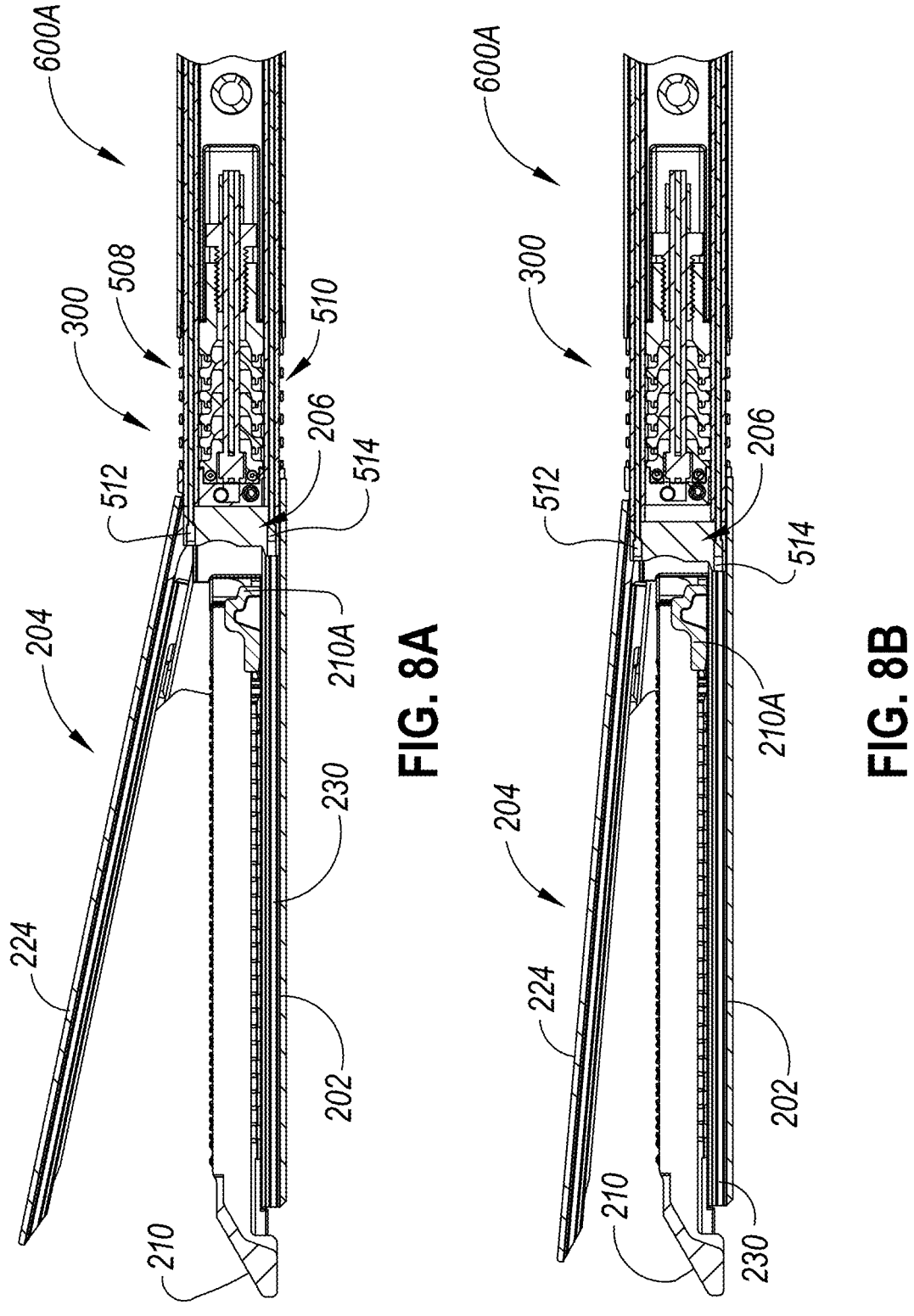
FIG. 8A is a side cross-sectional view of a distal end portion of the surgical instrument of FIG. 1, depicting the anvil in an open position.
FIG. 8B is a side cross-sectional view of the distal end portion of the surgical instrument of FIG. 1, depicting the anvil in a grasping position with the knife partially advanced.

The anvil jaw 204 further defines a longitudinally extending upper knife channel 224 (see FIG. 8A, etc.). As shown particularly in FIG. 6, the upper knife channel 224 includes a centrally disposed cylindrical upper knife channel portion 226 and at least one lateral upper knife channel wing 228 that extends away from the upper knife channel portion 226. While the term 'cylindrical' is used, the channel portion 226 need not resemble a perfect cylinder.

Figure 17:
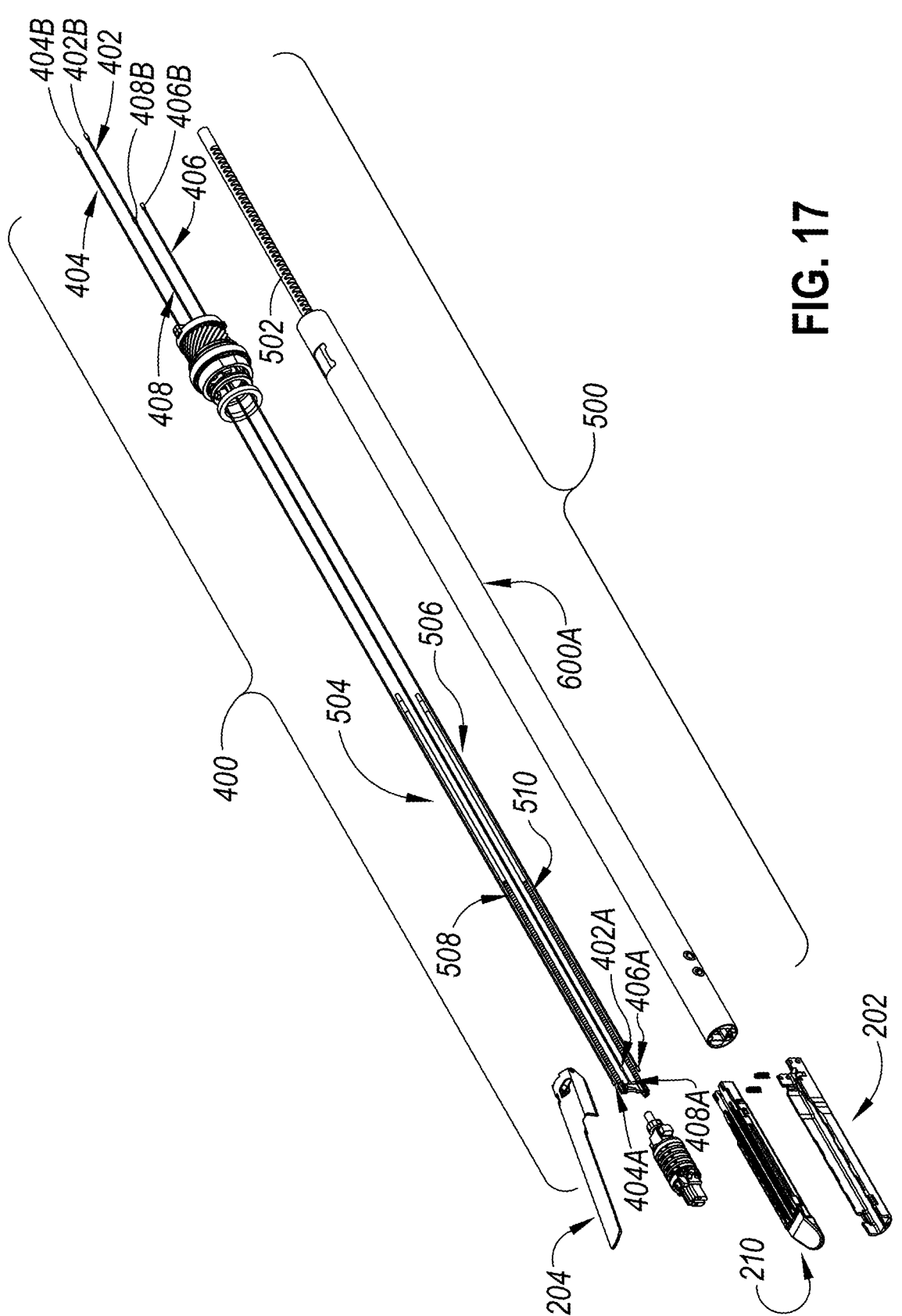
FIG. 17 is an exploded perspective view of a portion of the surgical instrument of FIG. 1, depicting portions of the cable articulation subsystem, the knife firing subsystem, and the roll subsystem.

As shown in FIGS. 2 and 17, the surgical instrument 1000 further comprises a knife firing subsystem 500 operable to close the anvil jaw 204 during a closure stroke. After the end effector 200 is closed, the knife firing subsystem 500 is operable to incise and staple, with staples from the staple cartridge 210, the patient tissue captured between the staple cartridge 210 (which is retained by the cartridge jaw 202) and anvil jaw 204 during a firing stroke.

Figure 6:
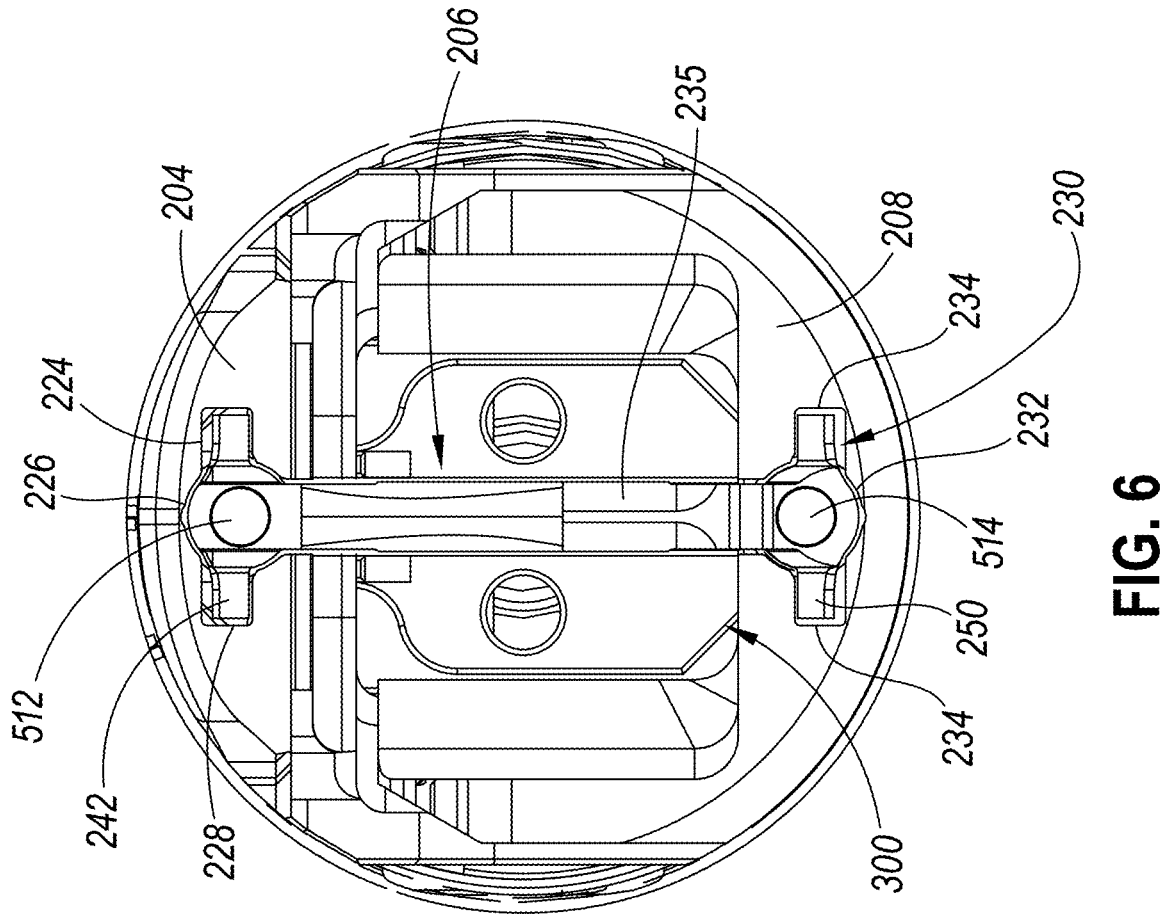
FIG. 6 is an end view of the end effector of FIG. 3.

As shown best in FIGS. 4-6, the knife firing subsystem 500, explained further below in greater detail, includes a knife 206 having a knife sled 236. The knife sled 236 functions as a firing driver by driving cartridge sled 210A distally through a firing stroke, as described below. In some instances, knife sled 236 may be referred to as an I-beam. The knife sled 236 includes an upper knife tab 238, a lower knife tab 246, and a vertical column 235 coupling and extending between upper knife tab 238 and lower knife tab 246. The upper knife tab 238 includes a centrally disposed cylindrical upper knife tab portion 240 and at least one upper knife tab lateral wing 242 that extends away from the upper knife tab portion 240. While the term 'cylindrical' is used, the tab portion need not resemble a perfect cylinder.

The upper knife tab 238 may include a pair of lateral wings 242 configured to slidably ride in the upper knife channel 224 to move the anvil jaw 204 between the open position, the grasping position, and the clamping position. Accordingly, the end effector 200 employs "knife-based closure" in which closure of the anvil jaw 204 relative to the cartridge jaw 202 is driven by distal advancement of the knife 206. Each lateral wing 242 may include a ramped surface 242A that engages the anvil ramp surface 216. The upper knife tab portion 240 defines an upper knife tab opening 244 that is configured to receive a barrel crimp coupled to a center cable 512, which is described in greater detail below. The lower knife tab 246 includes a centrally disposed cylindrical lower knife tab portion 248 and at least one lower knife tab lateral wing 250 that extends away from the lower knife tab portion 248. While the term 'cylindrical' is used, the lower knife tab portion 248 need not resemble a perfect cylinder. In some versions, the lower knife tab 246 includes a pair of lateral wings 250. The lower knife tab portion 248 defines a lower knife tab opening 252 that is configured to receive a barrel crimp coupled to a center cable 514, as described in greater detail below.

The staple cartridge 210 may be generally constructed and operable in accordance with the teachings of U.S. patent application Ser. No. 18/588,684, entitled "Methods of Surgical Stapling," filed on Feb. 27, 2024, issued as U.S. Pat. No. 12,471,913 on Nov. 18, 2025, the disclosure of which is incorporated by reference herein in its entirety. In use, the end effector 200 is positioned relative to patient tissue such that the staple cartridge 210 is disposed on a first side of the tissue and the anvil jaw 204 is positioned on an opposed second side of the tissue. The anvil jaw 204 is then approximated toward the staple cartridge 210 to compress and clamp the tissue against the deck of the staple cartridge 210. Thereafter, the surgical instrument 1000 is fired so that the knife 206 advances distally through the staple cartridge 210 to both cut the clamped tissue and simultaneously actuate staple drivers housed within the staple cartridge 210 to drive an array of staples into the clamped tissue on either side of the cut line. Staple cartridge 210 defines an elongate knife channel 215 dimensioned to receive a portion of vertical column 235 in order to accommodate advancement of knife 206 through staple cartridge 210. A portion of cartridge sled 210A is slidably housed within elongate knife channel 215 such that vertical column 235 drives cartridge sled 210A distally as knife 206 advances distally in accordance with the description herein (see FIGS. 8C-8D). In some instances, cartridge sled 210A remains in the distal position (see FIG. 8D) relative to the rest of staple cartridge 210, even after knife 206 is retracted proximally after firing staple cartridge 210 in accordance with the description herein.

As mentioned above, cartridge jaw 202 defines an elongated channel 208 for receiving staple cartridge 210. Additionally, cartridge jaw 202 also defines a lower knife channel 230 (see FIGS. 4, 6, and 8A-9D) dimensioned to slidably receive lower knife tab 246. Referring to FIG. 6, the lower knife channel 230 includes a centrally disposed cylindrical lower knife channel portion 232 and at least one lateral lower knife channel wing 234 that extends away from the lower knife channel portion 232. Cylindrical lower knife channel portion 232 is in communication with elongated channel 208 such that when staple cartridge 210 is suitably coupled to cartridge jaw 202, elongate knife channel 215 of staple cartridge 210 and centrally disposed cylindrical lower knife channel portion 232 are aligned to accommodate actuation of knife sled 236 within both channels 215, 230. Lateral lower knife channel wings 234 are dimensioned to slidably house a respective lower knife tab lateral wing 250. Lower knife tab lateral wings 250 are configured to slidably contact lateral lower knife channel wings 234 as knife 206 is advanced in accordance with the description herein. Contact between lower knife tab lateral wings 250 and lateral lower knife channel wings 234 cooperatively assists lateral wings 242 and upper knife channel 224 to close anvil jaw 204 relative to channel 208 in accordance with the description herein. While the term 'cylindrical' is used, the channel portion 232 need not resemble a perfect cylinder. Other arrangements of staple cavities and staples may be possible. For example, in some versions, a lower knife channel 230 can be defined in the cartridge jaw 202.

Further to the above, the knife sled 236 is moved distally and proximally by a firing rod 502. The firing rod 502 is configured to apply an indirect force to the knife sled 236, via push coils 508, 510 that directly engage the knife sled 236 (discussed in greater detail below), and push the knife sled 236 toward the distal end of the end effector 200 through a firing stroke. As the firing rod 502 is advanced distally, knife sled 236 rides in the lower knife channel 230 and the upper knife channel 224. At the onset of travel, the upper knife tab 238 rides along the anvil ramp surface 216. Specifically, as particularly seen in the sequence of FIGS. 8A-8D and 9A-9D, movement of the knife sled 236 distally causes the upper knife tab ramped surface 242A to slide along the anvil ramp surface 216. This movement first urges the anvil jaw 204 closed to a position (e.g., FIGS. 8B and 9B) where a compressive force is applied to the tissue sufficient to grasp it (referred to as the grasping position). Continued movement of the knife sled 236 up the ramp surface 216 (e.g., see FIGS. 8C and 9C) results in a compressive force being applied to the tissue (referred to as the clamping position). As the anvil ramp surface 216 transitions to its substantially horizontally angled surface 220 (e.g., see FIGS. 8D and 9D), the upper knife tab 238 can slide within the upper knife channel 224 to drive the stapling and transection of the tissue.

Figure 18:
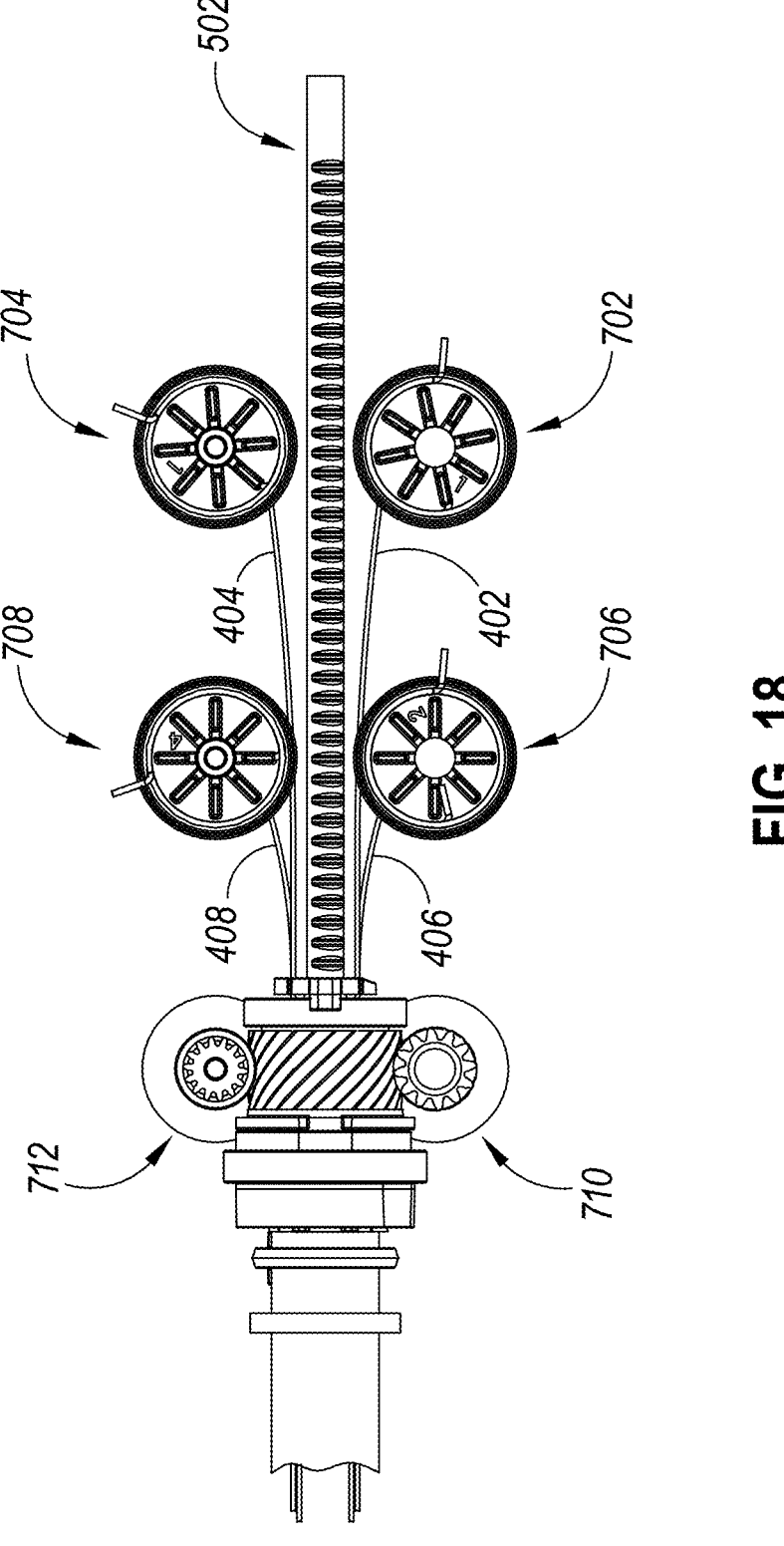
FIG. 18 is a top view of a proximal end of the surgical instrument of FIG. 1, depicting portions of the cable articulation subsystem, the knife firing subsystem, and the roll subsystem.
Figure 19:
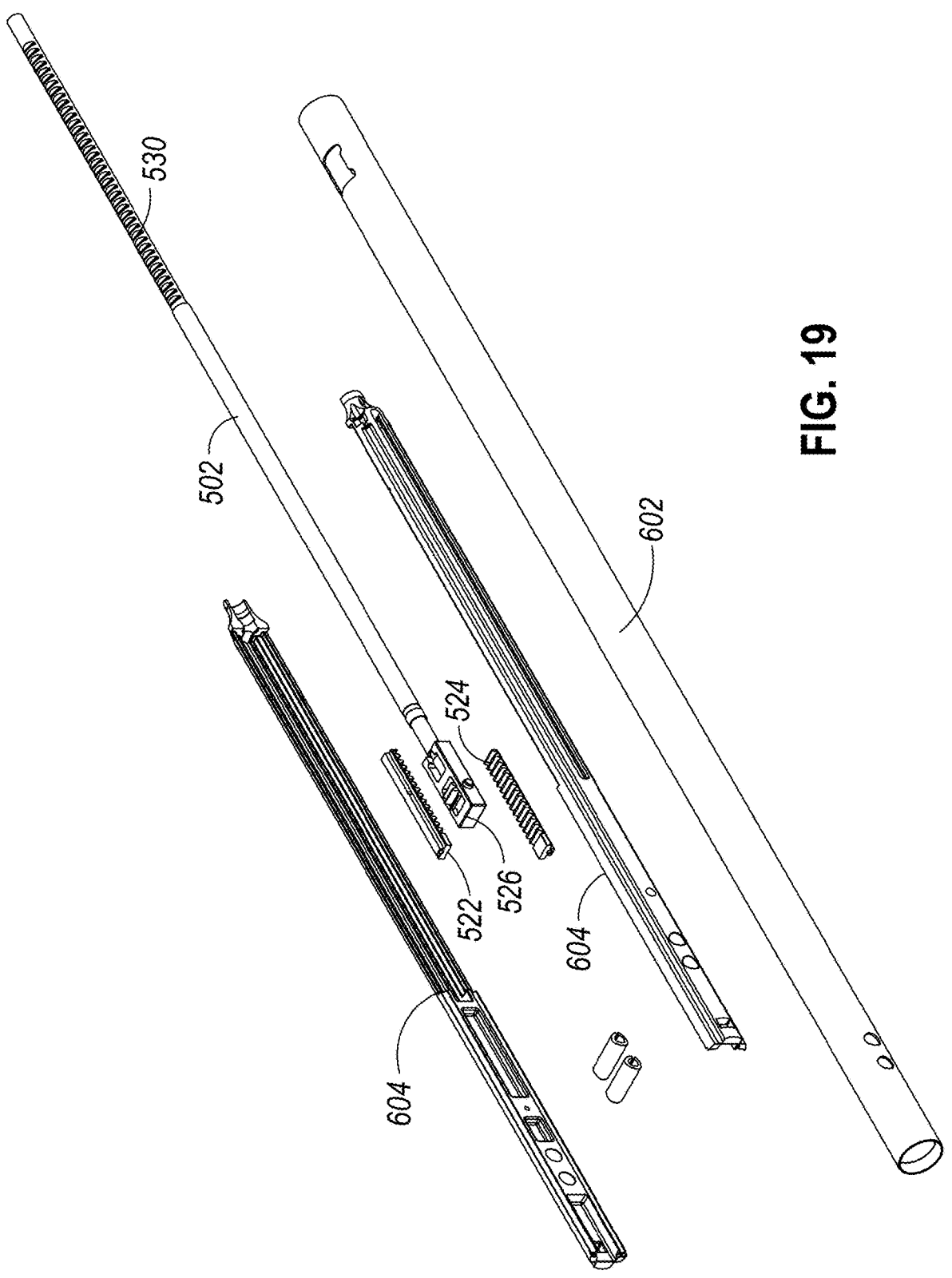
FIG. 19 is a perspective view of a shaft assembly, a differential, and a firing rod of the surgical instrument of FIG. 1.

As shown in FIG. 1, the surgical instrument 1000 further comprises a body exemplified as a housing 700 configured to engage a robotic platform (not shown). In other versions, the body may be configured as a handle configured to be gripped and manipulated by a clinician. As best shown in FIGS. 1 and 19, a shaft assembly 600A extends distally from the housing 700 and includes a rotatable outer shaft 602 and an inner shaft 604 arranged in two clamshell halves, with the outer shaft 602 being rotatably mounted to the housing 700 about a rotation joint (not shown), which may include one or more bearings. The inner shaft 604 is rotationally fixed to the outer shaft 602 and is configured such that articulation cables 402, 404, 406, 408 can be partially wound therearound without becoming tangled. As shown in FIG. 18, the housing 700 may house (1) a firing puck assembly 712 as part of the knife firing subsystem 500 operable to close the end effector 200, fire staples, and transect tissue, (2) a set of articulation puck assemblies 702, 704, 706, 708 as part of the articulation subsystem 400 operable to articulate the end effector 200 relative to the shaft assembly 600A, and (3) a shaft roll puck assembly 710 as part of the roll subsystem 600 configured to roll the outer shaft 602.

Referring to FIGS. 10-13, the articulation joint 300 comprises an array of joint discs 302 arranged longitudinally, and a center beam assembly 306 that cooperates with the joint discs 302 to provide articulation of the end effector 200 with at least two degrees of freedom (e.g., yaw and pitch), as described further below. Each joint disc 302 includes a central opening 304 that is configured to align coaxially with the central opening 304 of the other joint discs when the articulation joint 300 is in a straight, non-articulated state. The center beam assembly 306 extends longitudinally through the central openings 304 of joint discs 302 and applies a compressive axial force to the array of joints discs 302 to couple the joint discs 302 with one another. The joint discs 302 are nestably stacked with one another along the center beam assembly 306 such that longitudinally adjacent joint discs 302 movably interface with one another.

Figure 9B:
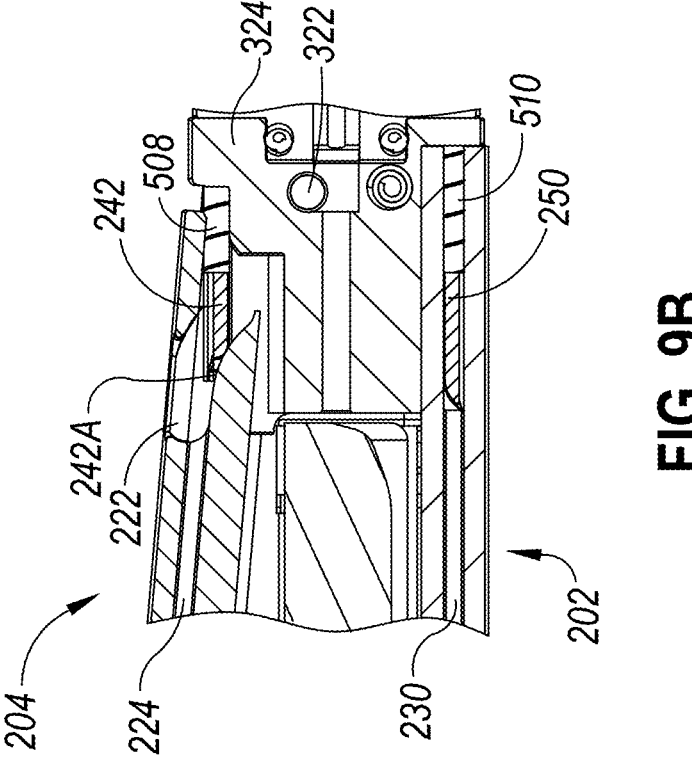
FIG. 9B is an enlarged side cross-sectional view of the proximal end portion of the end effector of the surgical instrument of FIG. 1, depicting the anvil in a grasping position with the knife partially advanced.
Figure 9A:
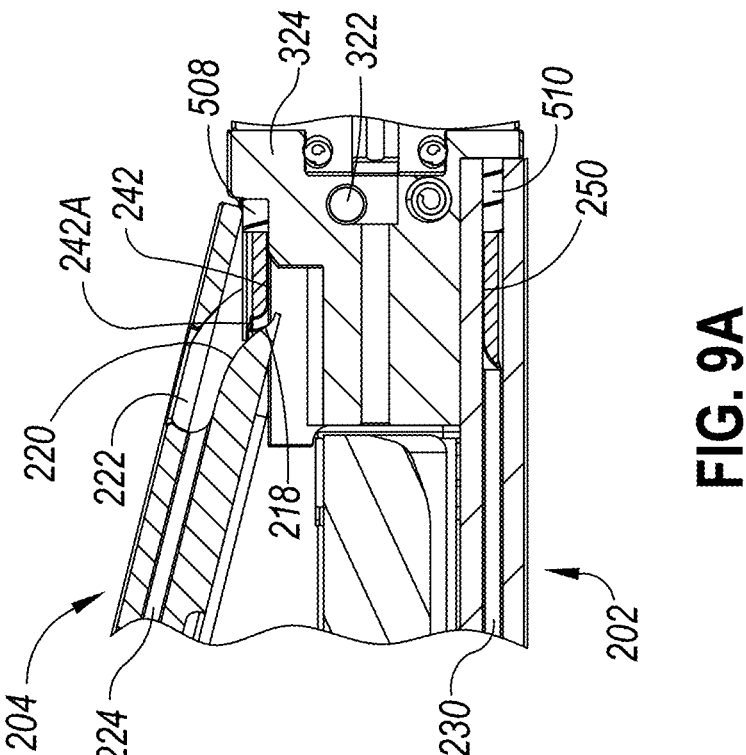
FIG. 9A is an enlarged side cross-sectional view of a proximal end portion of the end effector of the surgical instrument of FIG. 1, depicting the anvil in the open position.
Figure 9D:
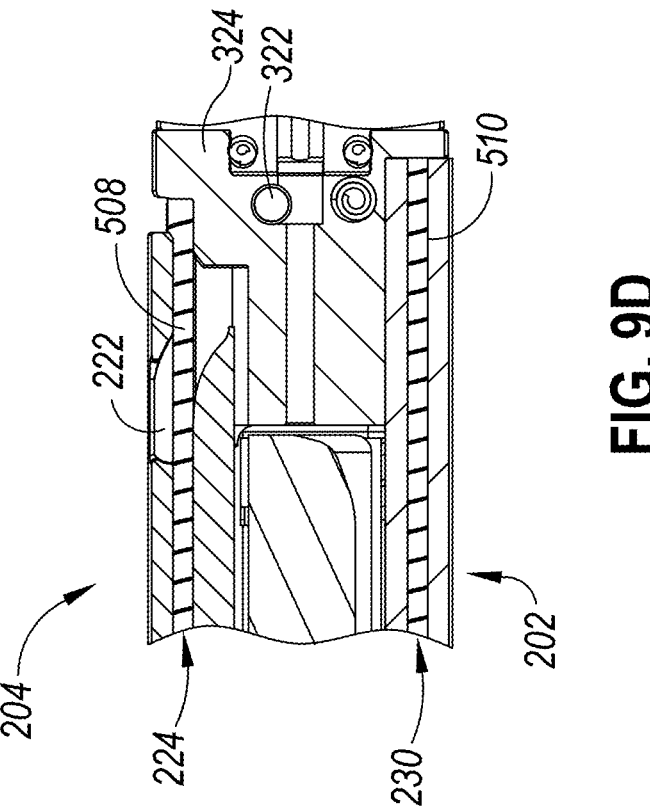
FIG. 9D is an enlarged side cross-sectional view of the proximal end portion of the end effector of the surgical instrument of FIG. 1, depicting the anvil in the clamping position with the knife fully advanced.
Figure 9C:
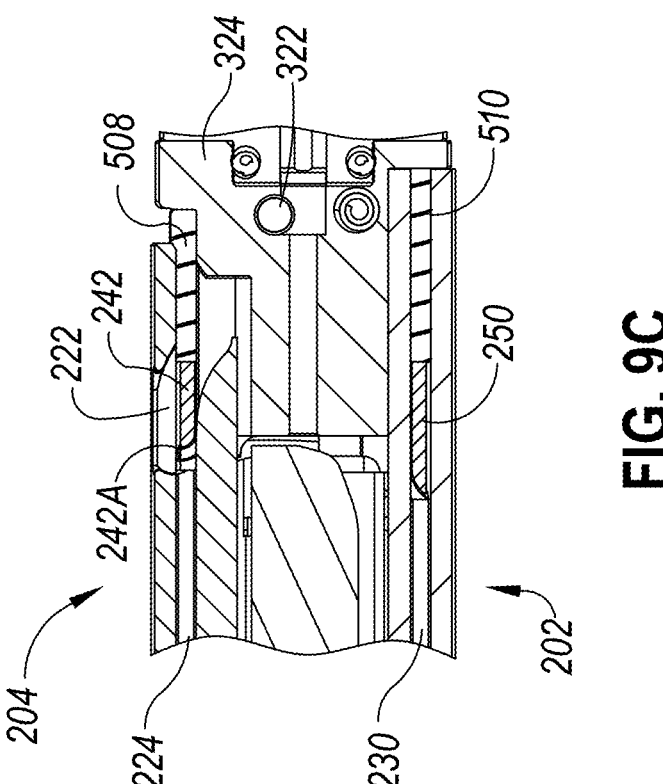
FIG. 9C is an enlarged side cross-sectional view of the proximal end portion of the end effector of the surgical instrument of FIG. 1, depicting the anvil in a clamping position with the knife partially advanced.
Figure 10:
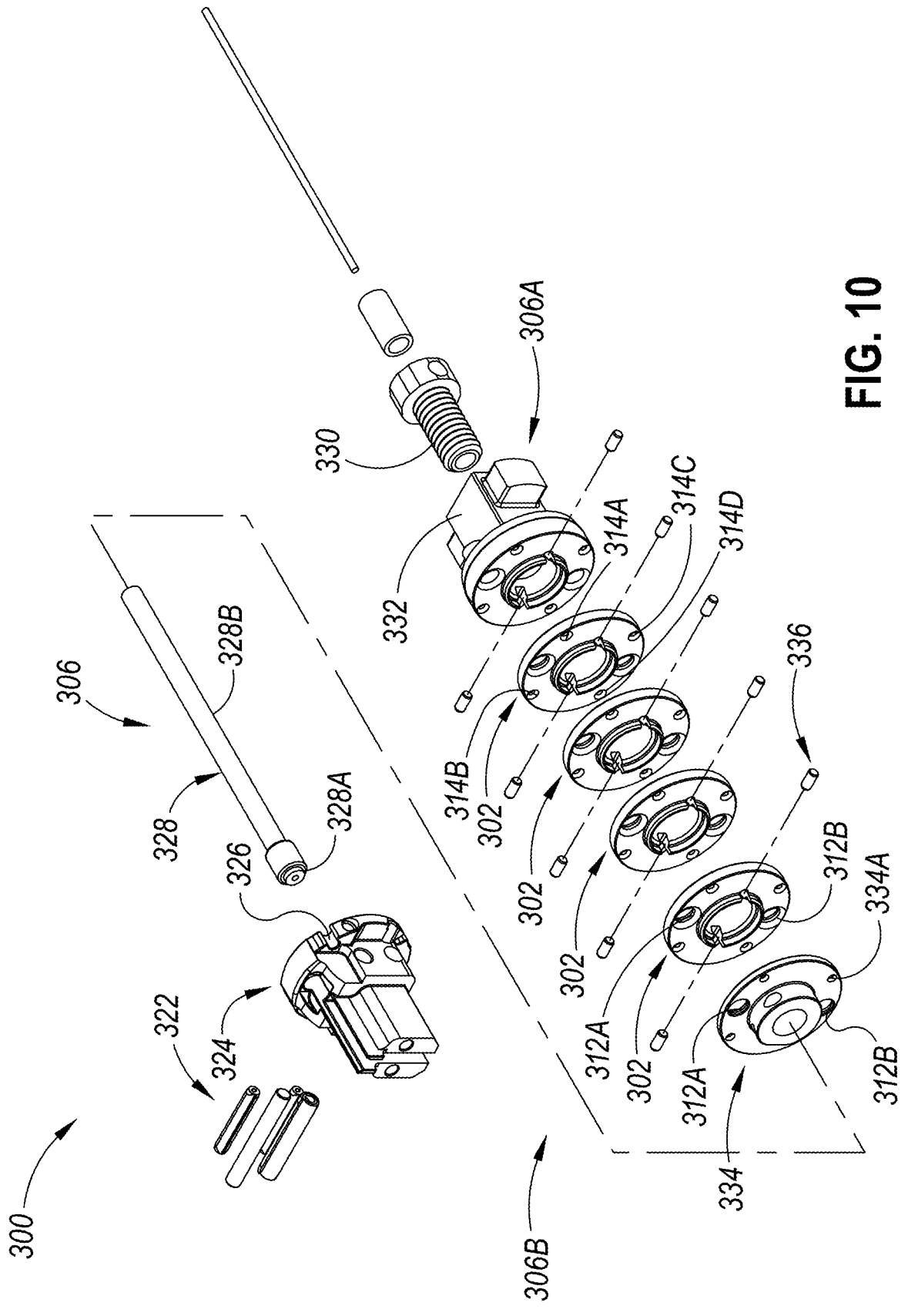
FIG. 10 is an exploded perspective view of the articulation joint of the surgical instrument of FIG. 1.
Figure 11:
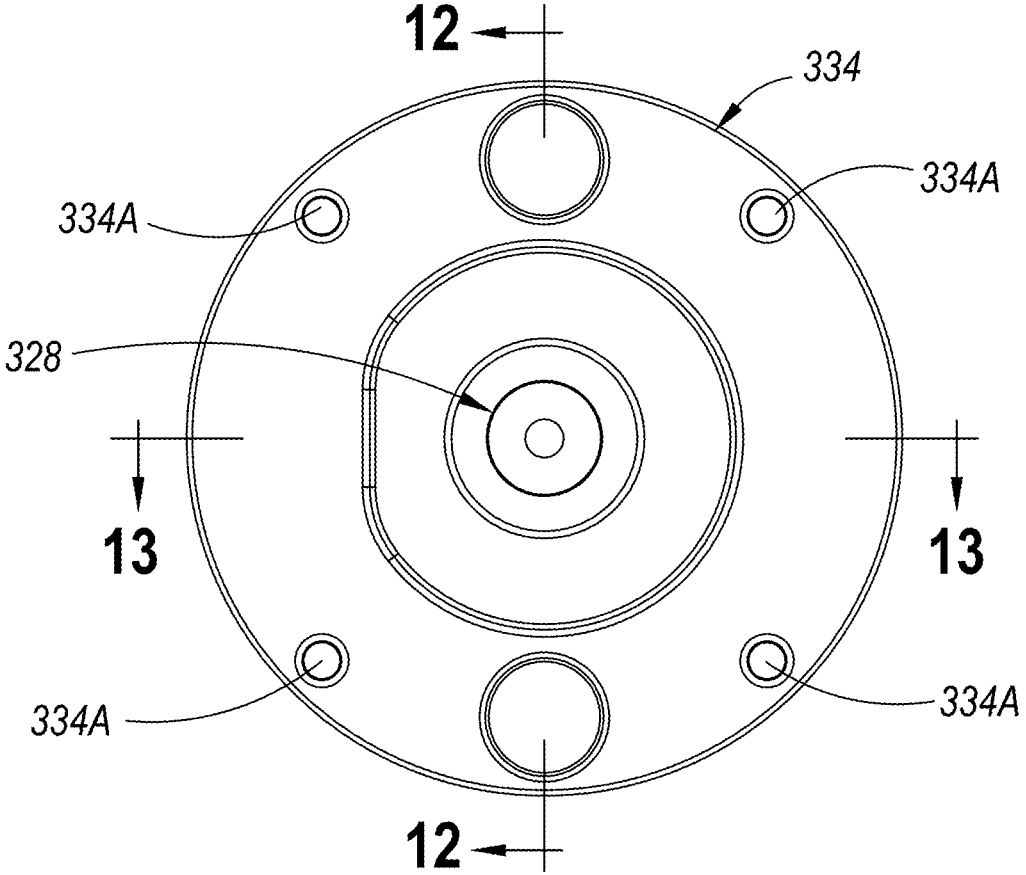
FIG. 11 is an end view of the articulation joint of FIG. 10.

As seen in FIGS. 9A-10, a distal end 306B of the center beam assembly 306 includes a distal retainer 324 that couples the distal end of the articulation joint 300 with a proximal end of the cartridge jaw 202 via one or more fasteners 322, thereby mechanically grounding and retaining the cartridge jaw 202 and thus the end effector 200 relative to the articulation joint 300. The distal retainer 324 includes a plurality of clearance pockets 326 that receive distal ends of articulation cables 402, 404, 406, 408. The distal end 306B further includes a distal retention disc 334 that defines a plurality of cable retention openings 334A. A proximal end 306A of the center beam assembly 306 includes a proximal retainer 332 that couples the proximal end of the articulation joint 300 with a distal end of the shaft assembly 600A.

Figure 12:
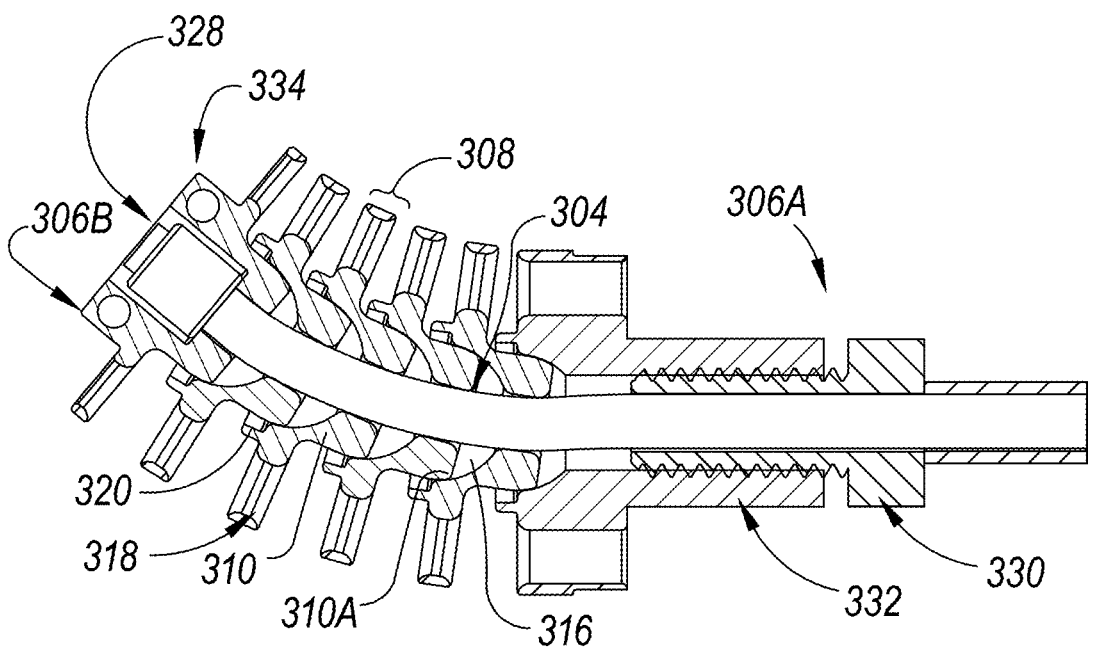
FIG. 12 is a cross-sectional view of a portion of the articulation joint of FIG. 10, taken along line 12-12 in FIG. 11.
Figure 13:
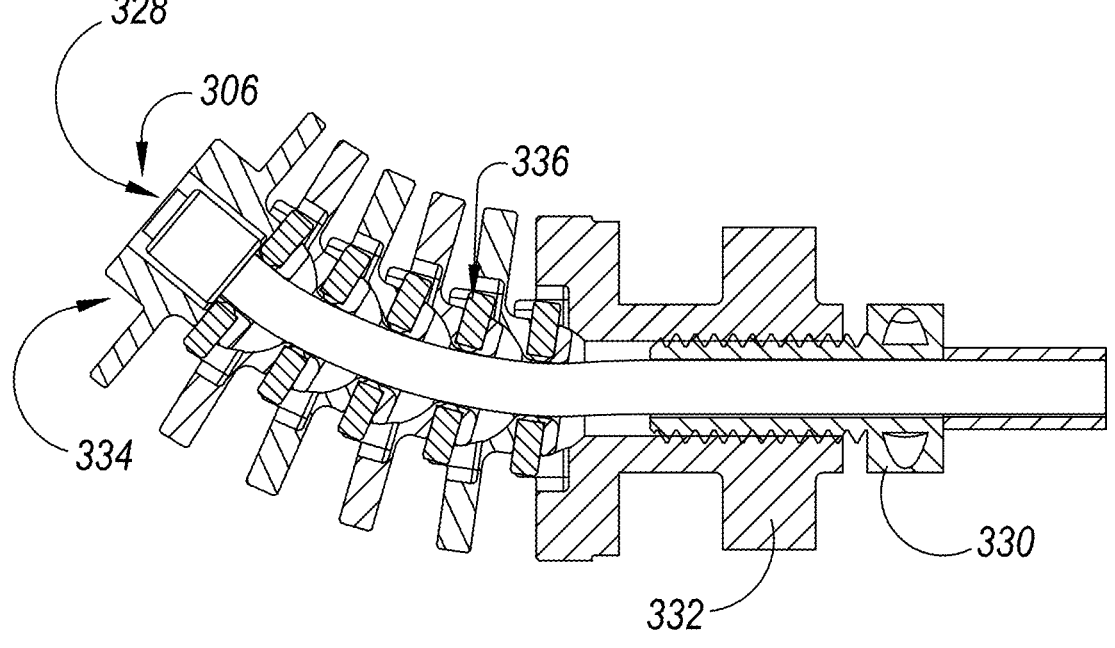
FIG. 13 is a cross-sectional view of a portion of the articulation joint of FIG. 10, taken along line 13-13 in FIG. 11.
Figure 14:
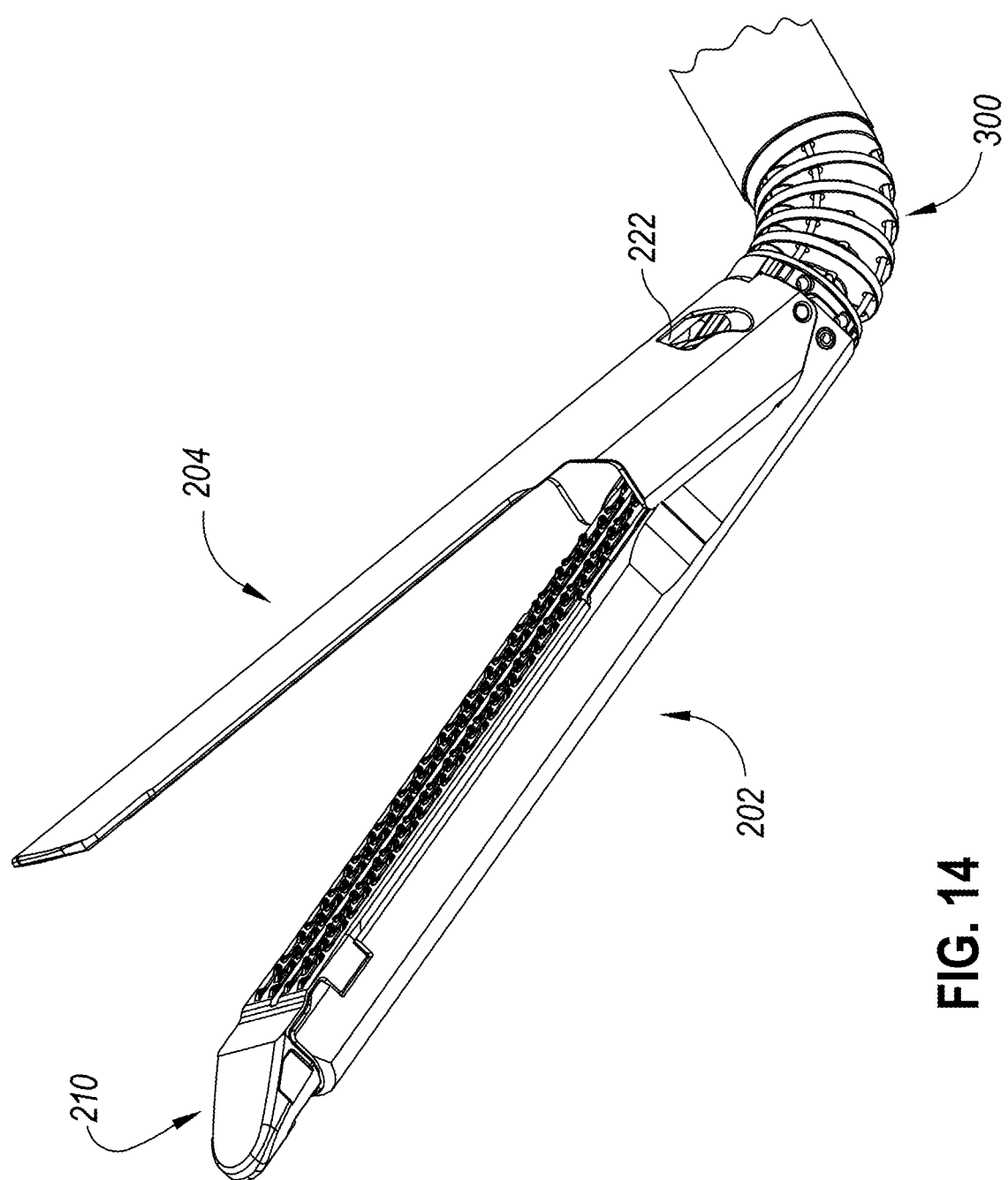
FIG. 14 is a perspective view of the distal end of the surgical instrument of FIG. 1, depicting the end effector articulated vertically and laterally with the anvil open.
Figure 15:
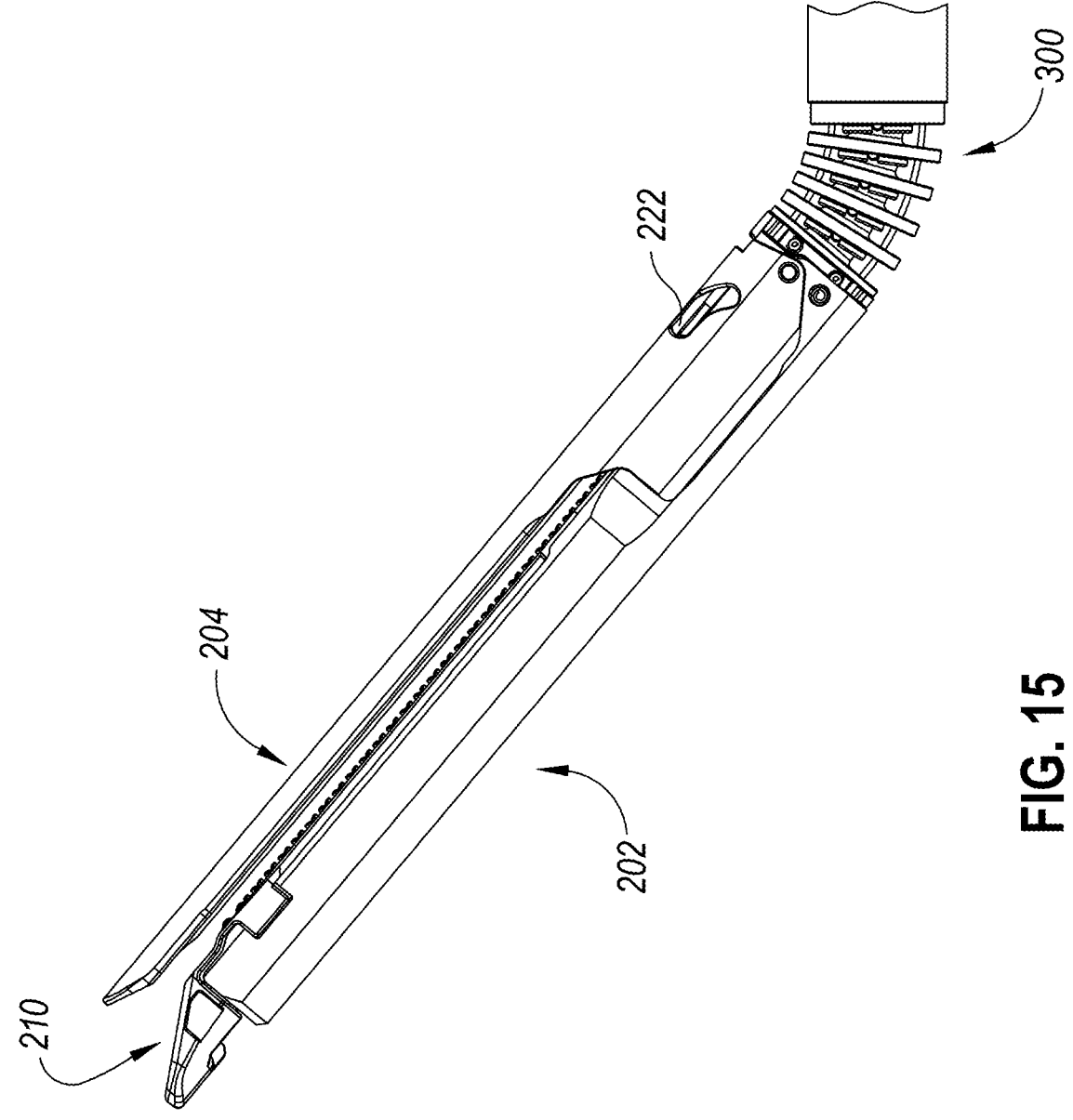
FIG. 15 is a side view of the distal end of the surgical instrument of FIG. 1, depicting the end effector articulated vertically with the anvil closed.
Figure 16:
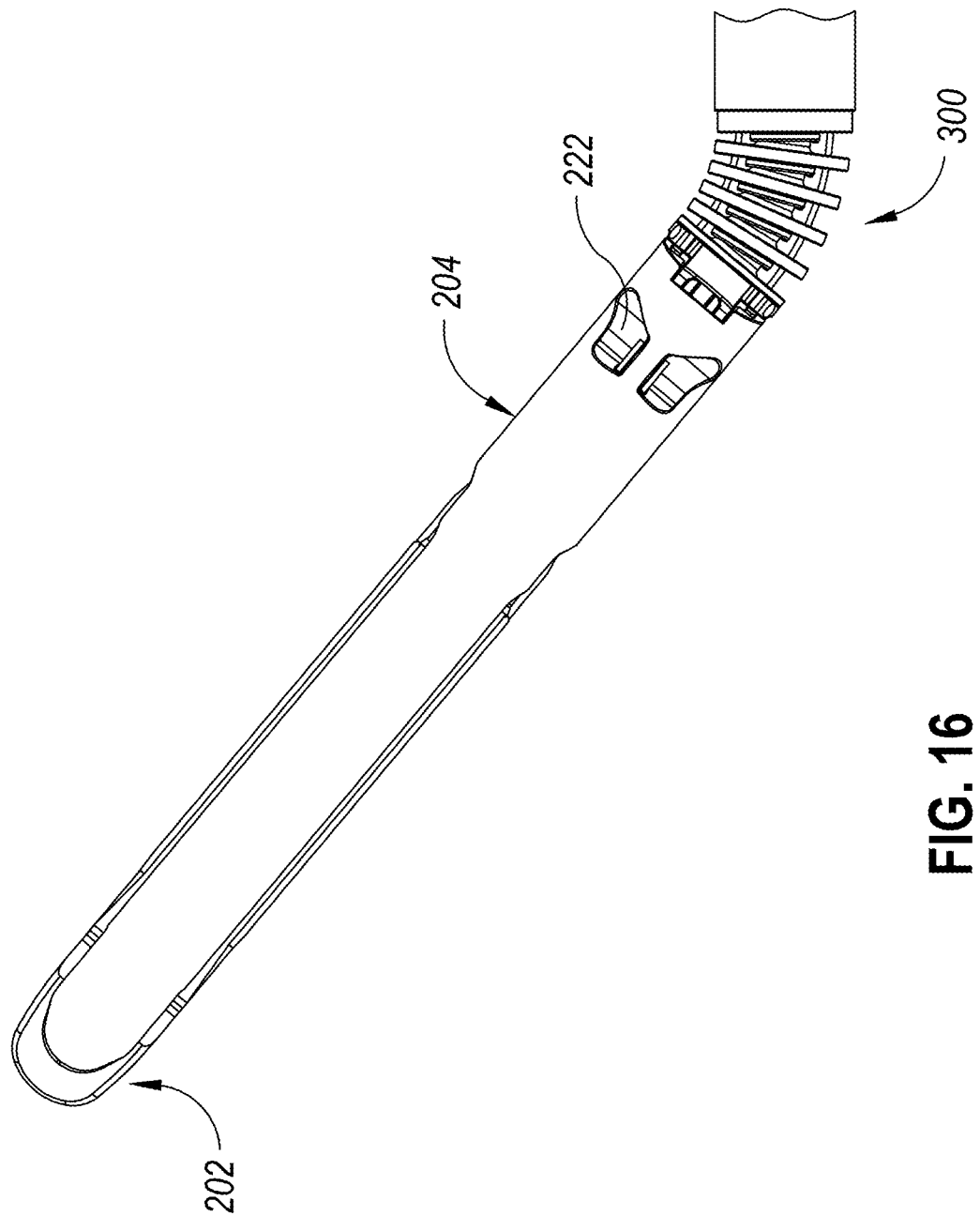
FIG. 16 is a top view of the distal end of the surgical instrument of FIG. 1, depicting the end effector articulated laterally with the anvil closed.

As shown particularly in FIGS. 10, 12, and 13, each joint disc 302 includes an articulation socket 308, an articulation pin 310 protruding outwardly from the articulation socket 308, a first push coil opening 312A defined through the articulation socket 308 and configured to receive a first push coil 508 therethrough, a second push coil opening 312B defined through the articulation socket 308 and configured to receive a second push coil 510 therethrough, and a plurality of articulation cable openings 314A-314D (e.g., a first articulation cable opening 314A, a second articulation cable opening 314B, a third articulation cable opening 314C, and a fourth articulation cable opening 314D) defined through the articulation socket 308 and configured to receive a respective articulation cable 402, 404, 406, 408 (e.g., a first articulation cable 402, a second articulation cable 404, a third articulation cable 406, and a fourth articulation cable 408) therethrough, and discussed in greater detail below. As shown in FIGS. 12 and 13, the central opening 304 is defined in the articulation pin 310 of each joint disc 302. In some versions, three articulation cable openings 314A, 314B, 314C are provided to correspond to three articulation cables 402, 404, 406, while in other versions, four articulation cable openings 314A, 314B, 314C, 314D are provided to correspond to four articulation cables 402, 404, 406, 408.

Each joint disc 302 further includes a rounded articulation pin proximal end 310A and a semi-spherical pin-receiving opening 316 defined in the articulation socket 308. As shown particularly in FIGS. 12 and 13, each rounded articulation pin proximal end 310A pivotally engages in an adjacent pin-receiving opening 316 of an adjacent joint disc 302, with the exception of a proximal-most end 310A that engages with the proximal retainer 332. The articulation pin proximal end 310A and pin-receiving opening 316 interface functions in a similar manner as a swivel bearing. Moreover, the articulation socket 308 includes a socket disc 318 and a pin retention socket 320. A pair of pins 336 are used to provide rotational coupling about a primary axis of the shaft assembly 600A from one disc 302 to the next. In other words, the pins constrain a rotational degree of freedom between adjacent joint discs 302 about the roll axis RA of the instrument 1000. In alternative versions, this feature can be integral to the joint disc 302.

The center beam assembly 306 further includes a center beam 328 that extends longitudinally through the central openings 304 of the joint discs 302. The center beam 328 includes a nitinol core 328A and a stainless-steel collar 328B wound over the nitinol core 328A that allows the center beam 328 to resiliently flex during deflection of the articulation joint 300. The wound stainless-steel collar 328B may have clockwise braiding and counterclockwise braiding to prevent unwinding thereof. The center beam assembly further includes a jack screw 330 that is threadably coupled with the proximal retainer 332 to adjust an axial compression force exerted by the center beam 328 on the array of joint discs 302, thereby enabling adjustment of a pre-load of the articulation joint 300.

The above-described articulation joint 300 forms a portion of the cable articulation subsystem 400 which allows for precise 360-degree movement of the end effector 200 about the articulation joint 300 with at least two degrees of freedom. In some versions, and as dictated by the roll subsystem 600 as well as a need to limit the amount of wrap of the articulation cables 402, 404, 406, 408, the articulation joint 300 is permitted about 320 degrees of roll within the overall system. The cable articulation subsystem 400 also includes a plurality of articulation cables 402, 404, 406, 408 each having a distal end 402A, 404A, 406A, 408A, coupled to the distal end 306B of the center beam assembly 306, and a proximal end 402B, 404B, 406B, 408B. More specifically, each distal end 402A, 404A, 406A, 408A can include a crimp that engages a cable retention opening 334A of the distal retention disc 334 to maintain its positioning. Each articulation cable is discretely manipulable to cause rotation of the articulation joint 300 and end effector 200 about at least one of a pitch axis PA and a yaw axis YA.

In some versions, three articulation cables may be provided rather than the four cables 402, 404, 406, 408 depicted herein. However, four articulation cables 402, 404, 406, 408 circumferentially spaced approximately ninety degrees from one another (as shown) provide load splitting. Additionally, in alternative versions, three and fourth articulation cable configurations may be spaced non-symmetrically relative to one another.

The shaft assembly 600A and housing 700 also form portions of the cable articulation subsystem 400. More specifically, each articulation cable 402, 404, 406, 408 extends from the articulation joint 300 and through the shaft assembly 600A to the housing 700. The proximal end 402B, 404B, 406B, 408B of each articulation cable (402, 404, 406) is movably mounted in the housing 700 which causes the above-mentioned rotation of the articulation joint 300 and end effector 200. The housing 700 includes articulation puck assemblies 702, 704, 706, 708 with rotatable capstans (not shown) about which corresponding proximal ends 402B, 404B, 406B, 408B of the articulation cables 402, 404, 406, 408 are windably mounted.

The articulation cables 402, 404, 406, 408 are routed through the shaft assembly 600A such that they are disposed between the outer shaft 602 and the inner shaft 604, with the articulation cables 402, 404, 406, 408 being able to partially wind therearound without becoming tangled. The inner shaft 604 also prevents the articulation cables 402, 404, 406, 408 from interfering with other components running down the center of the instrument 1000 (through the inner shaft 604).

The articulation cables 402, 404, 406, 408 are routed and coupled to the end effector 200 via the articulation joint 300 such that movement thereof in a proximal direction (via winding about the capstans of the housing 700) causes the end effector 200 to articulate in a predetermined manner via the articulation joint 300. For example, actuation of the first articulation cable 402 in the proximal direction causes articulation of the end effector 200 upwards and to the left, actuation of the second articulation cable 404 in the proximal direction causes rotation of the end effector 200 upwards and to the right, actuation of the third articulation cable 406 in the proximal direction causes rotation of the end effector 200 downwards and to the left, and actuation of the fourth articulation cable 408 in the proximal direction causes rotation of the end effector 200 downwards and to the right. Similarly, movement of two articulation cables simultaneously will result in blended articulation of the end effector 200. As will be appreciated by those skilled in the art, this configuration provides for the above-mentioned precise 360-degree articulation of the end effector 200 via the articulation joint 300 with at least two degrees of freedom and about 320 degrees of roll.

As shown throughout FIGS. 2, 4, 5, 8A-8D, 9A-9D, 17 and 19, the knife firing subsystem 500 includes the aforementioned knife 206, the aforementioned knife sled 236, a firing rod 502 that drives the knife 206 and/or knife sled 236, a first push rod 504, and a second push rod 506. The firing rod 502 includes a firing rod rack 530 and is driven by a firing puck assembly 712 of the housing 700. The first push rod 504 has a first push rod distal end 504A coupled to the knife sled 236 and a first push rod proximal end 504B coupled to the firing rod 502. Similarly, the second push rod has a second push rod distal end 506A coupled to the knife sled 236 and a second push rod proximal end 506B coupled to the firing rod 502. The distal ends 504A, 506A are coupled to respective upper and lower portions of the knife sled 236 (e.g., the upper knife tab 238 and the lower knife tab 246), which enables the knife 206 to be pushed evenly at its ends. In some versions, the proximal ends 504B, 506B of the push rods 504, 506 are coupled to the firing rod 502 via a differential 520.

The knife firing subsystem 500 is configured in a manner to enable articulation of the end effector 200 while still enabling proper functionality of the knife 206. To that end, the first push rod 504 includes a first flexible section in the form of a first push coil 508 and the second push rod 506 comprises a second flexible section in the form of a second push coil 510. The push coils 508, 510 route through the articulation joint 300 via the respective push coil openings 312A, 312B, and the push rods 504, 506 engage the respective tab openings 244, 252 in the knife sled 236. A first center cable 512 extends through the first push coil 508 to engage the knife sled 236 via a barrel crimp, and a second center cable 514 extends through the second push coil 510 to engage the knife sled 236 via a barrel crimp. The push coils 508, 510 provide the push rods 504, 506 sufficient stability to deliver an axial firing force to the knife 206, while not being too stiff that would prevent articulation at the joint 300. The cables 512, 514, which are engaged with the knife sled 236 as discussed above (see, e.g., FIG. 8A), prevent the push coils 508, 510 from stretching and/or elongating and serve as retraction cables when the rods 504, 506 are retracted towards the proximal end of the surgical instrument 1000. The entirety of each push rod 504, 506 does not extend through the articulation joint 300, and therefore does not need to be flexible. Accordingly, a proximal section of each push rod 504, 506 can be less flexible than the push coils 508, 510.

II. Illustrative End Effectors with Staple Cartridge Retainer and Staple Cartridge Datum Locator As mentioned above, after anvil jaw 204 and staple cartridge 210 suitably compress and clamp tissue during illustrative use, surgical instrument 1000 may be fired so that the knife 206 advances distally through the staple cartridge 210 to both cut the clamped tissue and simultaneously drive an array of staples into the clamped tissue in accordance with the description herein. In the current example, in order to staple tissue, the staples housed within the staple cartridge 210 are driven out of a respective staple opening defined by staple cartridge 210 into the clamped tissue and against a designated staple forming pocket defined by anvil jaw 204. In particular, legs of each staple in the array of staples are actuated against the designated staple forming pocket defined by anvil jaw 204 in order to suitably bend staple legs from a substantially U-shaped configuration (e.g., a pre-fired staple, etc.) into a suitable B-shaped configuration (e.g., a fired staple, etc.), thereby allowing legs of fired staples to suitably engage and compress tissue.

As also mentioned above, staple cartridge 210 is retained by cartridge jaw 202. After staple cartridge 210 has been fired in accordance with the description herein, staple cartridge 210 (i.e., a spent staple cartridge 210) may be decoupled from cartridge jaw 202. Subsequently, a new (e.g., unspent, unused, etc.) staple cartridge 210 may be suitably loaded onto cartridge jaw 202 in replacement of the spent staple cartridge 210 such that end effector 200 may be used again in accordance with the description herein.

Figures 8C, 8D:
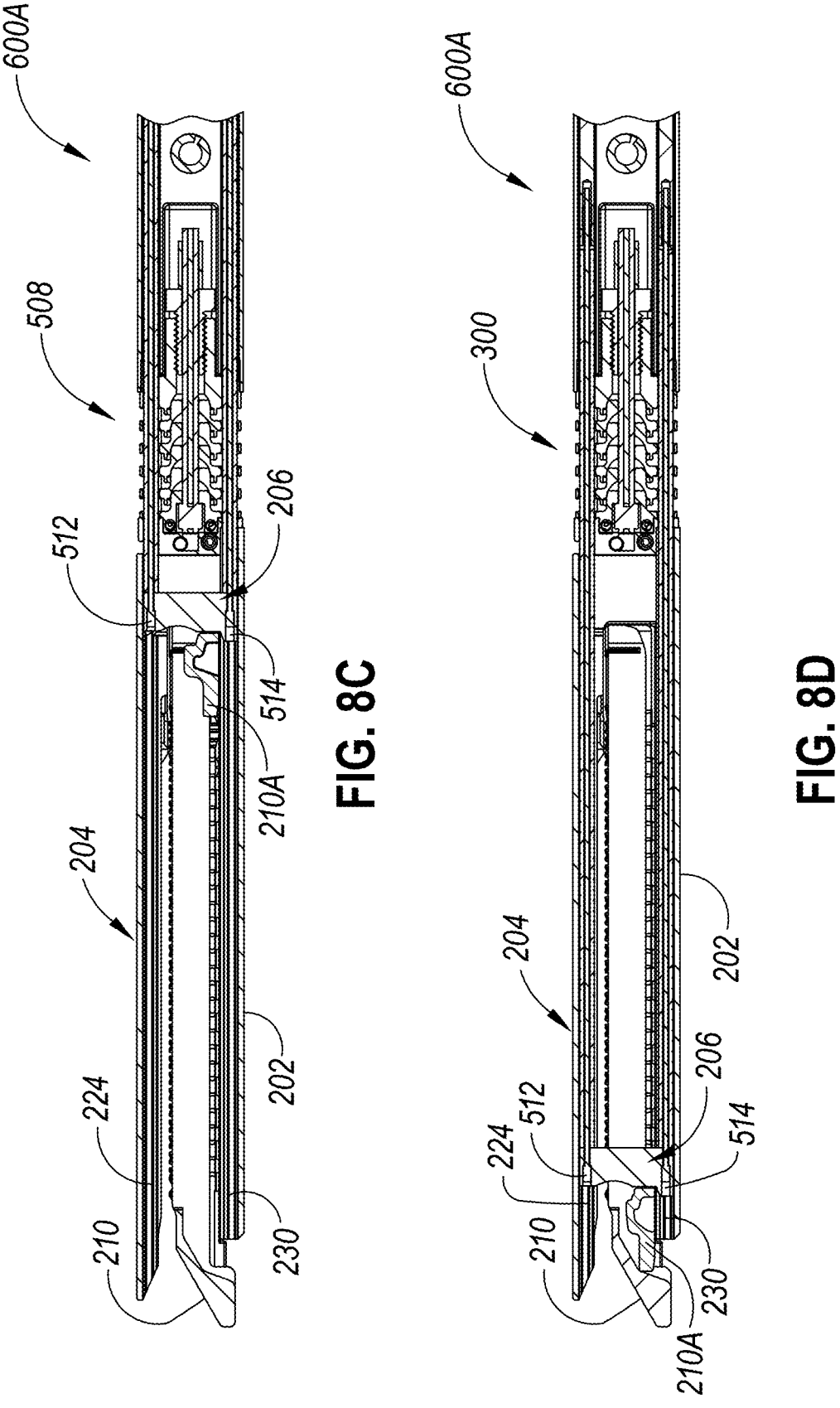
FIG. 8C is a side cross-sectional view of the distal end portion of the surgical instrument of FIG. 1, depicting the anvil in a clamping position with the knife partially advanced.
FIG. 8D is a side cross-sectional view of the distal end portion of the surgical instrument of FIG. 1, depicting the anvil in the clamping position with the knife fully advanced.

In order to promote a quality staple formation (e.g., a fired staple that suitable engages and compresses tissue), it may be desirable to ensure that staple forming pockets defined by anvil jaw 204 are consistently and accurately aligned with their respective pre-fired staple housed within staple cartridge 210 (as well as staple cartridge 210 itself) while jaws 202, 204 are in the closed position (see FIGS. 8C-8D). Such alignment between staple forming pockets of anvil jaw 204 and staples within staple cartridge 210 may be vertical, lateral, longitudinal, etc. Since multiple staple cartridges 210 are intended to be used in conjunction with jaws 202, 204 of end effector 200, it may be desirable to provide various features that inhibit a staple cartridge 210 from inadvertently disassociating with cartridge jaw 202 during illustrative use while also suitably aligning staple cartridge 210 with staple forming pockets defined by anvil jaw 204 prior to firing staples out of staple cartridge 210. Additionally, it may be desirable to provide such features while also providing the ability to easily couple and decouple staple cartridge 210 to/from cartridge jaw 202.

FIGS. 20A-21 and FIGS. 25A-25C show an illustrative end effector 1200 that may be readily incorporated into instrument 1000 in replacement of end effector 200 described above. Therefore, end effector 1200 may be substantially similar to end effector 200 described above, with differences elaborated herein. End effector 1200 includes a cartridge jaw 1202, an anvil jaw 1204, a replaceable staple cartridge 1210, a knife sled 1236, and a knife 1206; which may be substantially similar to cartridge jaw 202, anvil jaw 204, staple cartridge 210, knife sled 236, and knife 206 described above, respectively, with differences elaborated herein.

Figure 20A:
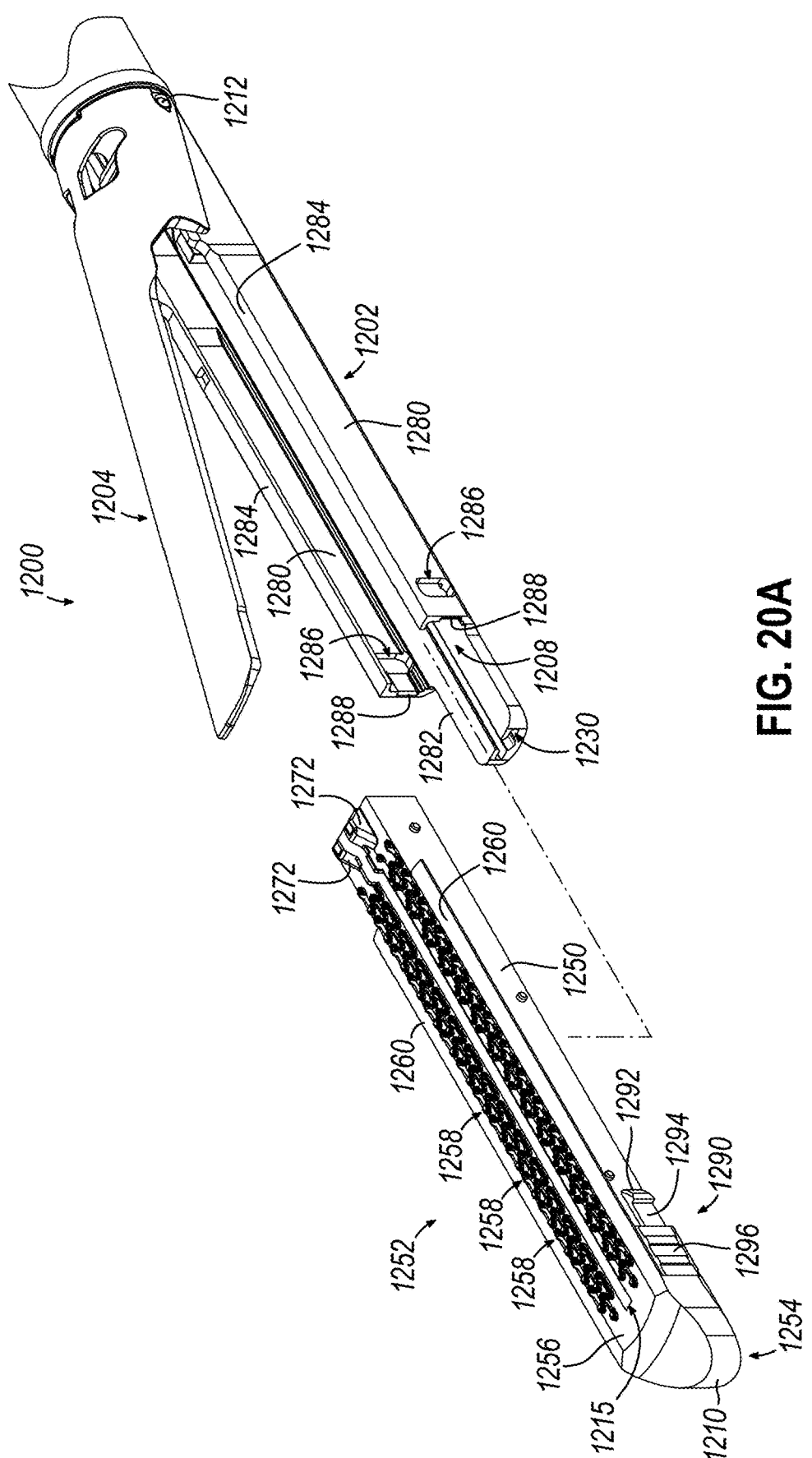
FIG. 20A is a perspective view of an alternative end effector including a cartridge jaw, an anvil jaw, and a replaceable staple cartridge, where the cartridge jaw and the anvil jaw are in an open position where the replaceable staple cartridge is decoupled from the cartridge jaw.
Figure 20B:
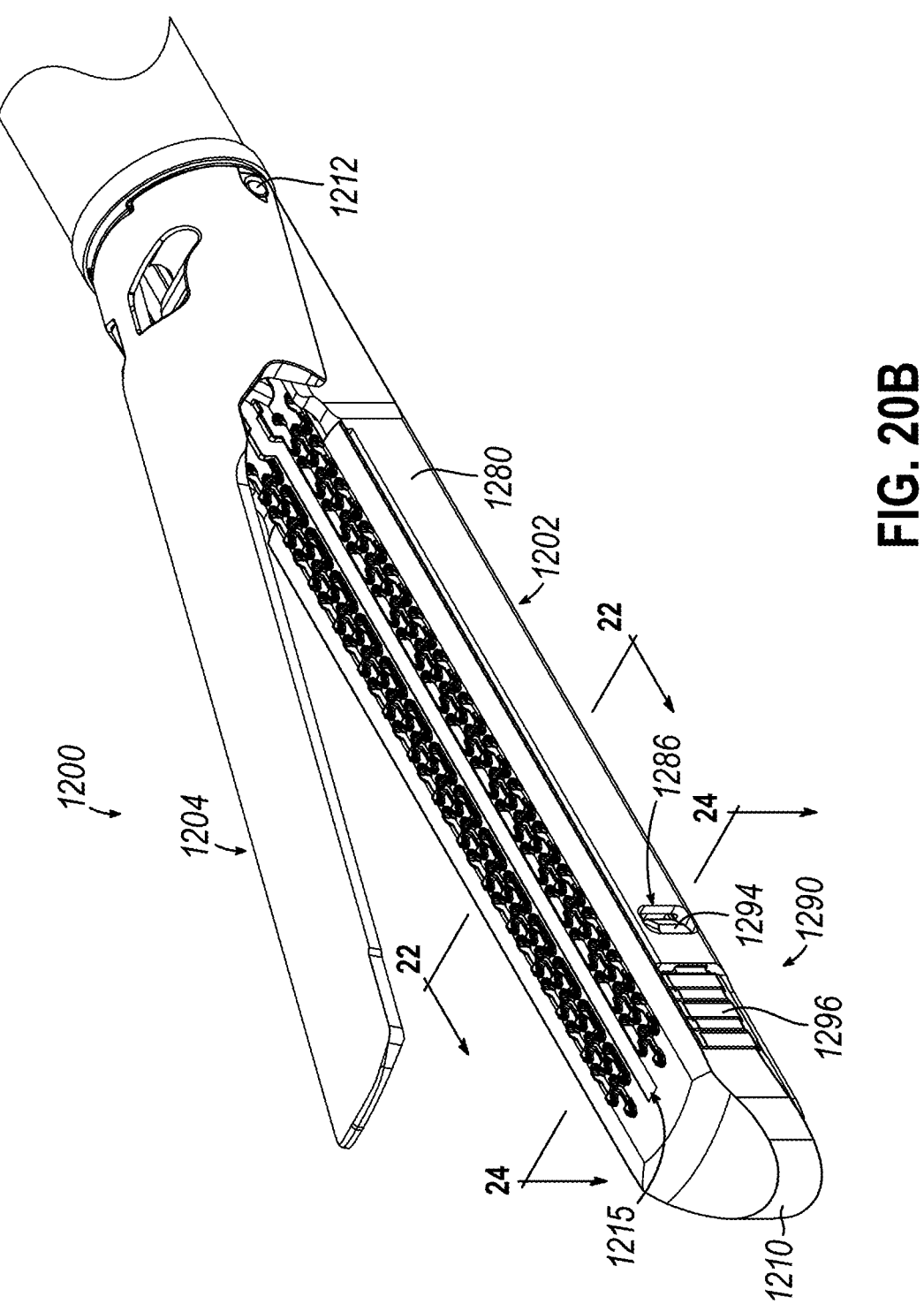
FIG. 20B is a perspective view of the end effector of FIG. 20A, with the replaceable staple cartridge coupled to the cartridge jaw.

As shown between FIGS. 20A-20B, replaceable staple cartridge 1210 is configured to selectively couple and decouple with cartridge jaw 1202. As will be described in greater detail below, staple cartridge 1210 includes at least one staple cartridge retainer 1290 configured to engage and/or interface with cartridge jaw 1202 such that that staple cartridge 1210 does not inadvertently disassociate with cartridge jaw 1202 during illustrative use. Further, staple cartridge retainer(s) 1290 may be utilized in order to quickly and easily decouple a spent staple cartridge 1210 from cartridge jaw 1202.

As will also be described in greater detail below, staple cartridge 1210 and anvil jaw 1204 together form a staple cartridge datum locator 1270 that is configured to consistently locate/align staple cartridge 1210 relative to anvil jaw 1204 in response to anvil jaw 1204 pivoting into the closed position (see FIG. 25C). Alignment provided by staple cartridge datum locator 1270 is configured to align staples 1255 (see FIG. 22) housed within staple cartridge 1210 with their respective staple forming pocket 1205 (see FIG. 21) of anvil jaw 1204.

Cartridge jaw 1202 and anvil jaw 1204 are pivotally coupled to each other via a pivot pin 1212. Cartridge jaw 1202 defines a longitudinally extending lower knife channel 1230, which may be substantially similar to lower knife channel 230 described above. Anvil jaw 1204 defines a longitudinally extending upper knife channel 1224 (see FIG. 21), which may be substantially similar to upper knife channel 224 described above. Upper knife channel 1224 also includes a ramp surface 1216 (see FIGS. 25A-25B), which may be substantially similar to ramp surface 216 described above.

Knife sled 1236 includes an upper knife tab 1238 and a lower knife tab 1246 which are configured to actuate within longitudinally extending upper knife channel 1224 and lower knife channel 1230, respectively. Upper knife tab 1238 and lower knife tab 1246 may be substantially similar to upper knife tab 238 and lower knife tab 246 described above, respectively, with differences elaborated herein. Therefore, upper knife tab 1238 may engage or otherwise contact ramp surface 1216 as knife sled 1236 actuates distally from a proximal position in order to pivot jaws 1202, 1204 relative to each other from an open position (see FIGS. 20B and 25A) into a closed position (see FIG. 25C). End effector 1200 may include one or more biasing springs (not shown) that is substantially similar to biasing springs 214 described above to thereby urge jaws 1202, 1204 toward the open position. Therefore, knife firing subsystem 500 described above may be utilized in conjunction with knife sled 1236 in order to pivot jaws 1202, 1204 relative to each other to grasp and release tissue in a substantially similar manner to end effector 200 described above.

Similar to knife 206 and knife sled 236 described above, knife 1206 and knife sled 1236 are coupled to each other and configured to actuate through suitable portions of cartridge jaw, 1202, anvil jaw 1204, and staple cartridge 1210 in order to simultaneously staple and sever tissue clamped between jaws 1202, 1204 in accordance with the description herein.

Cartridge channel 1202 includes a pair of lateral sidewalls 1280, and a base 1282 extending laterally between sidewalls 1280. Lateral sidewalls 1280 and base 1282 together define elongated channel 1208 that is dimensioned to receive staple cartridge 1210 in accordance with the description herein. Base 1282 defines lower knife channel 1230 dimensioned to slidably house lower knife tab 1246. In the current example, a distal portion of base 1282 extends distally relive to a distal end of lateral sidewalls 1280. Additionally, an upper end of each lateral sidewall 1280 includes a projection 1284 that extends laterally inward. As will be described in greater detail below, projections 1284 are configured to fit within a vertical alignment slot 1266 (see FIG. 22) defined by staple cartridge 1210 in order to vertically retain staple cartridge 1210 within cartridge channel 1202, as well as promote vertical alignment of staple cartridge 1210 relative to cartridge jaw 1202.

Lateral sidewalls 1280 also define a through hole 1286 extending from an interior surface of a respective sidewall 1280 to an exterior surface of the respective sidewall 1280. Through holes 1286 are located along a distal portion of lateral sidewalls 1280. Additionally, an interior surface of each lateral sidewall 1280 defines a recessed pocket 1288 starting at a distal end of the respective lateral sidewall 1280 and extending into a respective through hole 1286. As will be described in greater detail below, through holes 1286 and recessed pockets 1288 are dimensioned to selectively receive a respective staple cartridge retainer 1290 of staple cartridge 1210 in order to selectively couple staple cartridge 1210 with cartridge jaw 1202 such that that staple cartridge 1210 does not inadvertently disassociate with cartridge jaw 1202 during illustrative use.

Figure 21:
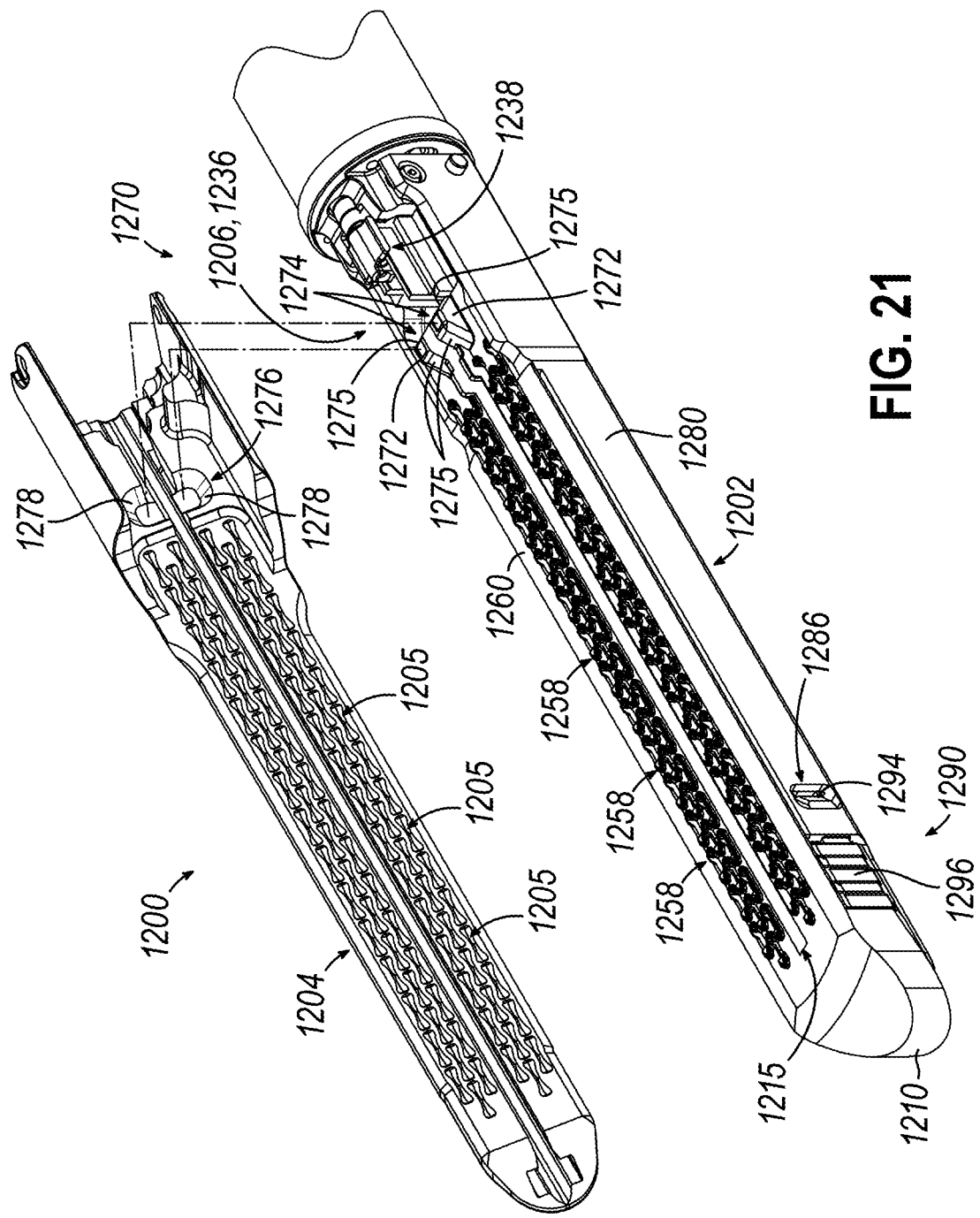
FIG. 21 is an exploded perspective view of the end effector of FIG. 20A.

Turning to FIG. 21, an underside of anvil jaw 1204 defines a plurality of staple forming pockets 1205. When staple cartridge 1210 is suitably loaded on cartridge jaw 1202 and jaws 1202,1204 are pivoted toward the closed position in accordance with the description herein, staple forming pockets 1205 of anvil jaw 1204 are suitably aligned with their respective staple opening 1258. Staple forming pockets 1205 are configured to engage the legs of a respective staple 1255 (see FIG. 22) fired out of staple cartridge 1210 in order to suitably form a B-shaped fired staple.

Further, a proximal portion of the underside of anvil jaw 1204 includes slanted engagement surface 1278 that at least partially defines a complementary cavity 1276 of staple cartridge datum locator 1270. As will be described in greater detail below, slanted engagement surface 1278 is configured to engage upward extending protrusions 1272 associated with staple cartridge 1210 in response to jaws 1202, 1204 pivoting into the closed position, where such engagement between slanted engagement surface 1278 and upward extending protrusions 1272 is configured to locate/align staple cartridge 1210 relative to anvil 1204 at a predetermined datum.

As mentioned above, replaceable staple cartridge 1210 is configured to selectively couple and decouple with cartridge jaw 1202. Therefore, an unspent staple cartridge 1210 may be readily loaded onto cartridge jaw 1202, fired in accordance with the description herein, and subsequently removed from cartridge jaw 1201 in accordance with the description herein. Staple cartridge 1210 includes a cartridge body 1250 that extends between a proximal portion 1252 and a distal portion 1254. Cartridge body 1250 includes a staple deck 1256 that defines a plurality of staple openings 1258, each housing a respective staple 1255 (see FIG. 22). Staple cartridge 1210 includes a cartridge sled (not shown) which may be substantially similar to cartridge sled 210A described above.

Figure 22:
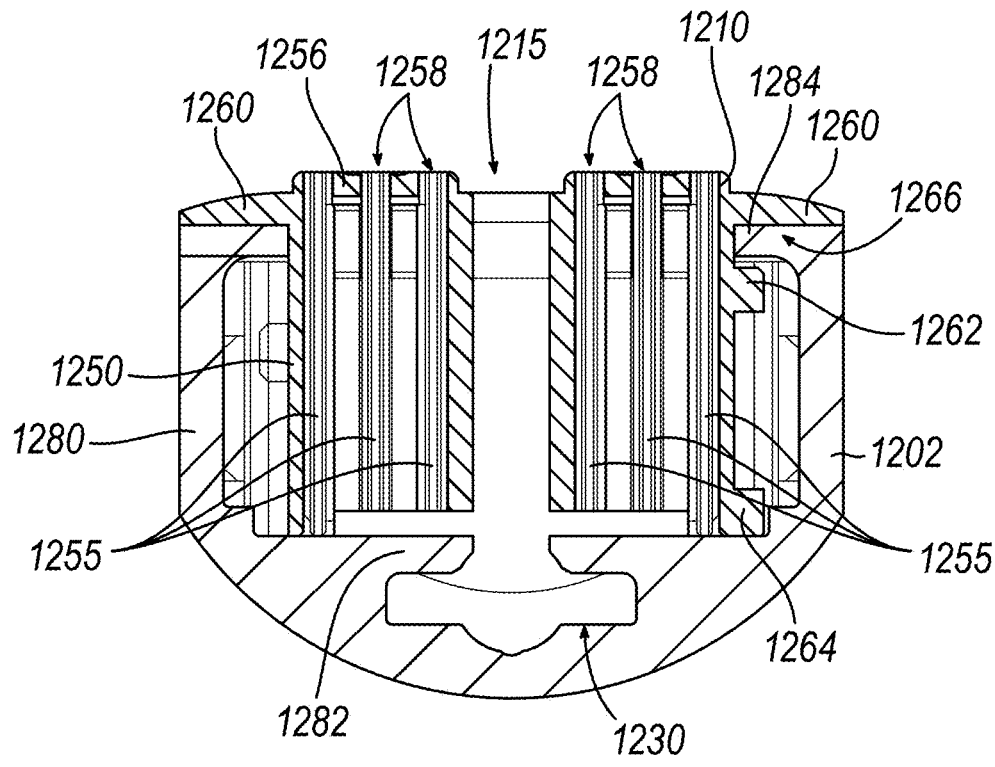
FIG. 22 is a cross-sectional view of the cartridge jaw and the replaceable staple cartridge of FIG. 20A, taken along line 22-22 of FIG. 20B.
Figure 23:
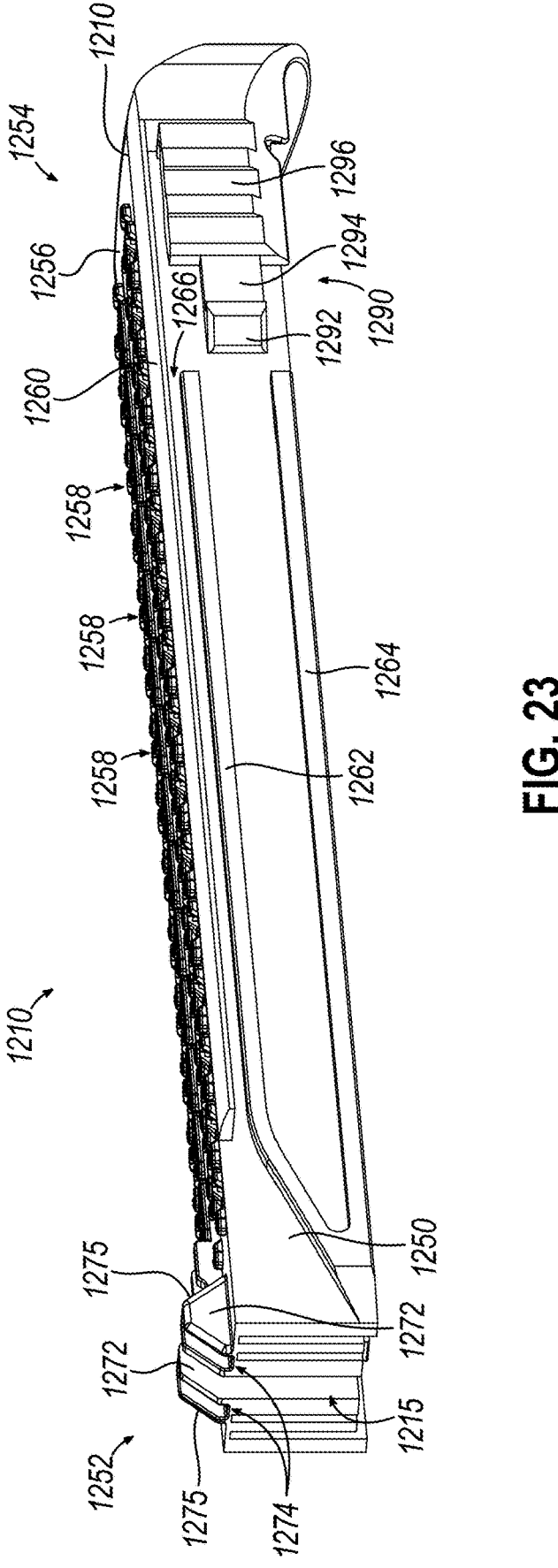
FIG. 23 is a perspective view of the replaceable staple cartridge of FIG. 20A.

Further, cartridge body 1250 includes a pair of staple deck rails 1260, a first lateral rail 1262 (see FIG. 23), and a second lateral rail 1264 (see FIG. 23). Staple deck rails 1260 extend laterally outward from staple deck 1256. First lateral rail 1262 and second lateral rail 1264 extend laterally outward from a side portion of cartridge body 1250. As shown in FIG. 22, second lateral rail 1264 may rest on an interior surface of base 1282, while staple deck rails 1260 may rest on top of a respective projection 1284 of lateral sidewalls 1280.

As also shown in FIG. 22, a staple deck rail 1260 and first lateral rail 1262 define a vertical alignment slot 1266. Vertical alignment slot 1266 is configured to receive a projection 1284 of lateral sidewall 1280. First lateral rail 1262 may engage the underside of projection 1284 in order to vertically restrain staple cartridge body 1250 relative to cartridge jaw 1202 when suitable coupled together. Therefore, first lateral rail 1262 and projection 1284 may be utilized in order to vertically retain staple cartridge 1210 within cartridge jaw 1202.

Due to the interaction between projection 1284 and vertical alignment slot 1266, staple cartridge 1210 may be coupled and decoupled with cartridge jaw 1202 by vertically and laterally aligning a proximal end of cartridge body 1250 with the distal end of cartridge jaw 1202 (as shown in FIG. 20A), and then moving the cartridge body 1250 and/or cartridge jaw 1202 in a longitudinal direction toward each other until staple cartridge 1210 is suitably coupled to cartridge jaw 1202 in accordance with the description herein.

As mentioned above, staple cartridge 1210 also includes at least one staple cartridge retainer 1290 configured to engage and/or interface with cartridge jaw 1202 such that staple cartridge 1210 does not inadvertently disassociate with cartridge jaw 1202 during illustrative use in accordance with the description herein. As will also be described in greater detail below, staple cartridge retainer(s) 1290 initially locate staple cartridge 1210 within an acceptable range relative to jaw 1202 such that features of staple cartridge datum locator 1270 associated with anvil jaw 1204 and staple cartridge 1210 may suitably engage each other when jaws 1202, 1204 pivot toward the closed position.

Staple cartridge retainers 1290 are located along distal portion 1254 of cartridge body 1250. In the current example, two staple cartridge retainers 1290 are utilized, each located on a respective lateral side of cartridge body 1250. However, it should be understood that any suitable number of staple cartridge retainers 1290 may be utilized as would be apparent to one skilled in the art in view of the teachings herein, such as one or three staple cartridge retainers 1290. Further, while staple cartridge retainers 1290 of the current example are located on lateral sides of cartridge body 1250, it should be readily understood that staple cartridge retainers 1290 may be located at any other suitable location to engage/ interface suitable portions of cartridge jaw 1202 as would be apparent to one skilled in the art in view of the teachings herein.

Figure 24:
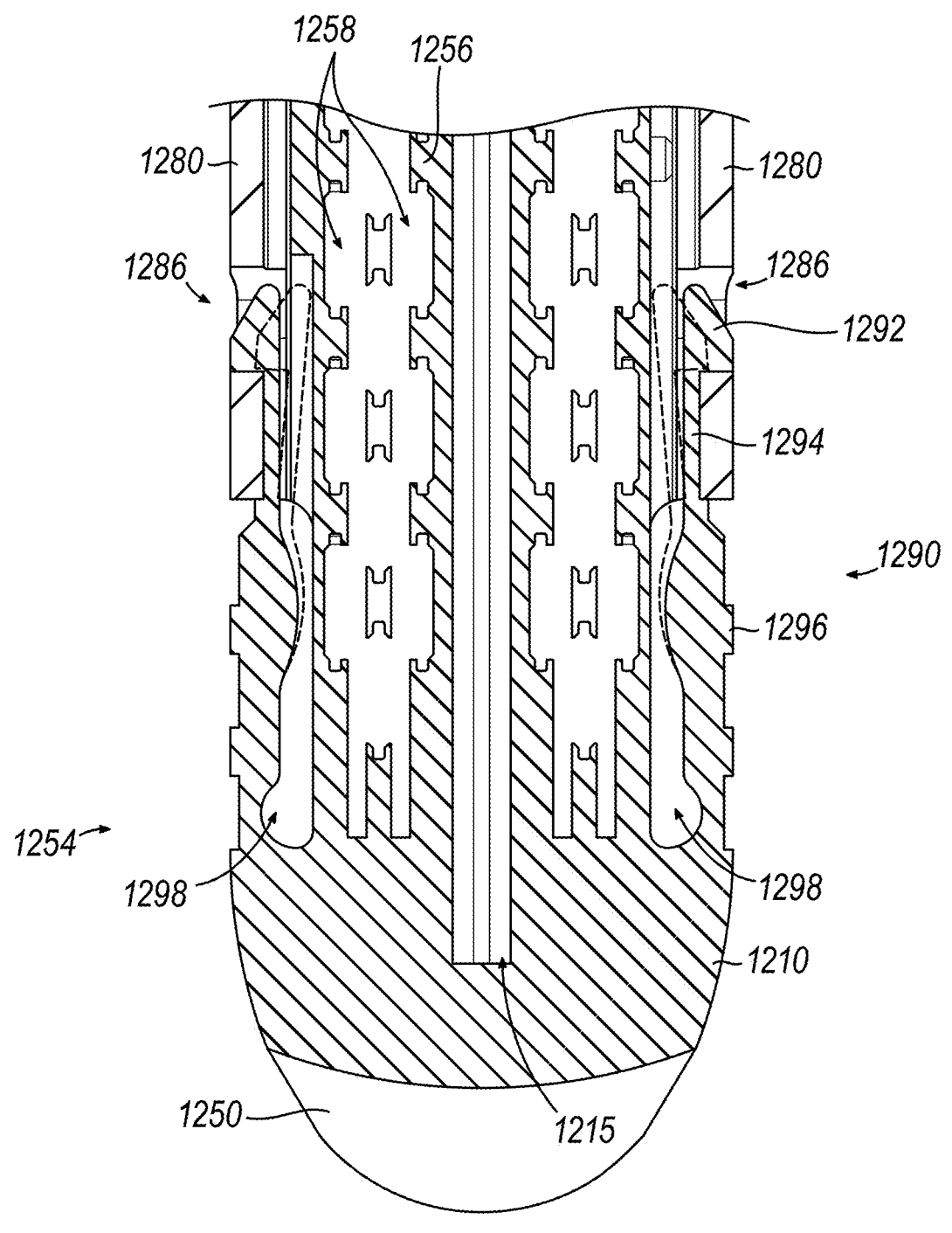
FIG. 24 is a cross-sectional view of the cartridge jaw and the replaceable staple cartridge of FIG. 20A, taken along line 24-24 of FIG. 20B.

Each staple cartridge retainer 1290 includes a latch head 1292, a resilient intermediate projection 1294, and a resilient base grip 1296. Resilient intermediate projection 1294 is attached to both latch head 1292 and resilient base grip 1296. As shown in FIG. 24, resilient base grip 1296 is attached to cartridge body 1250 and extends proximally from cartridge body 1250. Further, resilient base grip 1296, resilient intermediate projection 1294, and latch head 1292 are spaced laterally away from a respective sidewall of cartridge body 1250 to thereby define a cavity 1298.

Latch head 1292, intermediate projection 1294, and base grip 1296 may flex laterally inward/outward in order to suitably couple and decouple with cartridge jaw 1202. During coupling of staple cartridge 1210 with cartridge jaw 1202, when staple cartridge 1210 is suitable aligned with cartridge jaw 1202 as shown in FIG. 20A, a user may insert proximal end of staple cartridge 1210 into the open distal end of cartridge jaw 1202 defining elongated channel 1208. During insertion, latch heads 1292 may engage an interior surface of a respective lateral side wall 1280, such as the portion of sidewall 1280 defining pocket 1288. Engagement between latch head 1292 and its respective interior surface of lateral sidewall 1280 may flex latch head 1292, intermediate projection 1294, and base grip 1296 laterally inward toward cartridge body 1250.

Once latch head 1292 reaches longitudinal alignment with through hole 1286, the resilient nature of intermediate projection 1294 and base grip 1296 may flex latch head 1292 laterally away from staple cartridge body 1250 into the confines of its respective through hole 1286. Engagement between latch head 1292 and the portions of lateral side walls 1280 defining through holes 1286 retain staple cartridge 1210 within cartridge jaw 1202 such that staple cartridge 1210 is inhibited from inadvertently falling out of cartridge jaw 1202 in the distal direction.

While staple cartridge 1210 and cartridge jaw 1202 are coupled together, resilient intermediate projections 1294 may be housed within their respective pocket 1288 defined by lateral side walls 1280 while base grips 1296 may be located distally relative to their respective lateral side walls 1280. Therefore, base grip 1296 may be readily accessible while staple cartridge 1210 is suitable coupled with cartridge jaw 1202.

After cartridge 1210 is spent (e.g., after cartridge 1210 is suitably fired in accordance with the teachings herein), a user may press resilient grips 1296 laterally inward such that latch heads 1292 are no longer retained within the confines of through hole 1286. Simultaneously, a user may pull cartridge 1210 distally away from cartridge jaw 1202 such that latch heads 1292 are distal relative to through holes 1286. A user may further pull cartridge 1210 distally away from cartridge jaw 1202 in order to remove cartridge 1210. Therefore, staple cartridge retainers 1290 may be utilized in order to initial couple cartridge 1210 within lower jaw 1202 prior to illustrative use; and subsequently be utilized in order to easily remove cartridge 1210 from lower jaw 1202 after illustrative use.

Latch head 1292 is dimensioned smaller than the size of through holes 1286. When latch head 1292 is within the confines of through hole 1286, latch head 1292 may move relative to cartridge jaw 1202 along a longitudinal path defined by through hole 1286. Therefore, staple cartridge retainer(s) 1290 initially locates staple cartridge 1210 relative to cartridge jaw 1202 within a predetermined longitudinal range defined by through hole 1286 and latch head 1292. Having at least a slight gap between latch head 1292 and through hole 1286 (as compared to using tight tolerances closely resembling a press-fitting, etc.) may allow for a user to insert and remove cartridge 1210 into/from cartridge jaw 1202 without having to overcome a large frictional braking force that would be present with tighter tolerances. Therefore, a user may easily and reliably couple and decouple cartridge 1210 from cartridge jaw 1202.

However, since cartridge 1210 may still move along a longitudinal path defined by through hole 1286 and latch head 1292, it may be desirable to more accurately align staple forming pockets 1205 with their respective staple 1255 prior to firing staples 1255. As mentioned above, staple cartridge 1210 and anvil jaw 1204 together form a staple cartridge datum locator 1270 that is configured to consistently locate/align staple cartridge 1210 relative to anvil jaw 1204 in response to anvil jaw 1204 pivoting into the closed position (see FIG. 25C); thereby aligning staples 1255 (see FIG. 22) housed within staple cartridge 1210 with their respective staple forming pocket 1205 (see FIG. 21) of anvil jaw 1204.

Staple cartridge datum locator 1270 of the current example includes a pair of upwardly extending protrusions 1272 associated with staple cartridge 1210, and a complementary cavity 1276 associated with the underside of anvil jaw 1204. Upwardly extending protrusions 1272 extend upwardly from staple deck 1256 and are located at the proximal portion 1252 of cartridge body 1250. Upwardly extending protrusions 1272 are located on laterally opposite sides of elongated knife channel 1215 relative to each other.

Upwardly extending protrusions 1272 each define a particulate channel 1274. Particulate channel 1274 is dimensioned to receive particulate (e.g., tissue, fluids, etc.) that may be present in a surgical setting as jaws 1202, 1204 are pivoted into the closed position. If particulate channel 1274 were not present, such particulate may be directly interposed between upwardly extending protrusions 1272 and complementary cavity 1276, thereby reducing the accuracy at which cartridge 1210 is placed with respect to its predetermined datum via staple cartridge datum locator 1270.

Complementary cavity 1276 is located at a proximal location on the underside of anvil jaw 1204. Complementary cavity 1276 is dimensioned to suitably house and engage protrusions 1272 while jaws 1202, 1204 are in the closed position. Each upwardly extending protrusion 1272 includes a pair of slanted engagement surfaces 1275, while complementary cavity 1276 also includes a slanted engagement surface 1278.

Upwardly extending protrusions 1272 and complementary cavity 1276 are configured to engage each other in response to jaws 1202, 1204 pivoting into the closed position. Engagement between protrusions 1272 and cavity 1276 is configured to drive staple cartridge 1210 into the predetermined datum position relative to anvil jaw 1204, thereby suitably aligning staples 1255 housed within staple cartridge 1210 with their respective staple forming pocket 1205. Slanted engagement surfaces 1275 are dimensioned to contact complementary slanted engagement surfaces 1278 of complementary cavity 1276 associated with anvil jaw 1204 in response to jaws 1202, 1204 pivoting toward the closed position. Engagement between surfaces 1275, 1278 moves staple cartridge 1210 longitudinally relative to cartridge jaw 1202 into the predetermined datum position such that staple forming pockets 1205 of anvil jaw 1204 are aligned with their respective staple openings 1258 and staple 1255 of cartridge body 1250. As mentioned above, staple cartridge retainer(s) 1290 initially locate staple cartridge 1210 within an acceptable range such that protrusions 1272 and complementary cavity 1276 may suitably contact each other in response to jaws 1202, 1204 pivoting toward the closed position.

Figure 25A:
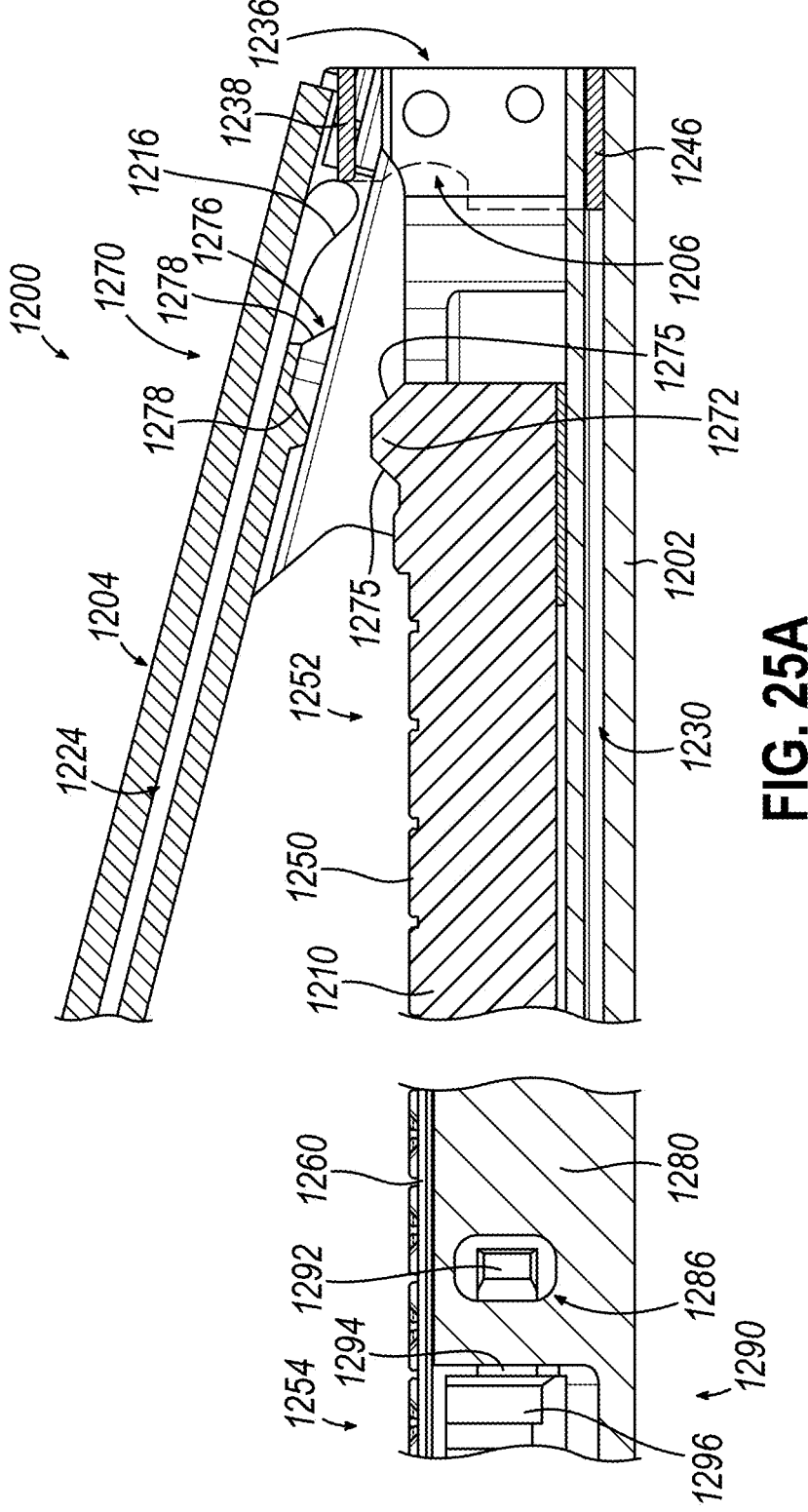
FIG. 25A is a cross-sectional view of the end effector of FIG. 20A, where the cartridge jaw and the anvil jaw are in the open position.
Figure 25B:
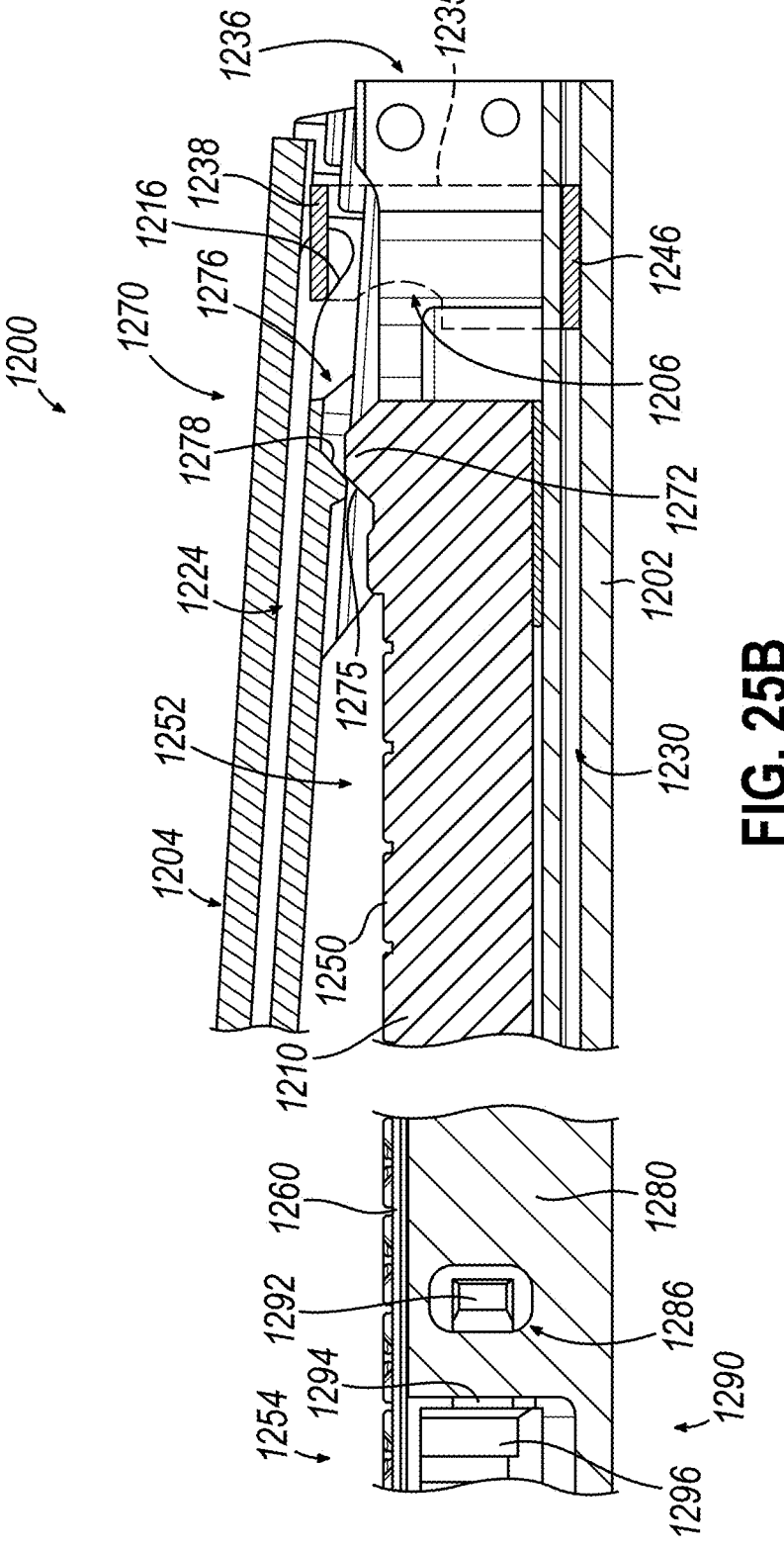
FIG. 25B is a cross-sectional view of the end effector of FIG. 20A, where the cartridge jaw and the anvil jaw are in a partially closed position.
Figure 25C:
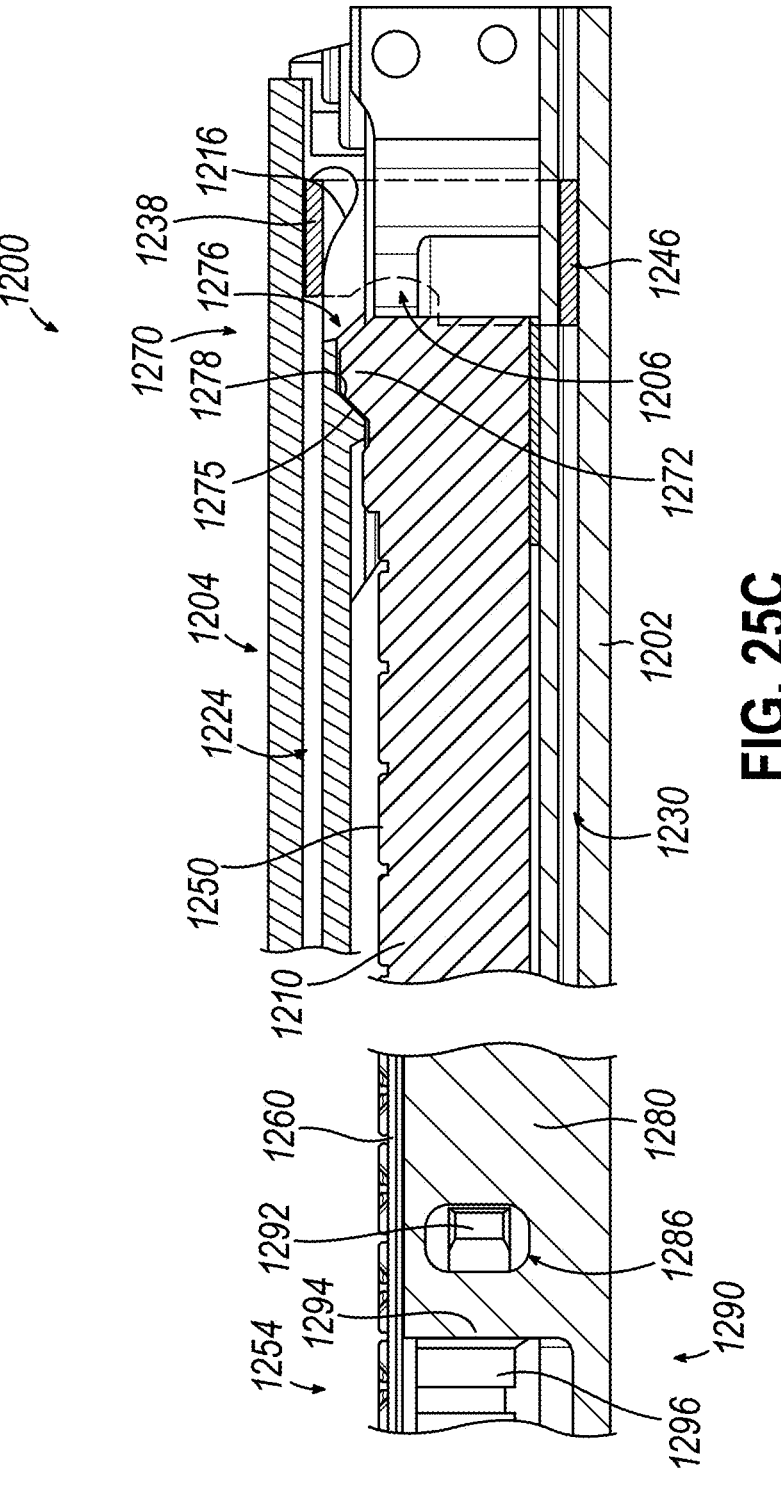
FIG. 25C is a cross-sectional view of the end effector of FIG. 20A, where the cartridge jaw and the anvil jaw are in the closed position.

FIGS. 25A-25C show an illustrative closing of jaws 1202, 1204 such that staple cartridge datum locator 1270 moves cartridge 1210 into its predetermined datum location. First, as shown in FIG. 25, jaws 1202, 1204 are in the open position, while cartridge 1210 is suitably attached to cartridge channel 1202 via staple cartridge retainer 1290. Therefore, while cartridge 1210 is retained within jaw 1202, staple cartridge 1210 may still slightly move relative to jaw 1202 along the path defined by latch head 1292 and through hole 1286. In other words, while jaws 1202, 1204 are in the open position and cartridge 1210 is retained within jaw 1202, cartridge 1210 may potentially still not be located at its predetermined datum location.

Next, as shown in FIG. 25B, jaws 1202, 1204 may initially pivot toward the closed position via distal actuation of knife 1206 and knife sled 1236 in accordance with the description herein. In response to jaws 1202, 1204 pivoting toward each other, slanted engagement surface 1278 of complementary cavity 1276 defined by anvil jaw 1204 may come into initial contact with slanted engagement surface 1275 of upwardly extending protrusions 1272. As mentioned above, staple cartridge retainer 1290 initially locates staple cartridge 1210 within an acceptable range such that engagement surfaces 1275, 1278 may suitably contact each other in response to jaws 1202, 1204 actuating toward the closed position.

Next, as shown in FIG. 25C, jaws 1202, 1204 may then pivot into the closed position. In instances where cartridge 1210 was not located at its predetermined datum location, pivotal movement of jaws 1202, 1204 relative to each other and contact between engagement surfaces 1275, 1278 drives cartridge 1210 relative to cartridge jaw 1202 into its predetermined datum location. Therefore, cartridge 1210 is configured to be located/place into its predetermined datum location in response to jaws 1202, 1204 pivoting relative to each other into the closed position.

It should be understood that engagement between anvil jaw 1204 and cartridge 1210 (via surfaces 1275, 1278) drives cartridge 1210 into its predetermined datum position relative to anvil jaw 1204. Using features directly associated with anvil jaw 1204 and staple cartridge 1210 to align staple cartridge 1210 relative to anvil jaw 1204 may reduce a tolerance stack that would accumulate if other features of end effector 1200 were used to drive staple cartridge 1210 into its predetermined datum. For instance, if features associated with cartridge jaw 1202 were configured to engage staple cartridge 1210 to locate/position cartridge 1210 in its predetermined datum position relative to anvil jaw 1204; all the components interposed between first jaw 1202 and second jaw 1204 may lead to an undesirable tolerance stack, which may reduce the alignment accuracy of the cartridge's 1210 datum position and the anvil jaw 1204.

It should be understood that staple cartridge datum locator 1270 may have any suitable engagement structures configured to engage each other to place staple cartridge 1210 into its predetermined datum, as would be apparent to one skilled in the art in view of the teachings herein. Therefore, while anvil jaw 1204 defines a cavity 1276 and staple cartridge 1210 includes at least one protrusion 1272; in some instances, anvil jaw 1202 may include a protrusion while staple cartridge 1210 may define a cavity.

Figure 26A:
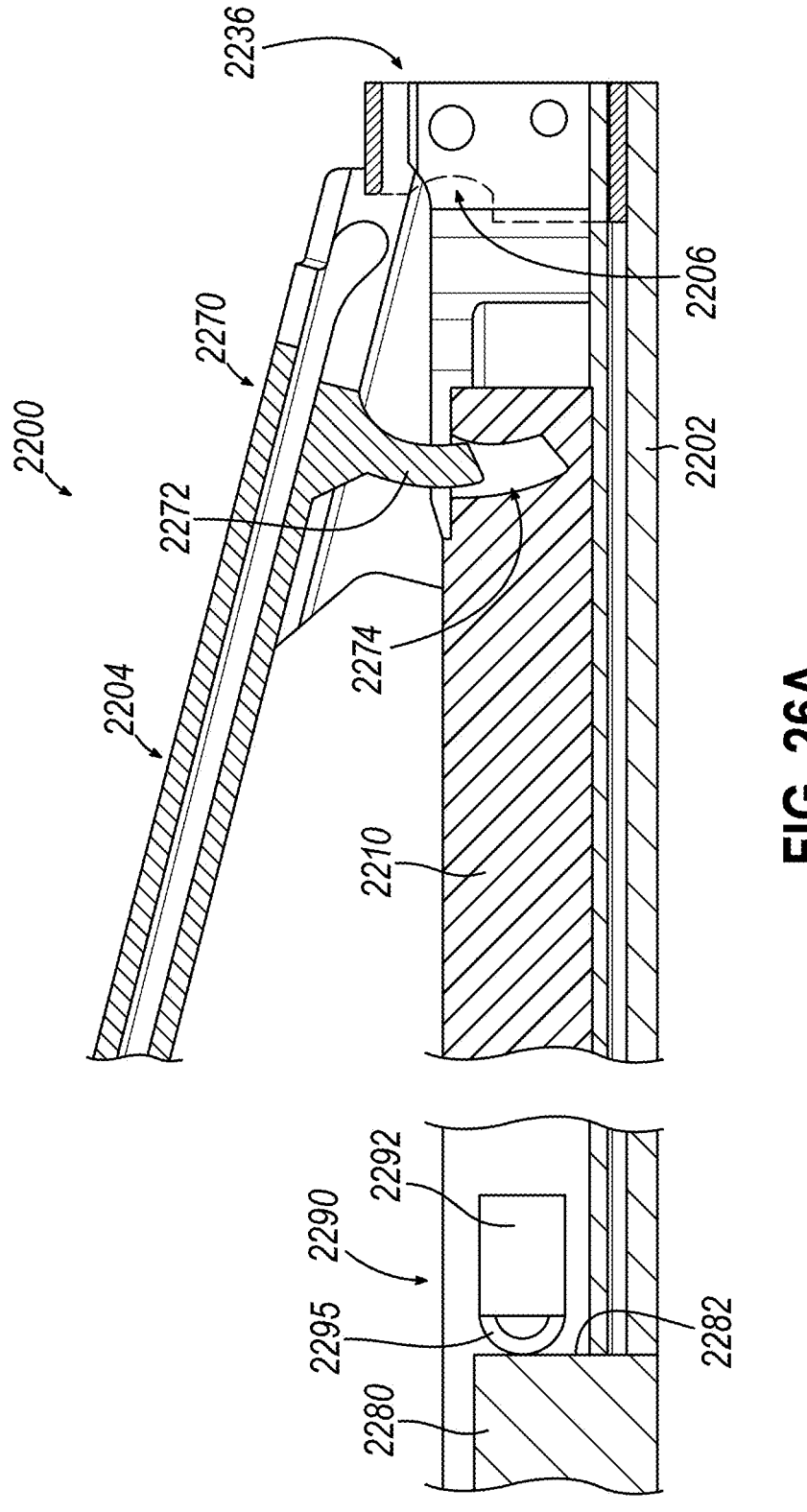
FIG. 26A is cross-sectional view of another alternative end effector in an open position.
Figure 26B:
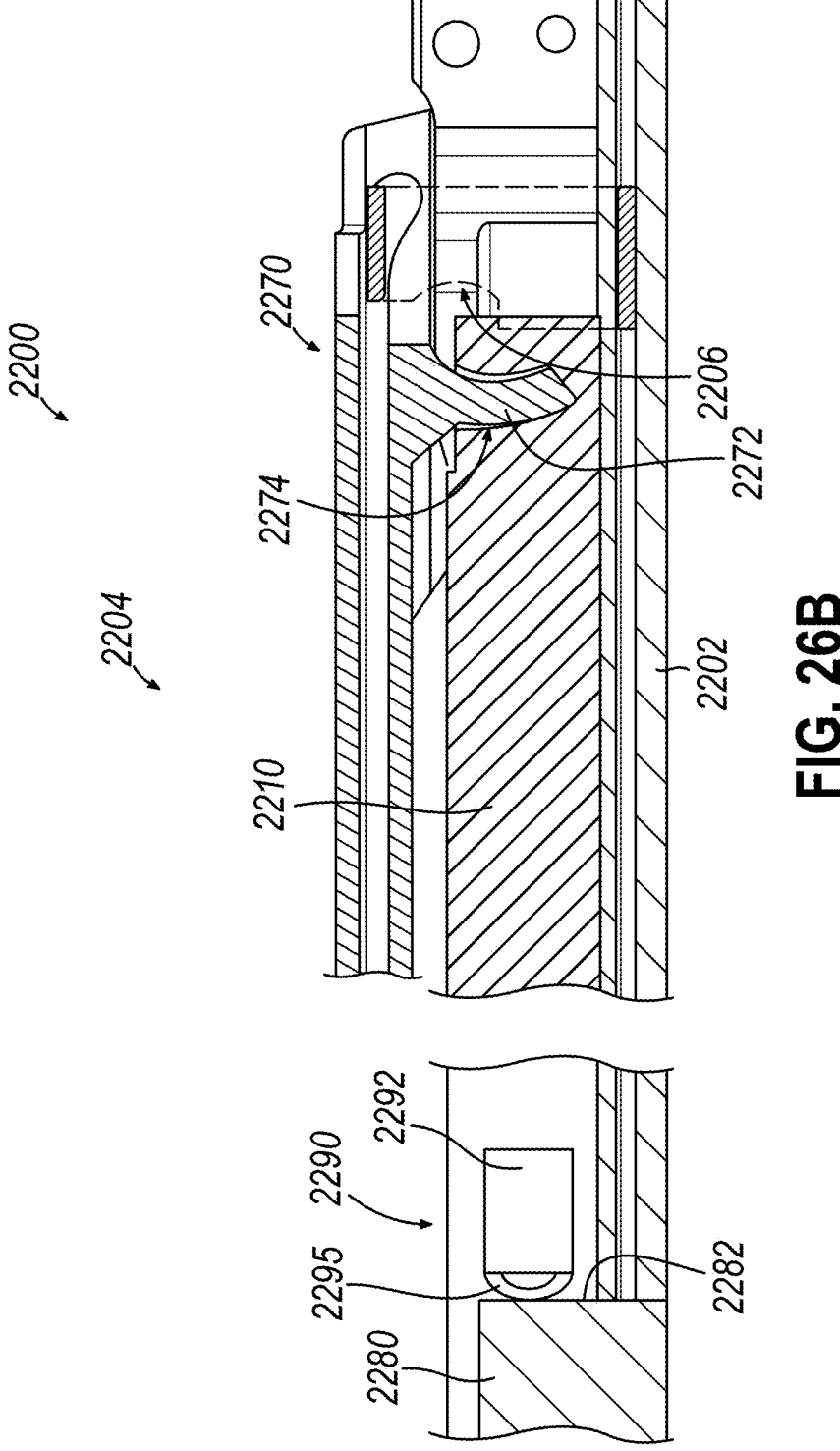
FIG. 26B is a cross-sectional view of the end effector of FIG. 26A in a closed position.

In some instances, features of staple cartridge datum locator 1270 may be engaged with each other, thereby placing cartridge 1210 into its predetermined datum, while jaws 1202, 1204 are in the open position. FIGS. 26A-26B show an illustrative end effector 2200 that may be substantially similar to end effector 1200 described above, with differences elaborated herein. Therefore, end effector 2200 may be readily incorporated into instrument 1000 in replacement of end effector 200, 1200 described above. End effector 2200 includes a cartridge jaw 2202, an anvil jaw 2204, a replaceable staple cartridge 2210, a knife sled 2236, and a knife 2206; which may be substantially similar to cartridge jaw 202, 1202, anvil jaw 204, 1204, staple cartridge 210, 1210, knife sled 236, 1236, and knife 206, 1206 described above, respectively, with differences elaborated herein.

End effector 2200 includes at least one staple cartridge retainer 2290 associated with staple cartridge 2210, and a staple cartridge datum locator 2270 formed by anvil jaw 2204 and staple cartridge 2210. Staple cartridge retainer 2290 and staple cartridge datum locator 2270 may be substantially similar to staple cartridge retainer 1290 and staple cartridge datum locator 1270 described above, with differences elaborated below.

Therefore, staple cartridge retainer 2290 is configured to engage and/or interface with cartridge jaw 2202 such that that staple cartridge 2210 does not inadvertently disassociate with cartridge jaw 2202 during illustrative use. Further, staple cartridge retainer(s) 2290 may be utilized in order to quickly and easily decouple a spent staple cartridge 2210 from cartridge jaw 2202. Further, staple cartridge datum locator 2270 is configured to consistently locate/align staple cartridge 2210 relative to anvil jaw 2204 in order to align staples housed within staple cartridge 2210 with their respective staple forming pocket (not shown) of anvil jaw 2204.

Staple cartridge retainer 2290 includes a latch 2292 which may function substantially similar to latch head 1292, resilient intermediate projection 1294, and resilient base grip 1296 described above. Additionally, staple cartridge retainer 2290 includes a biasing spring 2295 associated with latch 2292. Biasing spring 2295 is configured to engage an engagement surface 2282 of lateral sidewall 2280 of cartridge jaw 2202 when staple cartridge 2210 is suitably coupled to cartridge jaw 2202. Engagement between biasing spring 2295 and engagement surface 2282 is configured to bias staple cartridge 2210 proximally relative to cartridge jaw 2202.

Staple cartridge datum locator 2270 of the current example includes a downward extending projection 2272 associated with anvil jaw 2204, and a complementary recess 2274 defined by cartridge 2210. As shown in FIG. 26A, projection 2272 and recess 2274 are configured to engage each other while jaws 2202, 2204 are in the open position. Additionally, biasing spring 2295 biases staple cartridge 2210 such that projection 2272 and recess 2274 are suitably engaged with each other to locate staple cartridge 2210 at its predetermined datum position, even when jaws 2202, 2204 are in the open position as shown in FIG. 26A.

Further, projections 2272 and recess 2274 are dimensioned in order to remain suitable engaged with each other (i.e., to locate cartridge 2210 at its predetermined datum position relative to anvil 2204) while jaws 2202, 2204 pivot relative to each other between the open and closed position. Biasing spring 2295 may assist in keeping projections 2272 and recess 2284 suitably engaged with each other while jaws 2202, 2204 pivot and/or while jaws 2202, 2204 are in the open position. Allowing cartridge 2210 to be located at its predetermined datum position while jaws 2202, 2204 are open, closed, and in any position therebetween, may inhibit movement of cartridge 2210 relative to cartridge jaw 2202 while jaws 2202, 2204 pivot into the closed position as shown in FIG. 26B.

Figure 27:
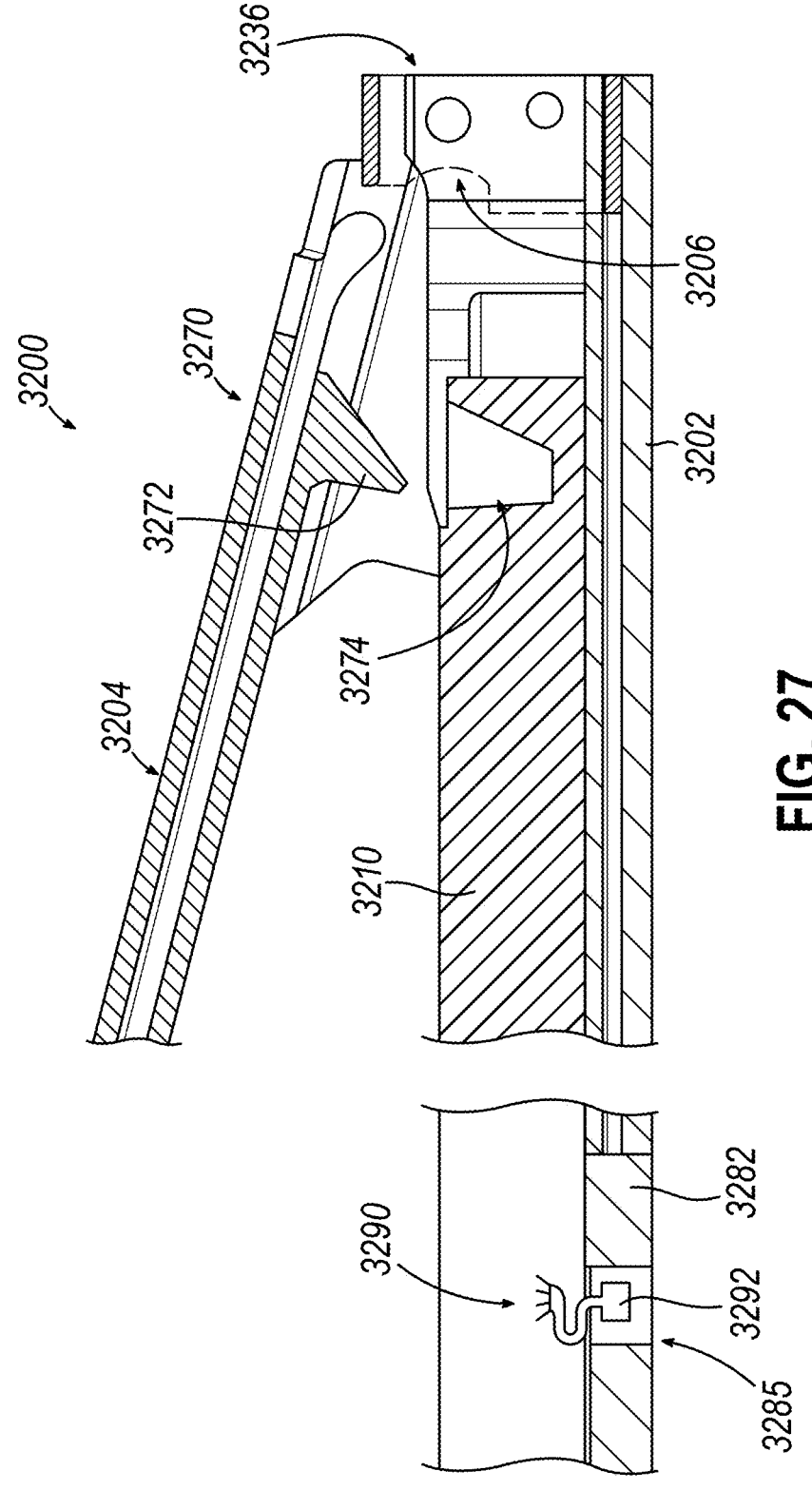
FIG. 27 is a cross-sectional view of another alternative end effector in an open position.

FIG. 27 shows an illustrative end effector 3200 that may be substantially similar to end effector 1200, 2200 described above, with differences elaborated herein. Therefore, end effector 3200 may be readily incorporated into instrument 1000 in replacement of end effector 200, 1200, 2200 described above. End effector 3200 includes a cartridge jaw 3202, an anvil jaw 3204, a replaceable staple cartridge 3210, a knife sled 3236, and a knife 3206; which may be substantially similar to cartridge jaw 202, 1202, 2202, anvil jaw 204, 1204, 2204, staple cartridge 210, 1210, 2210, knife sled 236, 1236, 2236, and knife 206, 1206, 2206 described above, respectively, with differences elaborated herein.

End effector 3200 includes at least one staple cartridge retainer 3290 associated with staple cartridge 3210, and a staple cartridge datum locator 3270 formed by anvil jaw 3204 and staple cartridge 3210. Staple cartridge retainer 3290 and staple cartridge datum locator 3270 may be substantially similar to staple cartridge retainer 1290, 2290 and staple cartridge datum locator 1270, 2270 described above, with differences elaborated below.

Therefore, staple cartridge retainer 3290 is configured to engage and/or interface with cartridge jaw 3202 such that that staple cartridge 3210 does not inadvertently disassociate with cartridge jaw 3202 during illustrative use. Further, staple cartridge retainer(s) 3290 may be utilized in order to quickly and easily decouple a spent staple cartridge 3210 from cartridge jaw 3202. Further, staple cartridge datum locator 3270 is configured to consistently locate/align staple cartridge 3210 relative to anvil jaw 3204 in order to align staples housed within staple cartridge 3210 with their respective staple forming pocket (not shown) of anvil jaw 3204.

Staple cartridge retainer 3290 includes a resilient latch 3292 which may function substantially similar to latch head 1292, resilient intermediate projection 1294, and resilient base grip 1296 described above. Therefore latch 3292 allows for staple cartridge 3210 to be selectively coupled and decoupled from cartridge jaw 3202, inhibits staple cartridge 3210 from disassociating with cartridge jaw 3202, and suitably aligned features of datum locator 3270 to engage each other in response to jaws 3202, 3204 pivoting toward the closed position. However, in the current example, latch 3292 is configured to flex within a through hole 3285 defined by base 3282 of cartridge jaw 3202, rather than a lateral side wall of cartridge jaw 3202. Such a through hole 3285 may be located at a distal end of base 3282.

While locator 1270 describe above includes a projection associated with the cartridge and a recess associated with the anvil jaw, staple cartridge datum locator 3270 of the current example includes a downward extending projection 3272 associated with anvil jaw 3204, and a complementary recess 3274 defined by cartridge 3210. Similar to locator 1270 described above, downwardly extending projection 3272 and recess 3274 are configured to engage each other as jaws 3202, 3204 pivot toward the closed position in order to drive cartridge 3210 relative to jaws 3202, 3204 into a predetermined datum position. In particular, projection 3277 and recess 3274 include complementary slanted surfaces that contact each other while jaws 3202, 3204 pivot toward the closed position.

Figure 28A:
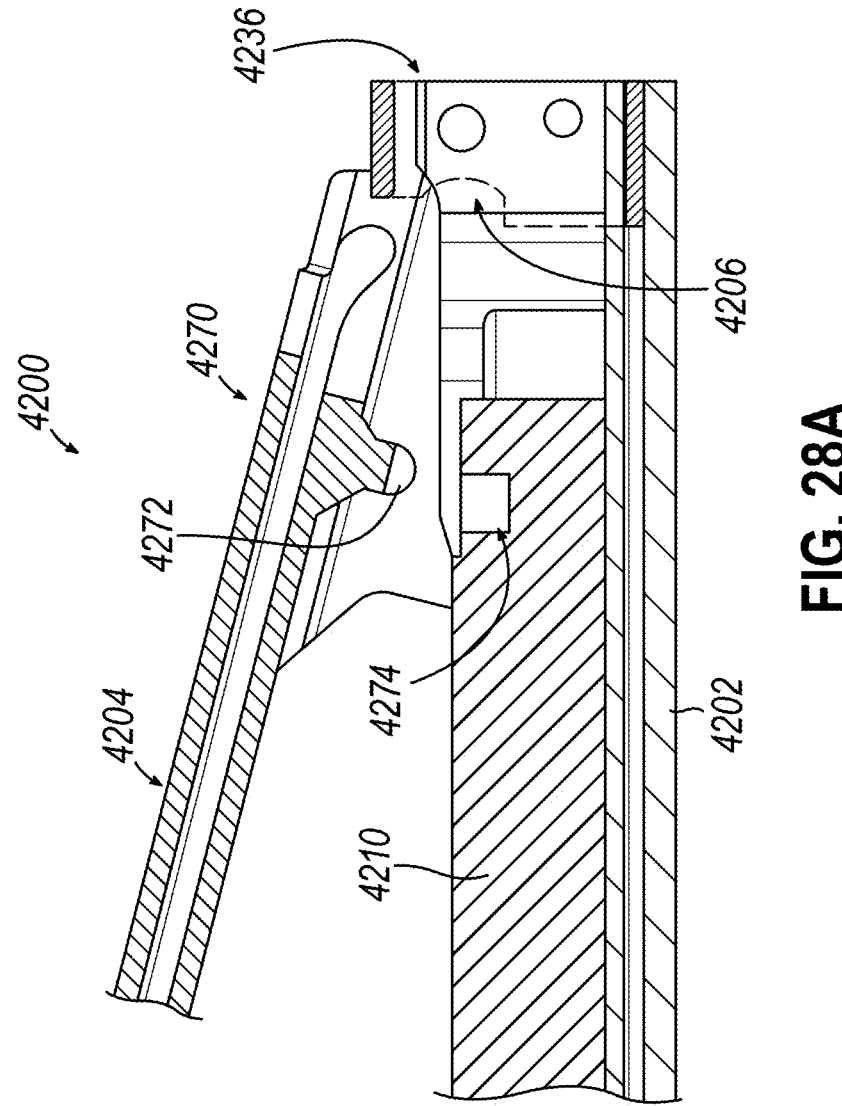
FIG. 28A is a cross-sectional view of another alternative end effector in an open position.
Figure 28B:
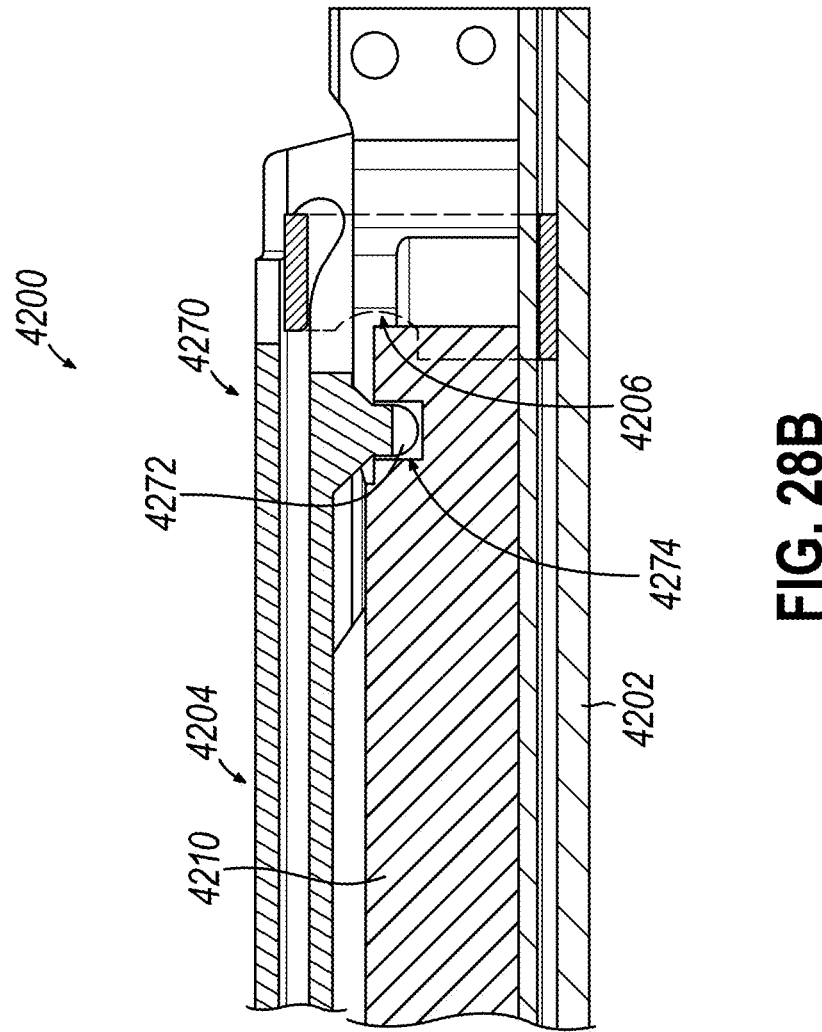
FIG. 28B is a cross-sectional view of the end effector of FIG. 28A in a closed position.

While complementary slanted surfaces are used in the current example, projection 3277 and recess 3274 may have any other suitable geometry in order to engage each other as would be apparent to one skilled in the art in view of the teachings herein. For example, FIGS. 28A-28B show an alternative end effector 4200 that may be substantially similar to end effector 3200 described above, except features of staple cartridge datum locator 4270 include an alternative geometry. Therefore, end effector 4200 may be readily incorporated into instrument 1000 in replacement of end effector 200, 1200, 2200, 3200, described above. FIGS. 28A-28B show end effector 4200 transitioning from the open position into the closed position.

Therefore, end effector 4200 includes a cartridge jaw 4202, an anvil jaw 4204, a replaceable staple cartridge 4210, a knife sled 4236, and a knife 4206; which may be substantially similar to cartridge jaw 202, 1202, 2202, 3202, anvil jaw 204, 1204, 2204, 3204, staple cartridge 210, 1210, 2210, 3210, knife sled 236, 1236, 2236, 3236, and knife 206, 1206, 2206, 3206 described above, respectively, with differences elaborated herein. While not shown, end effector 4200 includes a suitable staple cartridge retainer that may be substantially similar to staple cartridge retainer 1290, 2290, 3290 described above.

Further, end effector 4200 includes a staple cartridge datum locator 4270 formed by anvil jaw 4204 and staple cartridge 4210. Datum locator 4270 may be substantially similar to datum locater 3270 described above. Therefore, datum locator 4270 includes a downward extending projection 4272 associated with anvil jaw 4204, and a complementary recess 4274 defined by cartridge 4210. Downwardly extending projection 4272 and recess 4274 are configured to engage each other as jaws 4202, 4204 pivot toward the closed position in order to drive cartridge 4210 relative to jaws 4202, 4204 into a predetermined datum position. However, rather than having just slanted surfaces, downward extension projection 4272 includes a pair of slanted surfaces that terminate into a rounded tip. Additionally, as shown in FIG. 28B, recess 4274 is designed to house rounded tip while jaws 4202, 4204 are in the closed position, while slanted surface are not housed within recess 4274. Therefore, rounded tip and the recess 4274, while jaws 4202, 4204 are in the closed position, are configured to drive cartridge 4210 into its predetermined datum position.

Figure 29:
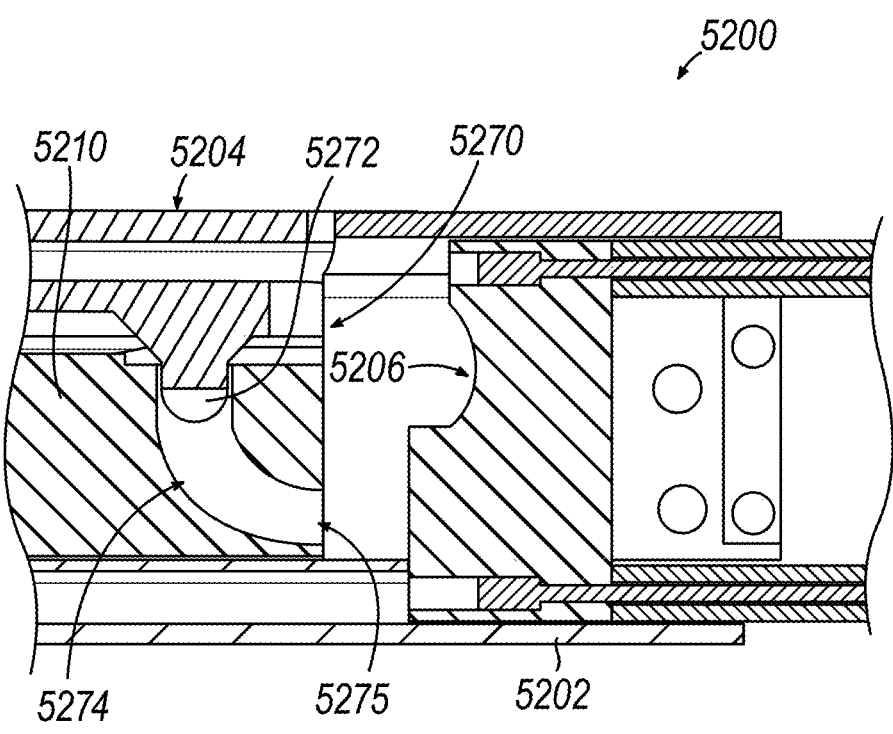
FIG. 29 is a cross-sectional view of another alternative end effector in an closed position.

FIG. 29 shows another alternative end effector 5200 that may be substantially similar to end effector 4200 described above, with differences elaborated herein. Therefore, end effector 5200 may be readily incorporated into instrument 1000 in replacement of end effector 200, 1200, 2200, 3200, 4200 described above. End effector 5200 includes jaws 5202, 5204 and cartridge 5210 that may be substantially similar to jaws 4202, 4204 and cartridge 4210 described above, respectively, with different elaborated below.

Additionally, end effector 5200 includes a staple cartridge datum locator 5270 formed by anvil jaw 5204 and staple cartridge 5210. Datum locator 5270 may be substantially similar to datum locater 4270 described above. Therefore, datum locator 5270 includes a downward extending projection 5272 associated with anvil jaw 5204, and a complementary recess 5274 defined by cartridge 5210. However, in the current example, complementary recess 5274 is extended proximally to include a particulate channel 5275. Similar to particulate channel 1274 described above, particulate channel 5275 is dimensioned to receive particulate (e.g., tissue, fluids, etc.) that may be present in a surgical setting as jaws 5202, 5204 are pivoted into the closed position. Particulate channel 5275 may terminate within the confines of staple cartridge 5210 or may extend into an outlet port defined by a staple cartridge channel 5210. If particulate channel 5275 were not present, such particulate may be directly interposed between projection 5272 and recess 5274, thereby reducing the accuracy at which cartridge 5210 is placed with respect to its predetermined datum via staple cartridge datum locator 5270.

As mentioned above, staple cartridge datum locators 1270, 2270, 3270, 4270, 5270 each include a feature associated with anvil jaw 1204, 2204, 3204, 4204, 5204 that pivots with anvil jaw 1204, 2204, 3204, 5204 relative to cartridge jaw 1202, 2202, 3202, 4202 5202 in order to drive staple cartridge 1210, 2210, 3210, 4210, 5210 into its predetermined datum position. In some instances, it may be desirable to actuate such features associated with anvil jaw 1204, 2204, 3204, 4204, 5204 along a linear path in order to drive staple cartridge 1210, 2210, 3210, 4210, 5210 into its predetermined datum position.

Figure 30A:
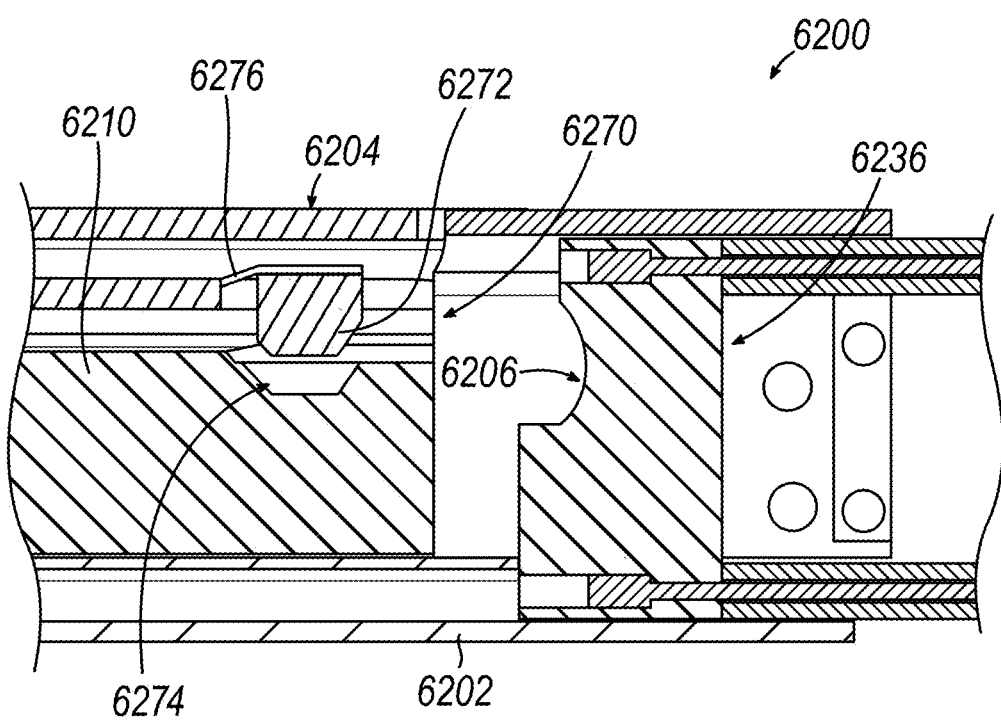
FIG. 30A is a cross-sectional view of another alternative end effector in an open position.
Figure 30B:
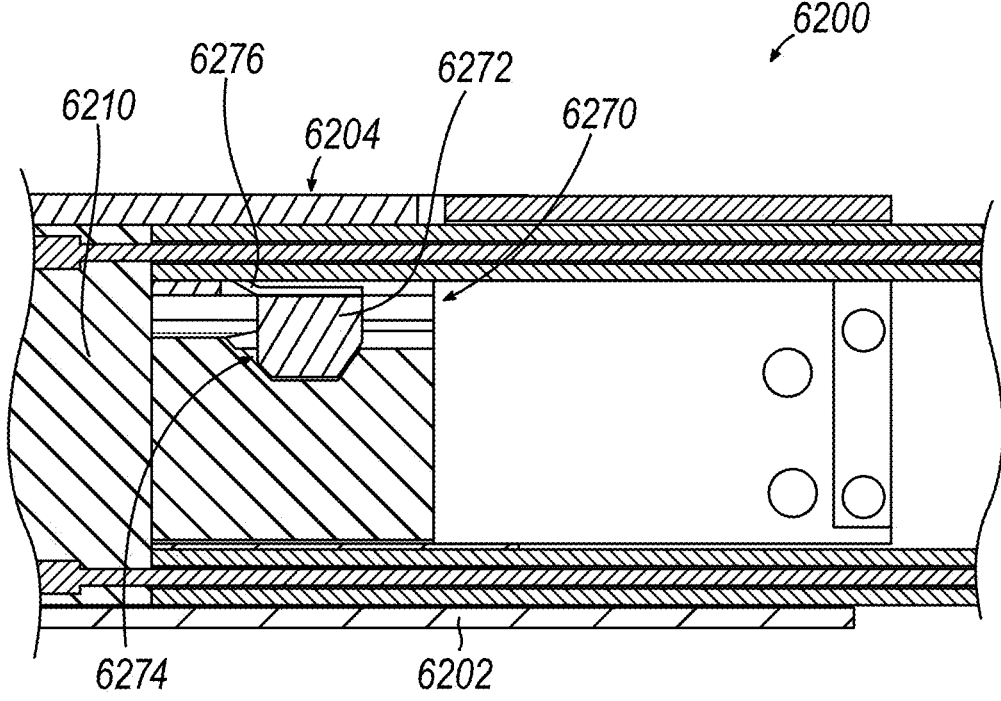
FIG. 30B is a cross-sectional view of the end effector of FIG. 30A in a closed position.

FIGS. 30A-30B show an alternative end effector 6200 that may be substantially similar to end effector 1200, 2200, 3200, 4200, 5200 described above, except features of staple cartridge datum locator 6270 includes an alternative geometry that actuates along a substantially linear path (or a linear path) in order to drive staple cartridge 6210 into its predetermined datum position. Therefore, end effector 6200 may be readily incorporated into instrument 1000 in replacement of end effector 200, 1200, 2200, 3200, 4200, 5200 described above. FIGS. 30A-30B show staple cartridge datum locator 6270 transitioning from the open position into the closed position.

Therefore, end effector 6200 includes a cartridge jaw 6202, an anvil jaw 6204, a replaceable staple cartridge 6210, a knife sled 6236, and a knife 6206; which may be substantially similar to cartridge jaw 202, 1202, 2202, 3202, 4202, 5202, anvil jaw 204, 1204, 2204, 3204, 4204, 5204, staple cartridge 210, 1210, 2210, 3210, 4210, 5210, knife sled 236, 1236, 2236, 3236, 4236, and knife 206, 1206, 2206, 3206, 4206 described above, respectively, with differences elaborated herein. While not shown, end effector 6200 includes a suitable staple cartridge retainer that may be substantially similar to staple cartridge retainer 1290, 2290, 3290 described above.

Further, end effector 6200 includes a staple cartridge datum locator 6270 formed by anvil jaw 6204 and staple cartridge 6210. Datum locator 6270 may be substantially similar to datum locater 1270, 2270, 3270, 4270, 5270, described above, with differences elaborated below. Therefore, datum locator 6270 includes a downward extending projection 6272 associated with anvil jaw 6204, and a complementary recess 6274 defined by cartridge 6210. Downwardly extending projection 6272 and recess 6274 are configured to engage each other as knife 6206 and knife sled 6236 actuates distally from a proximal position in order to drive cartridge 6210 relative to jaws 6202, 6204 into a predetermined datum position. However, rather than downwardly extending projection 6272 pivoting along with anvil jaw 6204 relative to cartridge jaw 6202, downwardly extending projection 6272 actuates along a substantially linear path to engage recess 6274.

In the current example, downwardly extending projection 6272 is attached to an underside of anvil jaw 6204 via a leaf spring 6276. Leaf spring 6276 biases downwardly extending projection 6272 toward the position shown in FIG. 30A.

Downwardly extending projection 6272 is also configured to engage a suitable portion of knife sled 6236 (or a suitable component of knife firing subsystem 500) as knife sled 6236 actuates distally as shown between FIGS, 30A-30B. Engagement between downwardly extending projection 6272 and knife sled 6236 and/or knife firing subsystem 500 is configured to drive downwardly extending projection 6272 along a substantially linear path into direct engagement with portions of staple cartridge 6210 defining complementary recess 6274. Engagement between projection 6272 and recess 6274 is configured to move staple cartridge 6210 into its predetermined datum position relative to anvil jaw 6204 in the closed position. Knife sled 6236 and/or knife firing system 500 may keep downwardly extending projection 6272 into engagement with recess 6274 while knife sled 6236 is distal relative to projection 6272. Therefore, once knife sled 6236 is retracted proximally, the biasing nature of leaf spring 6276 may actuate projection 6272 back to the position shown in FIG. 30A.

FIGS. 31-34C show an alternative end effector 7200 that may be substantially similar to end effector 1200, 2200, 3200, 4200, 5200, 6200 described above, with differences elaborated herein. Therefore, end effector 7200 may be readily incorporated into instrument 1000 in replacement of end effector 200, 1200, 2200, 3200, 4200, 5200, 6200 described above. End effector 7200 includes a cartridge jaw 7202, an anvil jaw 7204, a replaceable staple cartridge 7210, a knife sled 7236, and a knife 7206; which may be substantially similar to cartridge jaw 202, 1202, 2202, 3202, 4202, 5202, 6202, anvil jaw 204, 1204, 2204, 3204, 4204, 5204, 6204, staple cartridge 210, 1210, 2210, 3210, 4210, 5210, 6210, knife sled 236, 1236, 2236, 3236, 4236, 6236, and knife 206, 1206, 2206, 3206, 4206, 6206, described above, respectively, with differences elaborated herein.

Figure 31:
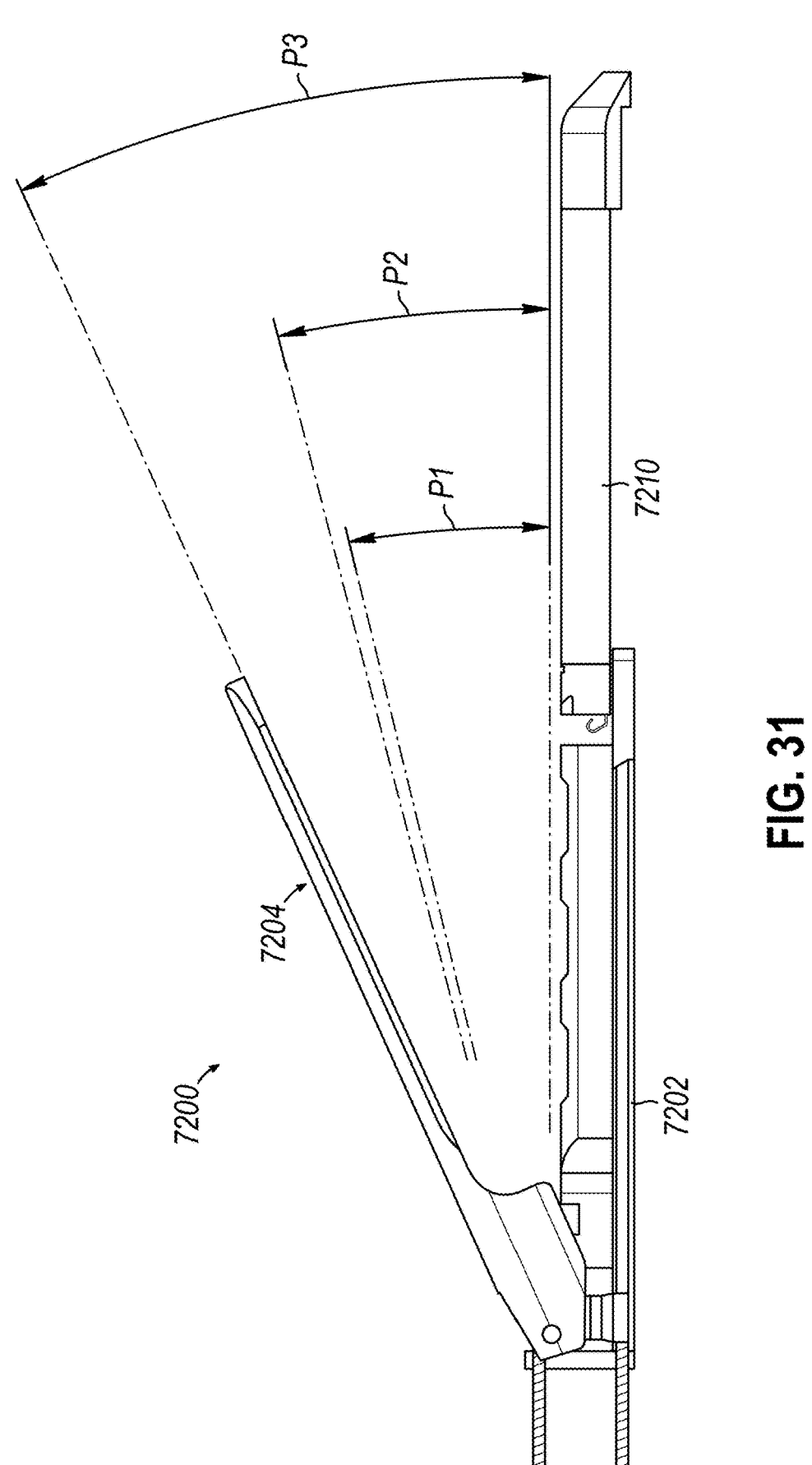
FIG. 31 is an elevational side view of another end effector in a largest open position.

Staple cartridge 7210 may be designed to be inserted into cartridge jaw 7202 in substantially similar manner as staple cartridge 1210 and cartridge jaw 1202 described above. Therefore, in order to couple cartridge 7210 with jaw 7202, cartridge must be aligned with jaw 7202 as shown in FIG. 31, and then inserted proximally within jaw 7202.

Further, end effector 7200 includes a staple cartridge datum locator 7270. As will be described in greater detail below, staple cartridge datum locator 7270 is configured to consistently locate/align staple cartridge 7210 relative to anvil jaw 7204 in order to align staples housed within staple cartridge 7210 with their respective staple forming pocket (not shown) of anvil jaw 7204. Additionally, staple cartridge datum locator 7270 is also configured to inhibit staple cartridge 7210 from inadvertently disassociating with cartridge jaw 7202 during illustrative use.

Anvil jaw 7204 defines a longitudinally extending upper channel 7224 that may be substantially similar to longitudinally extending upper channel 224, 1224 described above. Further, anvil jaw 7204 includes a ramp surface 7216 that may be substantially similar to ramp surface 216, 1216 described above. Therefore, while end effector 7200 is suitably loaded onto a robotic arm, an upper knife tab 7238 of knife sled 7236 is configured to engage ramp surface 7216 in order to pivot jaws 7202, 7204 into the closed position.

Figure 32:
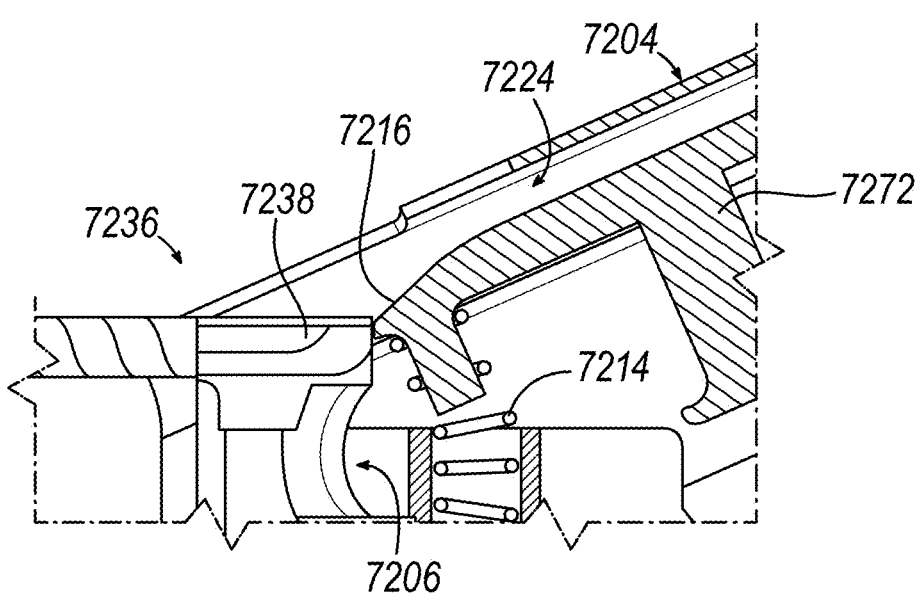
FIG. 32 is a cross-sectional view of the end effector of FIG. 31 in the largest open position.

In the current example, jaws 7202, 7204 are biased toward a largest open position (P3) via spring 7214. As shown in FIG. 32, when jaws 7202, 7204 are in the largest open position, upper knife tab 7238 is misaligned such that it cannot ride along ramp surface 7216 to pivot jaws 7202, 7204. In other words, when jaws 7202, 7204 are in the largest open position (P3), jaws 7202, 7204 are locked out from receiving knife 7206. Jaws 7202, 7204 may only access the largest open position (P3) when a cartridge 7210 is not loaded onto cartridge jaw 7202. Therefore, if a user tries to attach end effector 7200 onto a robotic arm while jaws 7202, 7204 are biased into the largest open position (P3) (i.e., there is no cartridge 7210 loaded), then robotic arm will be locked out from closing jaws 7202, 7204.

As will be described in greater detail below, when a cartridge 7210 is suitably loaded onto cartridge jaw 7202, staple cartridge datum locator 7270 is configured to inhibit jaws 7202, 7204 from reaching the largest open position (P3), and restrict jaws 7202, 7204 from pivoting further open past the second open position (P2). As will also be described in greater detail below, once a cartridge 7210 is suitable loaded onto cartridge jaw 7202 and suitably coupled to a robot arm, knife sled 7236 may be actuated to engage ramp 7216 to pivot jaws 7202, 7204 from the second open position (P2) into the operating open position (P1).

Staple cartridge locator 7270 includes a downwardly extending projection 7272 associated with a proximal end of anvil jaw 7204, a locking ledge 7276 associated with a proximal end of staple cartridge 7210, a recessed pocket 7274 defined by staple cartridge 7210, and a bias spring 7278 attached to a proximal end of staple cartridge 7210. FIGS. 33C and 33D show staple cartridge 7210 suitably coupled to cartridge jaw 7202 in the open position and the closed position, respectively.

When staple cartridge 7210 is suitably coupled to cartridge jaw 7202, downwardly extending projection 7272 is housed within recessed pocket 7274. Although bias spring 7214 naturally biases anvil jaw 7204 upwards toward the largest open position (P3), a bottom portion of downwardly extending projection 7272 engages an underside of locking ledge 7276, thereby restricting jaws 7202, 7204 from pivoting further open past the second open position (P2). It should be noted that when a suitably loaded end effector 7200 is attached to a robotic arm, robotic arm may actuate knife sled 7236 distally in order to slightly close jaws 7202, 7204 relative to each other such that the bottom portion of the downwardly extending projection 7272 no longer engages the underside of locking ledge 7276. This may be associated with the operating open position (P1) shown in FIG. 31.

Additionally, when staple cartridge 7210 is suitably coupled to cartridge jaw 7202, leaf spring 7278 biases cartridge 7210 distally relative to cartridge jaw 7202 such that locking ledge 7276 abuts against a surface of downwardly extending projection 7272. Engagement between locking ledge 7276 and downwardly extending projection 7272, as shown in FIGS. 33C and 33D caused by the distal bias of spring 7278 positions staple cartridge 7210 at its predetermined datum position relative to anvil jaw 7204. Further, engagement between locking ledge 7276 and downwardly extending projection 7272 inhibit staple cartridge 7210 from inadvertently disassociating with cartridge jaw 7202 during illustrative use via distal movement of staple cartridge 7210 relative to cartridge jaw 7202.

FIGS. 33A-33D show an illustrative coupling of cartridge 7210 onto cartridge jaw 7202 such that staple cartridge locator 7270 positions staple cartridge 7210 into its predetermined datum position. First, anvil jaw 7204 may be pivoted to its largest open position (P3) or a suitable position between the largest open position (P3) and the second open position (P2). Next, staple cartridge 7210 may be proximally inserted into the confines of cartridge jaw 7202 to the position shown in FIG. 33A, while anvil jaw 7204 may be pivoted toward the position shown in FIG. 33A. It should be understood that at this moment, end effector 7200 is decoupled from a robotic arm.

Figure 33A:
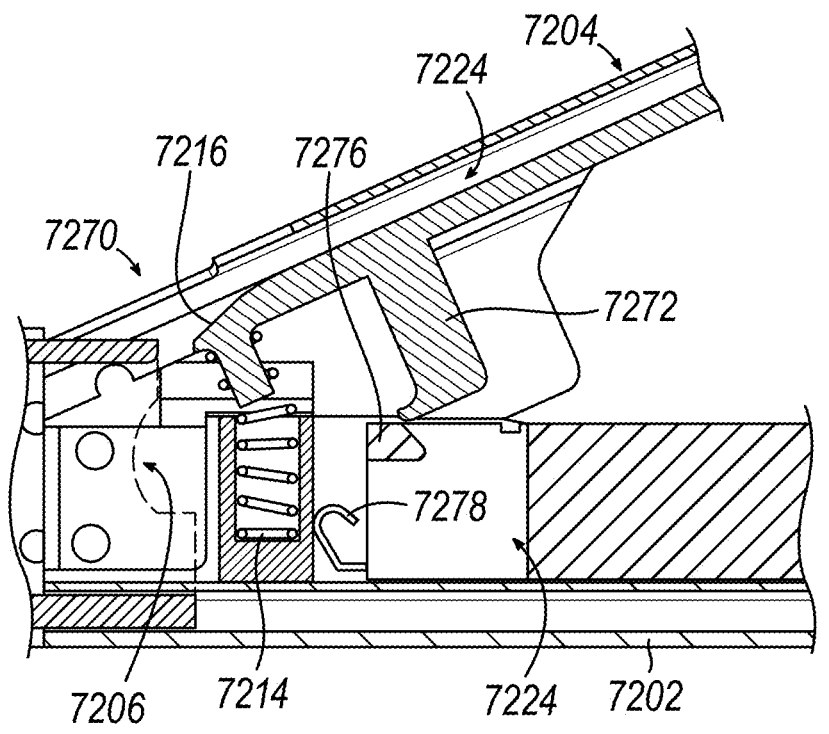
FIG. 33A is a cross-sectional view of the end effector of FIG. 31, where a staple cartridge is initially being attached to a cartridge jaw of the end effector, where a staple cartridge datum locator of the end effector is disengaged.
Figure 33B:
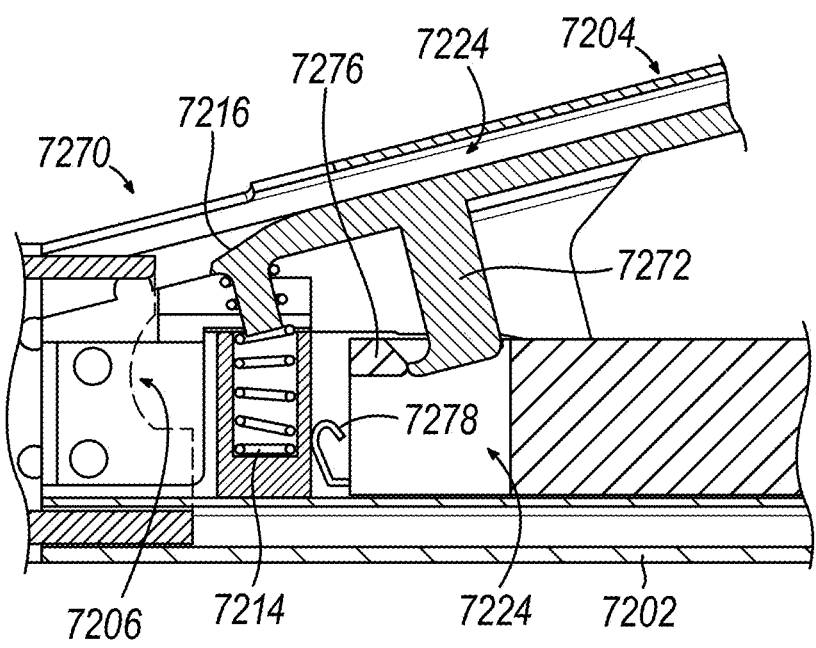
FIG. 33B is a cross-sectional view of the end effector of FIG. 31, where the staple cartridge datum locator of FIG. 33A is initially engaged.
Figure 33C:
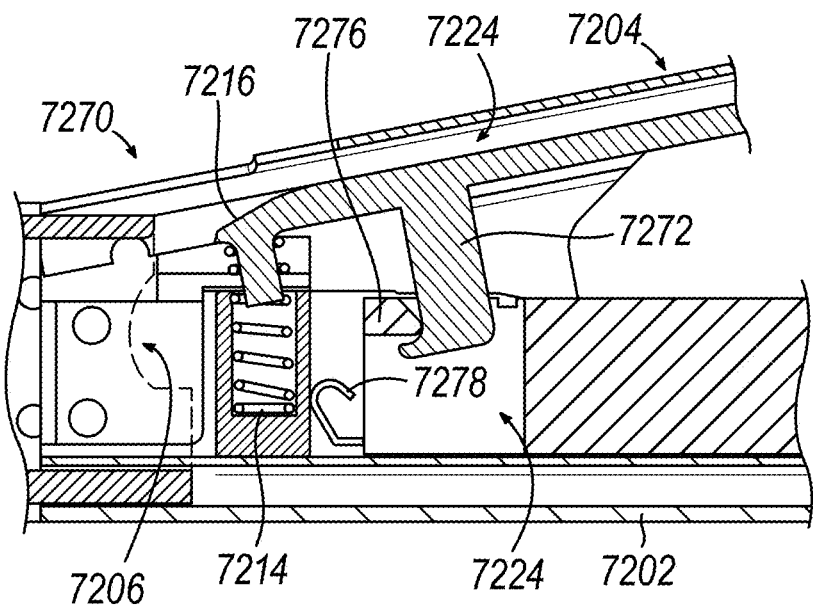
FIG. 33C is a cross-sectional view of the end effector of FIG. 31, where the staple cartridge datum locator of FIG. 33A is fully engaged while the end effector is in an intermediate open position.
Figure 33D:
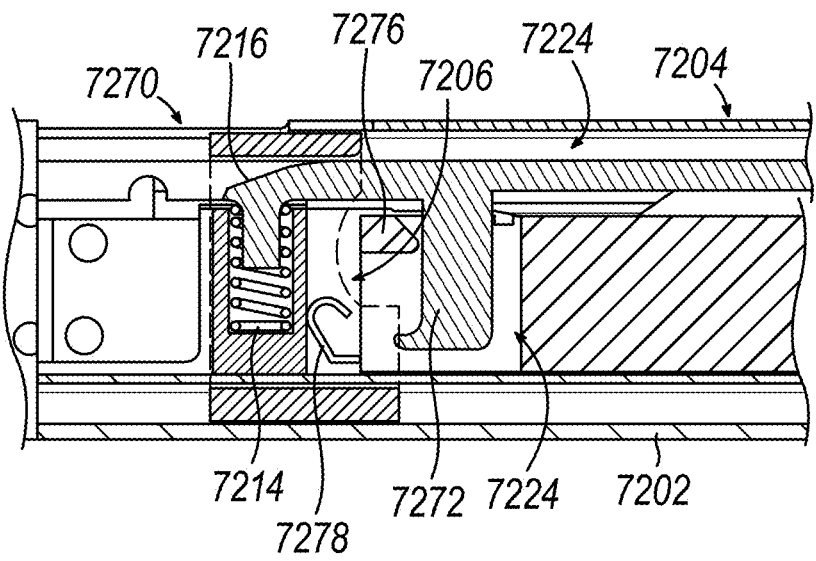
FIG. 33D is a cross-sectional view of the end effector of FIG. 31, where the staple cartridge datum locator of FIG. 33A is fully engaged while the end effector is in a closed position.

Next, as shown in FIG. 33B, anvil jaw 7204 may be pivoted further toward cartridge jaw 7202 such that a tip of downward projection 7272 exerts a force on upwardly facing surface of locking ledge 7276. Engagement between downward projection 7272 and upwardly facing surface of locking ledge 7276 may urge cartridge 7210 proximally within jaw 7202, thereby compressing leaf spring 7278.

Next, as shown in FIG. 33C, anvil jaw 7204 may be further pivoted toward jaw 7202 such that the tip of downward projection 7272 clears locking ledge 7276 and is housed within recessed pocket 7274. Since tip of downward projection 7272 no longer engaged upwardly facing surface of locking ledge 7276 to urge cartridge 7210 proximally to compress leaf spring 7278, leaf spring 7278 abuts against cartridge jaw 7202 to urge cartridge 7210 distally such that locking ledge 7276 and downward projection 7272 are suitably engaged with each other. As the moment shown in FIG. 33C, cartridge 7210 has been suitable coupled to jaw 7202 while datum locator 7270 has suitably positioned cartridge 7210 at its predetermined datum position.

Next, end effector 7200 may be suitably attached to a robotic arm, which may then pivot jaws 7202, 7204 in accordance with the description herein between the position shown in FIG. 33C and FIG. 33D.

Figure 34A:
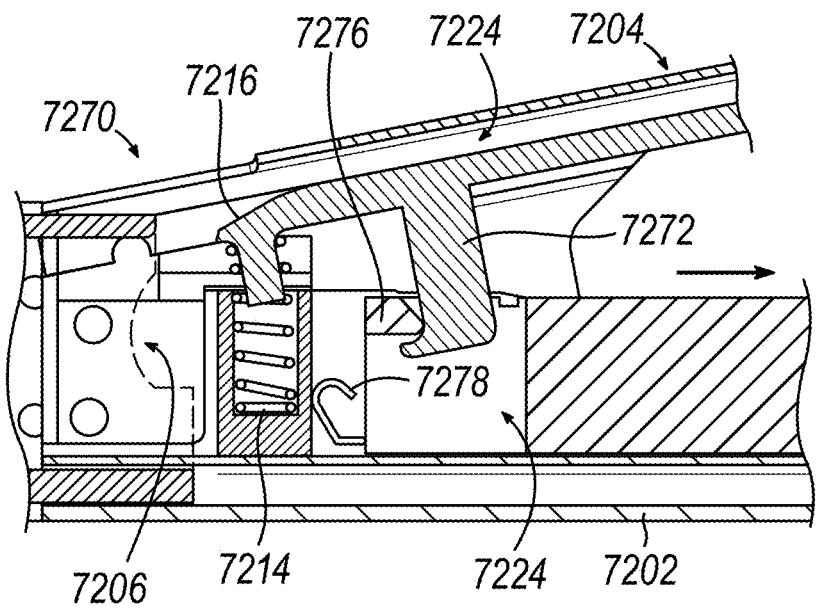
FIG. 34A is a cross-sectional view of the end effector of FIG. 31, where the staple cartridge datum locator of FIG. 33A is fully engaged while the end effector is in the intermediate open position.
Figure 34B:
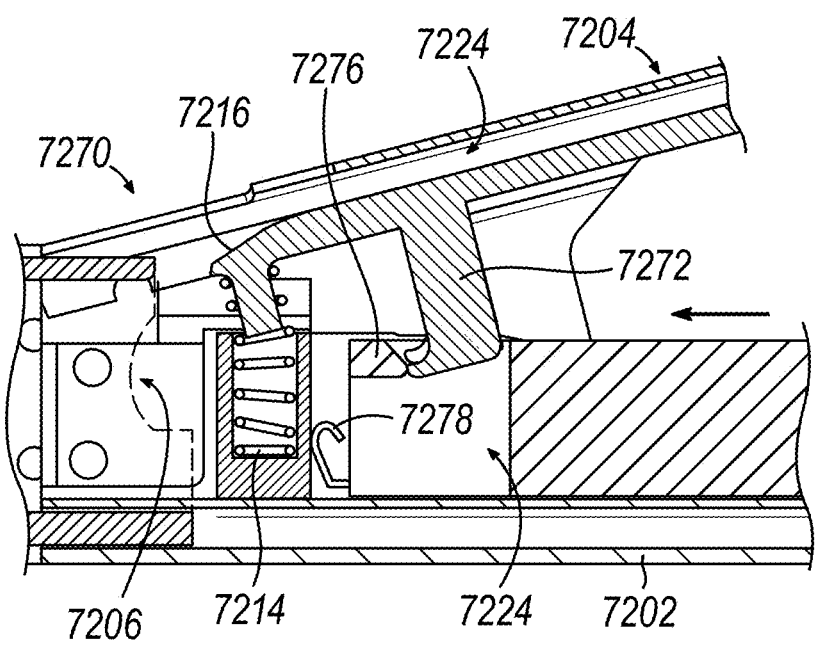
FIG. 34B is a cross-sectional view of the end effector of FIG. 31, where the staple cartridge datum locator of FIG. 33A is initially disengaged.
Figure 34C:
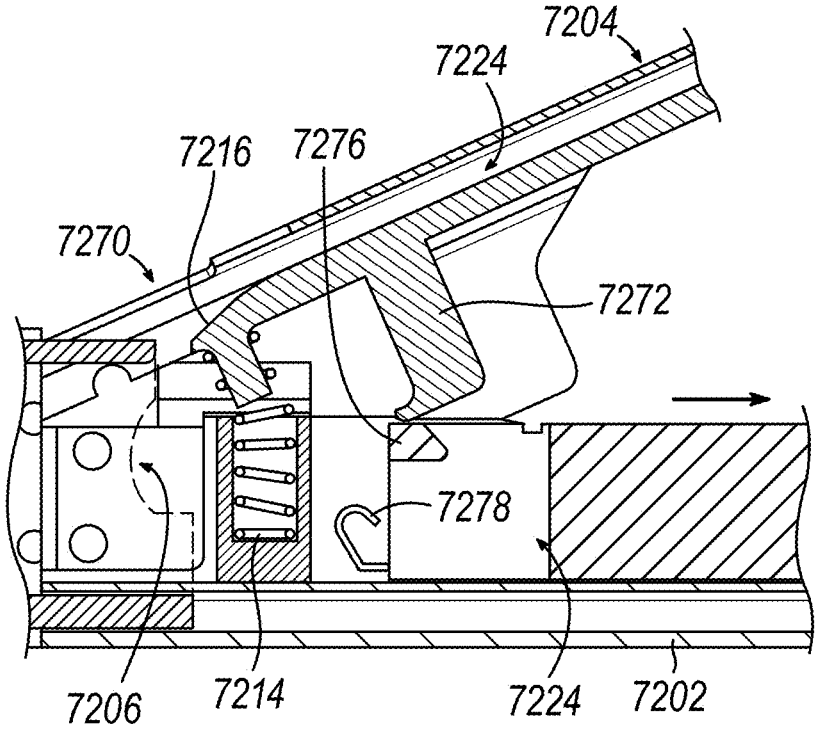
FIG. 34C is a cross-sectional view of the end effector of FIG. 31, where a staple cartridge is initially being attached to a cartridge jaw of the end effector, where the staple cartridge datum locator of FIG. 33A is disengaged.

After cartridge 7210 has been fired, end effector 7200 may be removed from robotic arm. Subsequently, a spent staple cartridge 7210 may be removed from jaw 7202. FIGS. 34A-34C show an illustrative decoupling of staple cartridge 7210 from jaw 7202. First, as shown between FIGS. 34A-34B, anvil jaw 7204 may be pivoted upwards by a user's hand toward the largest open position (P3). As a result, the tip of downward projection 7272 may cam against locking ledge 7276, thereby urging cartridge 7210 proximally and compressing leaf spring 7278. In some instances, a user may push cartridge 7210 proximally to compress leaf spring 7278, and anvil jaw 7204 may be biased open toward the largest open position (P3) via spring 7214. Once tip of downward projection 7272 is no longer within recessed pocket 7274, staple cartridge 7210 may be removed from jaw 7202.

III. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus (1000) comprising: (a) an end effector (1200, 2200, 2300, 3200, 4200, 5200, 6200) extending between a proximal portion and a distal portion, wherein the end effector is operable to clamp, staple, and cut tissue, comprising: (i) a first jaw (1202, 2202, 2302, 3202, 4202, 5202, 6202), configured to selectively receive a staple cartridge (1210, 2210, 2310, 3210, 4210, 5210, 6210), (ii) a second jaw (1204, 2204, 2304, 3204, 4204, 5204, 6204), wherein the first jaw and the second jaw are configured to transition between an open position and a closed position, (iii) a replaceable staple cartridge (1210, 2210, 2310, 3210, 4210, 5210, 6210) configured to selectively couple with the first jaw, and (iv) a knife sled (1236, 2236, 2336, 3236, 4236, 6236) configured to actuate relative to the first jaw and the second jaw along a firing stroke while the replaceable staple cartridge is housed within the first jaw to thereby cut and staple tissue clamped by the first and second jaws; and (b) a staple cartridge retainer (1290, 2290, 3290) located at the distal portion of the end effector, wherein the staple cartridge retainer is associated with the replaceable staple cartridge, wherein the staple retainer comprises a resilient retention body (1292, 2292, 3292) configured to inhibit the replaceable staple cartridge from disassociating with the first jaw; and (c) a staple cartridge datum locator (1270, 2270, 3270, 4270, 5270, 6270) associated with the second jaw and the replaceable staple cartridge, wherein the staple cartridge datum locator is located at the proximal portion of the end effector, wherein the staple cartridge datum locator is configured to position the replaceable staple cartridge at a predetermined datum location when the first jaw and the second jaw are in the closed position.

Example 2

The apparatus of Example 1, wherein the first jaw (1202) comprises a pair of lateral sidewalls (1280) each having a projection (1284), wherein the replaceable staple cartridge (1210) defines a longitudinally extending vertical alignment slot (1266) configured to receive the projection when the replaceable staple cartridge is coupled to the first jaw, wherein the laterally extending projection and the vertical alignment slot are configured to vertically restrain the replaceable staple cartridge relative to the first jaw.

Example 3

The apparatus of either Example 1 or 2, wherein the staple cartridge datum locator (1270) comprises an upwardly extending protrusion (1272) associated with the replaceable staple cartridge (1210).

Example 4

The apparatus of Example 3, wherein the staple cartridge datum locator (1270) comprises a complementary cavity (1276) defined by the second jaw (1204), wherein the complementary cavity is configured to engage the upwardly extending protrusion (1272) to thereby position the replaceable staple cartridge (1210) at its predetermined datum location when the first jaw and the second jaw are in the closed position.

Example 5

The apparatus of Example 4, wherein the second jaw (1204) comprise a first slanted engagement surface (1278), wherein the upwardly extending protrusion (1272) comprises a second slanted engagement surface (1275), wherein the first slanted engagement surface (1278) and the second slanted engagement surface (1275) are configured to engage each other to thereby position the replaceable staple cartridge (1210) at its predetermined datum location when the first jaw and the second jaw are in the closed position.

26

Example 6

The apparatus of either Example 1 or 2, wherein the staple cartridge datum locator (2270, 3270) comprises a downwardly extending projection (2272, 3272) associated with the second jaw (2204, 3204).

Example 7

The apparatus of Example 6, wherein the staple cartridge datum locator (2270, 3270) comprises a cavity (2274, 3274) defined by the replaceable staple cartridge (2210, 3210), wherein the cavity is dimensioned to receive the downwardly extending projection (3372, 3272) to thereby position the replaceable staple cartridge (1210) at its predetermined datum location when the first jaw and the second jaw are in the closed position.

Example 8

The apparatus of any one or more of Examples 1 through 7, wherein the staple cartridge datum locator (1270, 5270) defines a particulate channel (1274, 5274) dimensioned to receive excess matter while first jaw and the second jaw are in the closed position.

Example 9

The apparatus of any one or more of Examples 1 through 8, wherein the cartridge datum locator (6200) includes a bias spring (6276).

Example 10

The apparatus of Example 9, wherein the knife sled (6236) is configured to overcome the bias spring (6276) to position the replaceable staple cartridge at its predetermined datum location when the first jaw and the second jaw are in the closed position.

Example 11

The apparatus of any one or more of Examples 1 through 10, wherein the staple cartridge retainer (2290) comprise a bias element (2295) configured to bias the replaceable staple cartridge (2210) proximally within the first jaw (2202).

Example 12

The apparatus of Example 11, wherein the bias element (2295) is configured to bias the staple cartridge datum locator (2270) into a configuration that positions the replaceable staple cartridge at its predetermined datum location when the first jaw and the second jaw are in the open position.

Example 13

The apparatus of any one or more of Examples 1 through 12, wherein the second jaw (1204, 2204, 2304, 3204, 4204, 5204, 6204) comprises a plurality of staple forming pockets (1205).

Example 14

The apparatus of any one or more of Examples 1 through 13, wherein the resilient retention body (1292, 2292, 3292) comprises a latch.

Example 15

The apparatus of any one or more of Examples 1 through 14, wherein the first jaw (1202) and the second jaw (1204) are pivotally coupled via a pivot pin (1212).

The following clauses also relate to various non-exhaustive ways in which the teachings herein may be combined or applied.

Clause 1.

1. An apparatus comprising:
   (a) an end effector extending between a proximal portion and a distal portion, wherein the end effector is operable to clamp, staple, and cut tissue, comprising:
      (i) a first jaw configured to selectively receive a staple cartridge,
      (ii) a second jaw, wherein the first jaw and the second jaw are configured to transition between an open position and a closed position,
      (iii) a replaceable staple cartridge configured to selectively couple with the first jaw, and
      (iv) a knife sled configured to actuate relative to the first jaw and the second jaw along a firing stroke while the replaceable staple cartridge is seated within the first jaw to thereby cut and staple tissue clamped by the first and second jaws;
   (b) a staple cartridge retainer associated with the replaceable staple cartridge and located at the distal portion of the end effector, wherein the staple cartridge retainer comprises a resilient retention body configured to inhibit the replaceable staple cartridge from disassociating with the first jaw; and
   (c) a staple cartridge datum locator associated with the second jaw and the replaceable staple cartridge, wherein the staple cartridge datum locator is located at the proximal portion of the end effector and is configured to position the replaceable staple cartridge at a predetermined datum location when the first jaw and the second jaw are in the closed position.

Clause 2.

2. The apparatus of Clause 1, wherein the first jaw comprises a pair of lateral sidewalls each having a projection, wherein the replaceable staple cartridge defines a longitudinally extending vertical alignment slot configured to receive the projection when the replaceable staple cartridge is coupled to the first jaw, wherein the laterally extending projection and the vertical alignment slot are configured to vertically restrain the replaceable staple cartridge relative to the first jaw.

Clause 3.

The apparatus of either Clause 1 or 2, wherein the staple cartridge datum locator comprises an upwardly extending protrusion associated with the replaceable staple cartridge.

Clause 4.

4. The apparatus of Clause 3, wherein the staple cartridge datum locator comprises a complementary cavity defined by the second jaw, wherein the complementary cavity is configured to engage the upwardly extending protrusion to thereby position the replaceable staple cartridge at its predetermined datum location when the first jaw and the second jaw are in the closed position.

Clause 5.

5. The apparatus of Clause 4, wherein the second jaw comprise a first slanted engagement surface, wherein the upwardly extending protrusion comprises a second slanted engagement surface, wherein the first slanted engagement surface and the second slanted engagement surface are configured to engage each other to thereby position the replaceable staple cartridge at its predetermined datum location when the first jaw and the second jaw are in the closed position.

Clause 6.

6. The apparatus of either Clause 1 or 2, wherein the staple cartridge datum locator comprises a downwardly extending projection associated with the second jaw.

Clause 7.

7. The apparatus of Clause 5, wherein the staple cartridge datum locator comprises a cavity defined by the replaceable staple cartridge, wherein the cavity is dimensioned to receive the downwardly extending projection to thereby position the replaceable staple cartridge at its predetermined datum location when the first jaw and the second jaw are in the closed position.

Clause 8.

8. The apparatus of any one or more of Clauses 1 through 7, wherein the staple cartridge datum locator defines a particulate channel dimensioned to receive excess matter while first jaw and the second jaw are in the closed position.

Clause 9.

9. The apparatus of any one or more of Clauses 1 through 5, wherein the cartridge datum locator includes a bias spring.

Clause 10.

10. The apparatus of Clause 9, wherein the knife sled is configured to overcome the bias spring to position the replaceable staple cartridge at its predetermined datum location when the first jaw and the second jaw are in the closed position.

Clause 11.

11. The apparatus of any one or more of Clause 1 through 10, wherein the staple cartridge retainer comprise a bias element configured to bias the replaceable staple cartridge proximally within the first jaw.

Clause 12.

12. The apparatus of Clause 11, wherein the bias element is configured to bias the staple cartridge datum locator into a configuration that positions the replaceable staple cartridge at its predetermined datum location when the first jaw and the second jaw are in the open position.

Clause 13.

13. The apparatus of any one or more of Clause 1 through 12, wherein the second jaw comprises a plurality of staple forming pockets.

Clause 14.

14. The apparatus of any one or more of Clauses 1 through 13, wherein the resilient retention body comprises a latch.

Clause 15.

15. The apparatus of any one or more of Clauses 1 through 14, wherein the first jaw and the second jaw are pivotally coupled via a pivot pin.

Clause 16.

16. An apparatus comprising:

(a) an end effector extending between a proximal portion and a distal portion, wherein the end effector is operable to clamp, staple, and cut tissue, comprising:

(i) a first jaw configured to selectively receive a staple cartridge, (ii) a second jaw, wherein the first jaw and the second jaw are configured to transition between an open position and a closed position, (iii) a staple cartridge configured to couple with the first jaw, and (iv) a knife sled configured to actuate relative to the first jaw and the second jaw along a firing stroke while the replaceable staple cartridge is seated within the first jaw to thereby cut and staple tissue clamped by the first and second jaws;

(b) a staple cartridge retainer configured to inhibit the replaceable staple cartridge from disassociating from the first jaw; and (c) a staple cartridge datum locator associated with the second jaw and the replaceable staple cartridge, wherein the staple cartridge datum locator is configured to position the replaceable staple cartridge at a predetermined datum location.

Clause 17.

17. The apparatus of Clause 16, wherein the staple cartridge retainer comprises a resilient latch.

Clause 18.

18. The apparatus of Clause 17, wherein the resilient latch comprises a resilient base and a latch head.

Clause 19.

19. The apparatus of Clause 18, wherein the resilient latch comprises an intermediate section interposed between the latch head and the resilient base.

Clause 20.

20 An apparatus comprising:

(a) an end effector extending between a proximal portion and a distal portion, wherein the end effector is operable to clamp, staple, and cut tissue, comprising:

(i) a first jaw configured to selectively receive a staple cartridge, (ii) a second jaw, wherein the first jaw and the second jaw are configured to transition between an open position and a closed position, and (iii) a staple cartridge configured to couple with the first jaw;

(b) a staple cartridge retainer configured to inhibit the replaceable staple cartridge from disassociating from the first jaw in the open position; and (c) a staple cartridge datum locator associated with the second jaw and the replaceable staple cartridge, wherein the staple cartridge datum locator is configured to position the replaceable staple cartridge at a predetermined datum location in response to the first jaw and the second jaw transitioning into the closed position.

IV. Miscellaneous

It should be understood that any one or more of the teachings, expressions, versions, examples, etc. described herein may be combined with any one or more of the other teachings, expressions, versions, examples, etc. that are described herein. The above-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
(a) an end effector extending between a proximal portion and a distal portion, wherein the end effector is operable to clamp, staple, and cut tissue, comprising:
(i) a first jaw configured to selectively receive a staple cartridge, wherein the first jaw comprises a side wall,
(ii) a second jaw, wherein the first jaw and the second jaw are configured to transition between an open position and a closed position,
(iii) a replaceable staple cartridge configured to selectively couple with the first jaw, and
(iv) a knife sled configured to actuate relative to the first jaw and the second jaw along a firing stroke while the replaceable staple cartridge is seated within the first jaw to thereby cut and staple tissue clamped by the first and second jaws;
(b) a staple cartridge retainer associated with the replaceable staple cartridge and located at the distal portion of the end effector, wherein the staple cartridge retainer comprises a resilient retention body configured to inhibit the replaceable staple cartridge from disassociating with the first jaw, wherein the resilient retention body comprises a latch head and a resilient grip attached to the latch head, wherein the latch head is configured to engage a portion of the side wall to selectively couple the replaceable staple cartridge with the first jaw, wherein the resilient grip extends distally past a distal most end of the side wall when the replaceable staple cartridge is selectively coupled with the first jaw; and
(c) a staple cartridge datum locator associated with the second jaw and the replaceable staple cartridge, wherein the staple cartridge datum locator is located at the proximal portion of the end effector and is configured to position the replaceable staple cartridge at a predetermined datum location when the first jaw and the second jaw are in the closed position.

2. The apparatus of claim 1, wherein the first jaw comprises a pair of lateral sidewalls each having a projection, wherein the replaceable staple cartridge defines a longitudinally extending vertical alignment slot configured to receive the projection when the replaceable staple cartridge is coupled to the first jaw, wherein the projection and the vertical alignment slot are configured to vertically restrain the replaceable staple cartridge relative to the first jaw.

3. The apparatus of claim 1, wherein the staple cartridge datum locator comprises an upwardly extending protrusion associated with the replaceable staple cartridge.

4. The apparatus of claim 3, wherein the staple cartridge datum locator comprises a complementary cavity defined by the second jaw, wherein the complementary cavity is configured to engage the upwardly extending protrusion to thereby position the replaceable staple cartridge at its predetermined datum location when the first jaw and the second jaw are in the closed position.

5. The apparatus of claim 4, wherein the second jaw comprises a first slanted engagement surface, wherein the upwardly extending protrusion comprises a second slanted engagement surface, wherein the first slanted engagement surface and the second slanted engagement surface are configured to engage each other to thereby position the replaceable staple cartridge at its predetermined datum location when the first jaw and the second jaw are in the closed position.

6. The apparatus of claim 1, wherein the staple cartridge datum locator defines a particulate channel dimensioned to receive excess matter while the first jaw and the second jaw are in the closed position.

7. The apparatus of claim 1, wherein the second jaw comprises a plurality of staple forming pockets.

8. The apparatus of claim 1, wherein the first jaw and the second jaw are pivotally coupled via a pivot pin.

9. An apparatus comprising:
(a) an end effector extending between a proximal portion and a distal portion, wherein the end effector is operable to clamp, staple, and cut tissue, comprising:
(i) a first jaw configured to selectively receive a staple cartridge, wherein the first jaw comprises a side wall,
(ii) a second jaw, wherein the first jaw and the second jaw are configured to transition between an open position and a closed position,
(iii) a staple cartridge configured to couple with the first jaw, and
(iv) a knife sled configured to actuate relative to the first jaw and the second jaw along a firing stroke while the staple cartridge is seated within the first jaw to thereby cut and staple tissue clamped by the first and second jaws;
(b) a staple cartridge retainer comprising a resilient grip and a latch head attached to the resilient grip, wherein the latch head is configured to engage the side wall of the first jaw while the staple cartridge is coupled with the first jaw to thereby inhibit the staple cartridge from disassociating from the first jaw, wherein the resilient grip extends distally from the latch head and is located distally relative to a distal most end of the side wall while the staple cartridge is coupled with the first jaw; and
(c) a staple cartridge datum locator associated with the second jaw and the staple cartridge, wherein the staple cartridge datum locator is configured to position the staple cartridge at a predetermined datum location.

10. The apparatus of claim 9, wherein the staple cartridge retainer comprises an intermediate section interposed between the latch head and the resilient grip.

11. An apparatus comprising:
(a) an end effector extending between a proximal portion and a distal portion, wherein the end effector is operable to clamp, staple, and cut tissue, comprising:
(i) a first jaw configured to selectively receive a staple cartridge, wherein the first jaw comprises a side wall defining a hole,
(ii) a second jaw, wherein the first jaw and the second jaw are configured to transition between an open position and a closed position, and
(iii) a staple cartridge configured to couple with the first jaw;
(b) a staple cartridge retainer configured to inhibit the staple cartridge from disassociating from the first jaw in the open position, wherein the staple cartridge retainer comprises a latch head and a resilient grip, wherein the latch head is configured to fit within the hole of the side wall when the staple cartridge is coupled with the first jaw, wherein the resilient grip extends distally from the latch head and a distal most end of the side wall, wherein the resilient grip is accessible to a user while the staple cartridge is coupled with the first jaw; and (c) a staple cartridge datum locator associated with the second jaw and the staple cartridge, wherein the staple cartridge datum locator is configured to position the staple cartridge at a predetermined datum location in response to the first jaw and the second jaw transitioning into the closed position.

* * * * *